United States Patent [19]

Stillman et al.

[11] Patent Number: 5,589,341
[45] Date of Patent: Dec. 31, 1996

[54] ORIGIN OF REPLICATION COMPLEX GENES AND METHODS OF USING THE SAME

[75] Inventors: Bruce W. Stillman; Stephen P. Bell; Ryuji Kobayashi, all of Cold Spring Harbor, N.Y.; Jasper Rine, Moraga, Calif.; Margit Foss, Durham, N.C.; Francis J. McNally, Davis, Calif.; Patricia Laurenson, San Francisco, Calif.; Ira Herskowitz, Berkeley, Calif.; Joachim Li, San Francisco, Calif.; Kimberly Gavin; Masumi Hidaka, both of Cold Spring Harbor, N.Y.

[73] Assignees: Cold Spring Harbor Laboratory, Cold Spring Harbor, N.Y.; The Regents of the University of California, Oakland, Calif.

[21] Appl. No.: 484,105

[22] Filed: Jun. 7, 1995

Related U.S. Application Data

[62] Division of Ser. No. 168,479, Dec. 16, 1993, abandoned.

[51] Int. Cl.$^6$ .............. C12Q 1/68; C12N 15/00; C12N 1/15; C07K 14/39

[52] U.S. Cl. .............. 435/6; 435/69.2; 435/240.2; 435/255.1; 935/59; 935/70; 935/77; 530/388.21

[58] Field of Search .............. 435/6, 69.2, 240.2; 935/59, 70, 77; 530/388.21

*Primary Examiner*—Mindy Fleisher
*Assistant Examiner*—Bonnie D. Weiss
*Attorney, Agent, or Firm*—Richard Aron Osman

[57] ABSTRACT

Origin of Replication Complex (ORC) genes, nucleic acids which encode ORC proteins and hybridization reagents, probes and primers capable of hybridizing with ORC genes and methods for screening chemical libraries for lead compounds for pharmacological agents useful in the diagnosis or treatment of disease associated undesirable cell growth are provided. An exemplary screen involves forming a mixture comprising a recombinant ORC protein, a natural intracellular ORC protein binding target, and a candidate pharmacological agent; incubating the mixture under conditions whereby, but for the presence of said candidate pharmacological agent, said ORC protein selectively binds said binding target; and detecting the presence or absence of specific binding of said ORC protein to said binding target.

21 Claims, No Drawings

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
      ( A ) LENGTH: 4940 base pairs
      ( B ) TYPE: nucleic acid
      ( C ) STRANDEDNESS: double
      ( D ) TOPOLOGY: linear ( i i ) MOLECULE TYPE: cDNA ( x i ) SEQUENCE DESCRIPTION: SEQ ID NO:1:

```
ATAACATGCT CGCCCTTTTA TATTATGACA GAAAGAATAT ATATATTCAT ATATAAGATG      60

CTTCTATTTA TTAGTTTTAT CTTTTAATTG ATGATGTGTC CATAGAATTT AAGTAAGTGC     120

ATGGTATGGA GTGTATAATG GTTTATAATT TCCCCTAAGA TGACACAAAA AAATGTTCTC     180

CCAAAAATTT ACCAAGAAAA AAAATTAAGA ATACTACACA ATTGATGCTT GGGTTATTTT     240

AAATATCCGG TACATTCTAT TACAAATATG TTTGTACAAT GTAAGCCCCT TCATAATGGT     300

CAGTATTAAG ATAAGGACTG CTATGGGGCA TTTTTTGTCT TACTGGGTAT CACAGGATAA     360
```

-continued

| | | | | | |
|---|---|---|---|---|---|
|TAACTTGGCG|CCAAATTAGA|AAAGATATAA|ACCTCAAATA|TTTGAAATTC|TTTGGTGACC|420
|TGTCTCATCG|TTATATCAAC|AAATATTGCA|CCAACGAACA|CCACTACATA|TGTAACTACT|480
|CTCTTCCTCG|ACTTATTTTT|TATTAACGTT|GACACGGCCA|GATCGAAAAT|CATAGAAAAA|540
|CAACAACATT|GAGAAGAGAT|GAAGTTGCGC|AAAGGGAAAG|AAAACTGCAT|AGGCGGCAAA|600
|TTCAGCCTAA|AAGTTTCCAG|AAGCAGGAAC|TCATTCCCTA|TTGATTAATA|CTCATTACAA|660
|AAACCACAAT|AGAGTAGATA|AGATGGCAAA|AACGTTGAAG|GATTTACAGG|GTTGGGAGAT|720
|AATAACAACT|GATGAGCAGG|GAAATATAAT|CGATGGAGGT|CAGAAGAGAT|TACGCCGAAG|780
|AGGTGCAAAA|ACTGAACATT|ACTTAAAGAG|AAGTTCTGAT|GGAATTAAAC|TAGGTCGTGG|840
|TGATAGTGTA|GTCATGCACA|ACGAAGCCGC|TGGGACTTAC|TCCGTTTATA|TGATCCAGGA|900
|GTTGAGACTT|AATACATTAA|ATAATGTTGT|CGAACTCTGG|GCTCTCACCT|ATTTACGATG|960
|GTTGAAGTC|AATCCTTTAG|CTCATTATAG|GCAGTTTAAT|CCTGACGCTA|ACATTTTGAA|1020
|TCGTCCTTTA|AATTATTACA|ATAAACTGTT|TTCTGAAACT|GCAAATAAAA|ATGAACTGTA|1080
|TCTCACTGCA|GAATTAGCCG|AATTGCAGCT|ATTTAACTTT|ATCAGGGTTG|CCAACGTAAT|1140
|GGATGGAAGC|AAATGGGAAG|TATTGAAAGG|AAATGTCGAT|CCAGAAAGAG|ACTTTACAGT|1200
|TCGTTATATT|TGTGAGCCGA|CTGGGGAGAA|ATTTGTGGAC|ATTAATATTG|AGGATGTCAA|1260
|AGCTTACATA|AAGAAAGTGG|AGCCAAGGGA|AGCCCAGGAA|TATTTGAAAG|ATTTAACACT|1320
|TCCATCAAAG|AAGAAAGAGA|TCAAAGAGG|TCCTCAAAAG|AAAGATAAGG|CTACTCAAAC|1380
|GGCACAAATT|TCAGACGCAG|AAACAAGAGC|TACAGATATA|ACGGATAATG|AGGACGGTAA|1440
|TGAAGATGAA|TCATCTGATT|ATGAAAGTCC|GTCAGATATC|GACGTTAGCG|AGGATATGGA|1500
|CAGCGGTGAA|ATATCCGCAG|ATGAGCTTGA|GGAAGAAGAA|GACGAAGAAG|AAGACGAAGA|1560
|CGAAGAAGAG|AAAGAAGCTA|GGCATACAAA|TTCACCAAGG|AAAAGAGGCC|GTAAGATAAA|1620
|ACTAGGTAAA|GATGATATTG|ACGCTTCTGT|ACAACCTCCC|CCCAAAAAAA|GAGGTCGTAA|1680
|ACCTAAAGAT|CCTAGTAAAC|CGCGTCAGAT|GCTATTGATA|TCTTCATGCC|GTGCAAATAA|1740
|TACTCCTGTG|ATTAGGAAAT|TTACAAAAAA|GAATGTTGCT|AGGGCGAAAA|AGAAATATAC|1800
|CCCGTTTTCG|AAAAGATTTA|AATCTATAGC|TGCAATACCA|GATTTAACTT|CATTACCTGA|1860
|ATTTTACGGA|AATTCTTCGG|AATTGATGGC|ATCAAGGTTT|GAAAACAAAT|TAAAAACAAC|1920
|CCAAAAGCAT|CAGATTGTAG|AAACAATTTT|TTCTAAAGTC|AAAAAACAGT|TGAACTCTTC|1980
|GTATGTCAAA|GAAGAAATAT|TGAAGTCTGC|AAATTTCCAA|GATTATTTAC|CGGCTAGGGA|2040
|GAATGAATTC|GCCTCAATTT|ATTTAAGTGC|ATATAGTGCC|ATTGAGTCCG|ACTCCGCTAC|2100
|TACTATATAC|GTGGCTGGTA|CGCCTGGTGT|AGGGAAAACT|TTAACCGTAA|GGGAAGTCGT|2160
|AAAGGAACTA|CTATCGTCTT|CTGCACAACG|AGAAATACCA|GACTTTCTTT|ATGTGGAAAT|2220
|AAATGGATTG|AAAATGGTAA|AACCCACAGA|CTGTTACGAA|ACTTTATGGA|ACAAAGTGTC|2280
|AGGAGAAAGG|TTAACATGGG|CAGCTTCAAT|GGAGTCACTA|GAGTTTTACT|TTAAAAGAGT|2340
|TCCAAAAAAT|AAGAAGAAAA|CCATTGTAGT|CTTGTTGGAC|GAACTCGATG|CCATGGTAAC|2400
|GAAATCTCAA|GATATTATGT|ACAATTTTTT|CAATTGGACT|ACTTACGAAA|ATGCCAAACT|2460
|TATTGTCATT|GCAGTAGCCA|ATACAATGGA|CTTACCAGAA|CGTCAGCTAG|GCAATAAGAT|2520
|TACTTCAAGA|ATTGGGTTTA|CCAGAATTAT|GTTCACTGGG|TATACGCACG|AAGAGCTAAA|2580
|AAATATCATT|GATTTAAGAC|TGAAGGGGTT|GAACGACTCA|TTTTTCTATG|TTGATACAAA|2640
|AACTGGCAAT|GCTATTTTGA|TTGATGCGGC|TGGAAACGAC|ACTACAGTTA|AGCAAACGTT|2700
|GCCTGAAGAC|GTGAGGAAAG|TTCGCTTAAG|AATGAGTGCT|GATGCCATTG|AAATAGCTTC|2760

```
GAGAAAAGTA GCAAGTGTTA GTGGTGATGC AAGAAGAGCA TTGAAGGTTT GTAAAAGAGC    2820
AGCTGAAATT GCTGAAAAAC ACTATATGGC TAAGCATGGT TATGGATATG ATGGAAAGAC    2880
GGTTATTGAA GATGAAAATG AGGAGCAAAT ATACGATGAT GAAGACAAGG ATCTTATTGA    2940
AAGTAACAAA GCCAAGACG  ATAATGATGA CGATGATGAC AATGATGGGG TACAAACAGT    3000
TCACATCACG CACGTTATGA AAGCCTTAAA CGAAACTTTA AATTCTCATG TAATTACGTT    3060
TATGACGCGA CTTTCATTTA CAGCAAAACT GTTTATTTAT GCATTATTAA ACTTGATGAA    3120
AAAGAACGGA TCTCAAGAGC AAGAACTGGG CGATATTGTC GATGAAATCA AGTTACTTAT    3180
TGAAGTAAAT GGCAGTAATA AGTTTGTCAT GGAGATAGCC AAAACATTGT TCCAACAGGG    3240
AAGTGATAAT ATTTCTGAAC AATTGAGAAT TATATCATGG GATTTCGTTC TCAATCAGTT    3300
ACTTGACGCG GGAATATTGT TTAAACAAAC TATGAAGAAC GATAGAATAT GTTGTGTCAA    3360
GCTAAATATA TCAGTAGAAG AAGCCAAAAG AGCCATGAAT GAGGATGAGA CATTGAGAAA    3420
TTTATAGATT CGGTTTTTAT TATTCATGAC CTAGCATACA CATACATATA CCTACATAGT    3480
AGCGCATTTA TCCAAAACAT ACGATATTGT GGATGTACAT ACCTTCTATA TCTCCTTAAA    3540
GCTATTGTGT AGCTTGATTT AAAATATGCT AACGCCAACT CTCACATGGT AGCAGGCGGG    3600
TATAGTTGTT TTCATGTATT AACGCCCGGC GATGGTGCCT TAGATGAGGG CGACGAGGAG    3660
GGCTTCCTGA TATTATGGCT CTTTCTATCC TGACTTTTGT TATGATGTCG ATGTTGCTGG    3720
CCACCTAGGT GCTTATATAT CAAAGAGGA  TCGCCGATTT CATTGATTTC TGGGATGGTT    3780
AATGTCAAAT TAAAGATCTT TGCCAGTGCA ATTTTGAAAA TTTTTTGAAT GTTTATAGAT    3840
TTGGCAGTAG AGCAGAATAT AAGAGGAGCA TTCATGACCT GTGCATACTT CATACTCGTT    3900
CTCGAGATTT GTTCCTGATA TTCCGGGTCT AAGTCTATTA GTAAATCGTA CTTTGTGCCC    3960
ACCAAAATAG GAATTGCCGA ATCATTTAGC CCGTACGCCT GCCTATACCA CTCCTTTATT    4020
GAACTCAACG TCTCTGGACG TGTCAGGTCA AACAGAAATA TGATCACTGA AGACCCTACC    4080
GTCGCAATTG GGAGCATGTT GATGAATTCT CTTTGTCCGC CTAAATCCAT TATAGAAAAT    4140
ATAATATCCG TGGAGCGTAT GCTTACTTTT CTTTTCAAAA AGTTCACTCC CAGCGTCTGT    4200
GTGTATTCCT TATCGTATAT GTTCTGTACG TACTTCACCA TCAGCGATGT TTTCCCTACT    4260
TGTGCATCCC CTACTAATCC AACCTGAACT TCAACCTGAT TTCGTACCGC AGGTATAGAA    4320
TTGTTTGCTC CCGTGCTTGG TGTAGCCATC TTAGCTTAAC TCAATTTAAT TTCTACAGCA    4380
AAATCCAAAC GTAATATCTA TATTTTTCTC GAAAAACTGA GGACAAGAGC CAATCAATCA    4440
TCTATAATCC AATTTATATT ATTTTTTCCC TTCTGGGTTC TTTTCTTCCT TTTCTTGTTT    4500
ACCTTTTTTG CTTTTTCATA AAATAATTTC TCTAGATTTG AAGACAGCAT TTTTGTACAT    4560
CCATACACCA TACACCATAC ACCATAGCAC CAGTACACTA TATTTTATG  AATTTTACTA    4620
AGAATTATTC CTGCAGGAGC TCCACTGAAA AAAAAAGAGC AGCATGGATG TCATGTCGGT    4680
AGAGTGCTAC TGAGTAAATG GGAGGACGCG GTAGATCCAG TGTGGAATCA AGGTGGTGCC    4740
GGTGTGAAGC CGCCTCGGCC GGCTGGACTC TCCAGGCCGG AGTGATGATT GCCACGCTGA    4800
AGCTAACACA GTTTCACAAT ACCAGTGTCC TCATTAGTGA GTTCCAATGT ATAGTTAGTA    4860
GTGGTATTTT GATATATGTG AGTGGTAGCA GATTTGAACT TAGTTAGTTG TATTCGCCTT    4920
TGAGGAAACC AAGCCAAAAA                                                4940
```

( 2 ) INFORMATION FOR SEQ ID NO:2:

( i ) SEQUENCE CHARACTERISTICS:
        ( A ) LENGTH: 914 amino acids ( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:2:

| Met | Ala | Lys | Thr | Leu | Lys | Asp | Leu | Gln | Gly | Trp | Glu | Ile | Ile | Thr | Thr |
|---|---|---|---|---|---|---|---|---|---|---|---|---|---|---|---|
| 1 | | | | 5 | | | | | 10 | | | | | 15 | |
| Asp | Glu | Gln | Gly | Asn | Ile | Ile | Asp | Gly | Gly | Gln | Lys | Arg | Leu | Arg | Arg |
| | | | 20 | | | | | 25 | | | | | 30 | | |
| Arg | Gly | Ala | Lys | Thr | Glu | His | Tyr | Leu | Lys | Arg | Ser | Ser | Asp | Gly | Ile |
| | | | 35 | | | | 40 | | | | | 45 | | | |
| Lys | Leu | Gly | Arg | Gly | Asp | Ser | Val | Val | Met | His | Asn | Glu | Ala | Ala | Gly |
| | | 50 | | | | 55 | | | | | 60 | | | | |
| Thr | Tyr | Ser | Val | Tyr | Met | Ile | Gln | Glu | Leu | Arg | Leu | Asn | Thr | Leu | Asn |
| 65 | | | | | 70 | | | | | 75 | | | | | 80 |
| Asn | Val | Val | Glu | Leu | Trp | Ala | Leu | Thr | Tyr | Leu | Arg | Trp | Phe | Glu | Val |
| | | | | 85 | | | | | 90 | | | | | 95 | |
| Asn | Pro | Leu | Ala | His | Tyr | Arg | Gln | Phe | Asn | Pro | Asp | Ala | Asn | Ile | Leu |
| | | | | 100 | | | | | 105 | | | | | 110 | |
| Asn | Arg | Pro | Leu | Asn | Tyr | Tyr | Asn | Lys | Leu | Phe | Ser | Glu | Thr | Ala | Asn |
| | | | 115 | | | | | 120 | | | | | 125 | | |
| Lys | Asn | Glu | Leu | Tyr | Leu | Thr | Ala | Glu | Leu | Ala | Glu | Leu | Gln | Leu | Phe |
| | | 130 | | | | | 135 | | | | | 140 | | | |
| Asn | Phe | Ile | Arg | Val | Ala | Asn | Val | Met | Asp | Gly | Ser | Lys | Trp | Glu | Val |
| 145 | | | | | 150 | | | | | 155 | | | | | 160 |
| Leu | Lys | Gly | Asn | Val | Asp | Pro | Glu | Arg | Asp | Phe | Thr | Val | Arg | Tyr | Ile |
| | | | | 165 | | | | | 170 | | | | | 175 | |
| Cys | Glu | Pro | Thr | Gly | Glu | Lys | Phe | Val | Asp | Ile | Asn | Ile | Glu | Asp | Val |
| | | | 180 | | | | | 185 | | | | | 190 | | |
| Lys | Ala | Tyr | Ile | Lys | Lys | Val | Glu | Pro | Arg | Glu | Ala | Gln | Glu | Tyr | Leu |
| | | | 195 | | | | | 200 | | | | | 205 | | |
| Lys | Asp | Leu | Thr | Leu | Pro | Ser | Lys | Lys | Lys | Glu | Ile | Lys | Arg | Gly | Pro |
| | | 210 | | | | | 215 | | | | | 220 | | | |
| Gln | Lys | Lys | Asp | Lys | Ala | Thr | Gln | Thr | Ala | Gln | Ile | Ser | Asp | Ala | Glu |
| 225 | | | | | 230 | | | | | 235 | | | | | 240 |
| Thr | Arg | Ala | Thr | Asp | Ile | Thr | Asp | Asn | Glu | Asp | Gly | Asn | Glu | Asp | Glu |
| | | | | 245 | | | | | 250 | | | | | 255 | |
| Ser | Ser | Asp | Tyr | Glu | Ser | Pro | Ser | Asp | Ile | Asp | Val | Ser | Glu | Asp | Met |
| | | | 260 | | | | | 265 | | | | | 270 | | |
| Asp | Ser | Gly | Glu | Ile | Ser | Ala | Asp | Glu | Leu | Glu | Glu | Glu | Glu | Asp | Glu |
| | | | 275 | | | | 280 | | | | | 285 | | | |
| Glu | Glu | Asp | Glu | Asp | Glu | Glu | Glu | Lys | Glu | Ala | Arg | His | Thr | Asn | Ser |
| | 290 | | | | | 295 | | | | | 300 | | | | |
| Pro | Arg | Lys | Arg | Gly | Arg | Lys | Ile | Lys | Leu | Gly | Lys | Asp | Asp | Ile | Asp |
| 305 | | | | | 310 | | | | | 315 | | | | | 320 |
| Ala | Ser | Val | Gln | Pro | Pro | Pro | Lys | Lys | Arg | Gly | Arg | Lys | Pro | Lys | Asp |
| | | | | 325 | | | | | 330 | | | | | 335 | |
| Pro | Ser | Lys | Pro | Arg | Gln | Met | Leu | Leu | Ile | Ser | Ser | Cys | Arg | Ala | Asn |
| | | | 340 | | | | | 345 | | | | | 350 | | |
| Asn | Thr | Pro | Val | Ile | Arg | Lys | Phe | Thr | Lys | Lys | Asn | Val | Ala | Arg | Ala |
| | | 355 | | | | | 360 | | | | | 365 | | | |
| Lys | Lys | Lys | Tyr | Thr | Pro | Phe | Ser | Lys | Arg | Phe | Lys | Ser | Ile | Ala | Ala |
| | 370 | | | | | 375 | | | | | 380 | | | | |

| | | | | | | | | | | | | | | |
|---|---|---|---|---|---|---|---|---|---|---|---|---|---|---|
| Ile 385 | Pro | Asp | Leu | Thr | Ser 390 | Leu | Pro | Glu | Phe 395 | Tyr | Gly | Asn | Ser | Ser Glu 400 |
| Leu | Met | Ala | Ser | Arg 405 | Phe | Glu | Asn | Lys | Leu 410 | Lys | Thr | Thr | Gln | Lys His 415 |
| Gln | Ile | Val | Glu 420 | Thr | Ile | Phe | Ser | Lys 425 | Val | Lys | Lys | Gln | Leu 430 | Asn Ser |
| Ser | Tyr | Val 435 | Lys | Glu | Glu | Ile | Leu 440 | Lys | Ser | Ala | Asn | Phe 445 | Gln | Asp Tyr |
| Leu | Pro 450 | Ala | Arg | Glu | Asn | Glu 455 | Phe | Ala | Ser | Ile | Tyr 460 | Leu | Ser | Ala Tyr |
| Ser 465 | Ala | Ile | Glu | Ser | Asp 470 | Ser | Ala | Thr | Thr | Ile 475 | Tyr | Val | Ala | Gly Thr 480 |
| Pro | Gly | Val | Gly | Lys 485 | Thr | Leu | Thr | Val | Arg 490 | Glu | Val | Val | Lys | Glu Leu 495 |
| Leu | Ser | Ser | Ser 500 | Ala | Gln | Arg | Glu | Ile 505 | Pro | Asp | Phe | Leu | Tyr 510 | Val Glu |
| Ile | Asn | Gly 515 | Leu | Lys | Met | Val | Lys 520 | Pro | Thr | Asp | Cys | Tyr 525 | Glu | Thr Leu |
| Trp | Asn 530 | Lys | Val | Ser | Gly | Glu 535 | Arg | Leu | Thr | Trp | Ala 540 | Ala | Ser | Met Glu |
| Ser 545 | Leu | Glu | Phe | Tyr | Phe 550 | Lys | Arg | Val | Pro | Lys 555 | Asn | Lys | Lys | Lys Thr 560 |
| Ile | Val | Val | Leu | Leu 565 | Asp | Glu | Leu | Asp | Ala 570 | Met | Val | Thr | Lys | Ser Gln 575 |
| Asp | Ile | Met | Tyr 580 | Asn | Phe | Phe | Asn | Trp 585 | Thr | Thr | Tyr | Glu | Asn 590 | Ala Lys |
| Leu | Ile | Val 595 | Ile | Ala | Val | Ala | Asn 600 | Thr | Met | Asp | Leu | Pro 605 | Glu | Arg Gln |
| Leu | Gly 610 | Asn | Lys | Ile | Thr | Ser 615 | Arg | Ile | Gly | Phe | Thr 620 | Arg | Ile | Met Phe |
| Thr 625 | Gly | Tyr | Thr | His | Glu 630 | Glu | Leu | Lys | Asn | Ile 635 | Ile | Asp | Leu | Arg Leu 640 |
| Lys | Gly | Leu | Asn | Asp 645 | Ser | Phe | Phe | Tyr | Val 650 | Asp | Thr | Lys | Thr | Gly Asn 655 |
| Ala | Ile | Leu | Ile 660 | Asp | Ala | Ala | Gly | Asn 665 | Asp | Thr | Thr | Val | Lys 670 | Gln Thr |
| Leu | Pro | Glu 675 | Asp | Val | Arg | Lys | Val 680 | Arg | Leu | Arg | Met | Ser 685 | Ala | Asp Ala |
| Ile | Glu 690 | Ile | Ala | Ser | Arg | Lys 695 | Val | Ala | Ser | Val | Ser 700 | Gly | Asp | Ala Arg |
| Arg 705 | Ala | Leu | Lys | Val | Cys 710 | Lys | Arg | Ala | Ala | Glu 715 | Ile | Ala | Glu | Lys His 720 |
| Tyr | Met | Ala | Lys | His 725 | Gly | Tyr | Gly | Tyr | Asp 730 | Gly | Lys | Thr | Val | Ile Glu 735 |
| Asp | Glu | Asn | Glu 740 | Glu | Gln | Ile | Tyr | Asp 745 | Asp | Glu | Asp | Lys | Asp 750 | Leu Ile |
| Glu | Ser | Asn 755 | Lys | Ala | Lys | Asp | Asp 760 | Asn | Asp | Asp | Asp | Asp 765 | Asp | Asn Asp |
| Gly | Val 770 | Gln | Thr | Val | His | Ile 775 | Thr | His | Val | Met | Lys 780 | Ala | Leu | Asn Glu |
| Thr 785 | Leu | Asn | Ser | His | Val 790 | Ile | Thr | Phe | Met | Thr 795 | Arg | Leu | Ser | Phe Thr 800 |
| Ala | Lys | Leu | Phe | Ile 805 | Tyr | Ala | Leu | Leu | Asn 810 | Leu | Met | Lys | Lys | Asn Gly 815 |

| Ser | Gln | Glu | Gln | Glu | Leu | Gly | Asp | Ile | Val | Asp | Glu | Ile | Lys | Leu | Leu |
|-----|-----|-----|-----|-----|-----|-----|-----|-----|-----|-----|-----|-----|-----|-----|-----|
|     |     |     | 820 |     |     |     |     | 825 |     |     |     |     | 830 |     |     |
| Ile | Glu | Val | Asn | Gly | Ser | Asn | Lys | Phe | Val | Met | Glu | Ile | Ala | Lys | Thr |
|     |     |     | 835 |     |     |     | 840 |     |     |     |     | 845 |     |     |     |
| Leu | Phe | Gln | Gln | Gly | Ser | Asp | Asn | Ile | Ser | Glu | Gln | Leu | Arg | Ile | Ile |
|     | 850 |     |     |     |     | 855 |     |     |     |     | 860 |     |     |     |     |
| Ser | Trp | Asp | Phe | Val | Leu | Asn | Gln | Leu | Leu | Asp | Ala | Gly | Ile | Leu | Phe |
| 865 |     |     |     |     | 870 |     |     |     |     | 875 |     |     |     |     | 880 |
| Lys | Gln | Thr | Met | Lys | Asn | Asp | Arg | Ile | Cys | Cys | Val | Lys | Leu | Asn | Ile |
|     |     |     |     | 885 |     |     |     |     | 890 |     |     |     |     | 895 |     |
| Ser | Val | Glu | Glu | Ala | Lys | Arg | Ala | Met | Asn | Glu | Asp | Glu | Thr | Leu | Arg |
|     |     |     | 900 |     |     |     |     | 905 |     |     |     |     | 910 |     |     |
| Asn | Leu |     |     |     |     |     |     |     |     |     |     |     |     |     |     |

( 2 ) INFORMATION FOR SEQ ID NO:3:

( i ) SEQUENCE CHARACTERISTICS:
        ( A ) LENGTH: 2809 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 807..2666

( x i ) SEQUENCE DESCRIPTION: SEQ ID NO:3:

```
GAGCTCAACA CCACCATTGA GAACGTAGAA TTTCAATTTT TAAGCTGATT CTCTTTCTGC      60

ATGAACTCTC CTAGCAATGT GAAACTTCTC TTAAGGGAAA TTTTCGCCTT TTTGAATGGG     120

CATACTTGGC CAAAAATTCA GGATTGAATA TATATAATCG AACTTGTAT GGATAAAAAT     180

TTATATCAAG AGTCTGTTTC TTAATTGGAT TTGCTGTGAT CTAGTATTGA GATGACTATA     240

AACCGGCCAG GAAATTAGTC TTTTCGAAGC TGGTTTTGGT TTCGCAAGAG TCTTTTTGAC     300

AGCTTTTTGG CCTCAATTTG TATTCCCTTA ATACGCTTCT TCAACTCTGT CTTAGAGACC     360

ATTTCTCCAG TGGCCTCATC TAGGTGTAAA CTAGCAATAG CGTCACTAGC TGCCGTGACA     420

TTAACTTGCT GTGGCACCTT TATATGTAAT ATGAACCATC TTTCAATGGA TCATAAGAAT     480

AAGTGTCGTA AAAGGCCAAA TATCCATGCA TAAATATCGA CTTATTCGCG TAAATGTGAT     540

ATGGATCAGC TAGTACCAAT TTCTAGTCTA GCAAAATCGG GAAAATTTTT CAGAACACCC     600

ACTCACCGCA TCATTGAGGT GGAAATGACA ATAGTAAGCA GAATTGTTAT TCTTCACAAT     660

GTGTAAAAGT TATAAAGAAA TAGGAACCAC CTTTAAATTA AGACAAAGTA GAATATATTA     720

GCTGAAATTG TATTTGATAA TTGATCATTG ATCTTATTTG CTATATCTTT AAAACAAGTT     780

TTTGTAGTAC TGCGAATTGC CATAAC ATG CTA AAT GGG GAA GAC TTT GTA GAG      833
                               Met Leu Asn Gly Glu Asp Phe Val Glu
                                 1                   5

CAT AAT GAT ATC CTA TCG TCT CCG GCA AAA AGC AGG AAT GTA ACC CCA       881
His Asn Asp Ile Leu Ser Ser Pro Ala Lys Ser Arg Asn Val Thr Pro
 10              15                  20                      25

AAA AGG GTT GAC CCA CAT GGA GAA AGA CAA CTG AGA AGA ATT CAT TCA       929
Lys Arg Val Asp Pro His Gly Glu Arg Gln Leu Arg Arg Ile His Ser
            30                  35                  40

TCA AAG AAG AAT TTG TTG GAA AGA ATC TCG CTT GTA GGC AAC GAA AGG       977
Ser Lys Lys Asn Leu Leu Glu Arg Ile Ser Leu Val Gly Asn Glu Arg
        45                  50                  55
```

| | | | | | | | | | | | | | | | | |
|---|---|---|---|---|---|---|---|---|---|---|---|---|---|---|---|---|
| AAA | AAT | ACA | TCT | CCA | GAT | CCG | GCA | CTC | AAA | CCT | AAA | ACG | CCA | AGT | AAA | 1025 |
| Lys | Asn | Thr | Ser | Pro | Asp | Pro | Ala | Leu | Lys | Pro | Lys | Thr | Pro | Ser | Lys | |
| | | 60 | | | | 65 | | | | | | 70 | | | | |
| GCT | CCC | CGT | AAA | CGT | GGA | AGA | CCA | AGA | AAG | ATA | CAG | GAA | GAA | TTA | ACT | 1073 |
| Ala | Pro | Arg | Lys | Arg | Gly | Arg | Pro | Arg | Lys | Ile | Gln | Glu | Glu | Leu | Thr | |
| | 75 | | | | 80 | | | | | | 85 | | | | | |
| GAT | AGG | ATC | AAG | AAG | GAT | GAG | AAA | GAT | ACA | ATT | TCC | TCT | AAG | AAA | AAG | 1121 |
| Asp | Arg | Ile | Lys | Lys | Asp | Glu | Lys | Asp | Thr | Ile | Ser | Ser | Lys | Lys | Lys | |
| 90 | | | | | 95 | | | | 100 | | | | | | 105 | |
| AGG | AAA | TTG | GAC | AAA | GAT | ACA | TCA | GGT | AAT | GTC | AAT | GAG | GAA | AGC | AAG | 1169 |
| Arg | Lys | Leu | Asp | Lys | Asp | Thr | Ser | Gly | Asn | Val | Asn | Glu | Glu | Ser | Lys | |
| | | | | 110 | | | | 115 | | | | | 120 | | | |
| ACT | TCT | AAC | AAC | AAG | CAG | GTG | ATG | GAA | AAG | ACG | GGG | ATA | AAA | GAG | AAA | 1217 |
| Thr | Ser | Asn | Asn | Lys | Gln | Val | Met | Glu | Lys | Thr | Gly | Ile | Lys | Glu | Lys | |
| | | | 125 | | | | 130 | | | | | 135 | | | | |
| AGA | GAA | CGC | GAA | AAA | ATA | CAG | GTA | GCG | ACC | ACA | ACA | TAT | GAA | GAT | AAT | 1265 |
| Arg | Glu | Arg | Glu | Lys | Ile | Gln | Val | Ala | Thr | Thr | Thr | Tyr | Glu | Asp | Asn | |
| | | 140 | | | | 145 | | | | | 150 | | | | | |
| GTG | ACT | CCA | CAA | ACT | GAT | GAT | AAT | TTT | GTA | TCA | AAT | TCA | CCC | GAG | CCA | 1313 |
| Val | Thr | Pro | Gln | Thr | Asp | Asp | Asn | Phe | Val | Ser | Asn | Ser | Pro | Glu | Pro | |
| | 155 | | | | | 160 | | | | | 165 | | | | | |
| CCA | GAA | CCT | GCA | ACA | CCA | TCT | AAG | AAG | TCT | TTA | ACC | ACT | AAT | CAT | GAT | 1361 |
| Pro | Glu | Pro | Ala | Thr | Pro | Ser | Lys | Lys | Ser | Leu | Thr | Thr | Asn | His | Asp | |
| 170 | | | | | 175 | | | | | 180 | | | | | 185 | |
| TTT | ACT | TCG | CCC | CTA | AAG | CAA | ATT | ATA | ATG | AAT | AAT | TTA | AAA | GAA | TAT | 1409 |
| Phe | Thr | Ser | Pro | Leu | Lys | Gln | Ile | Ile | Met | Asn | Asn | Leu | Lys | Glu | Tyr | |
| | | | | 190 | | | | | 195 | | | | | 200 | | |
| AAA | GAC | TCA | ACC | TCC | CCA | GGT | AAA | TTA | ACC | TTG | AGT | AGA | AAT | TTT | ACT | 1457 |
| Lys | Asp | Ser | Thr | Ser | Pro | Gly | Lys | Leu | Thr | Leu | Ser | Arg | Asn | Phe | Thr | |
| | | | 205 | | | | 210 | | | | | 215 | | | | |
| CCA | ACC | CCT | GTA | CCG | AAA | AAT | AAA | AAG | CTC | TAC | CAA | ACT | TCG | GAA | ACC | 1505 |
| Pro | Thr | Pro | Val | Pro | Lys | Asn | Lys | Lys | Leu | Tyr | Gln | Thr | Ser | Glu | Thr | |
| | | 220 | | | | 225 | | | | | 230 | | | | | |
| AAG | TCA | GCA | AGC | TCG | TTT | TTG | GAT | ACT | TTT | GAA | GGA | TAT | TTC | GAC | CAA | 1553 |
| Lys | Ser | Ala | Ser | Ser | Phe | Leu | Asp | Thr | Phe | Glu | Gly | Tyr | Phe | Asp | Gln | |
| | 235 | | | | | 240 | | | | | 245 | | | | | |
| AGA | AAA | ATT | GTC | AGA | ACT | AAT | GCG | AAG | TCA | AGG | CAC | ACC | ATG | TCA | ATG | 1601 |
| Arg | Lys | Ile | Val | Arg | Thr | Asn | Ala | Lys | Ser | Arg | His | Thr | Met | Ser | Met | |
| 250 | | | | | 255 | | | | | 260 | | | | | 265 | |
| GCA | CCT | GAC | GTT | ACC | AGA | GAA | GAG | TTT | TCC | CTA | GTA | TCA | AAC | TTT | TTC | 1649 |
| Ala | Pro | Asp | Val | Thr | Arg | Glu | Glu | Phe | Ser | Leu | Val | Ser | Asn | Phe | Phe | |
| | | | | 270 | | | | 275 | | | | | 280 | | | |
| AAC | GAA | AAT | TTT | CAA | AAA | CGT | CCC | AGG | CAA | AAG | TTA | TTT | GAA | ATT | CAG | 1697 |
| Asn | Glu | Asn | Phe | Gln | Lys | Arg | Pro | Arg | Gln | Lys | Leu | Phe | Glu | Ile | Gln | |
| | | | 285 | | | | | 290 | | | | | 295 | | | |
| AAA | AAA | ATG | TTT | CCC | CAG | TAT | TGG | TTT | GAA | TTG | ACT | CAA | GGA | TTC | TCC | 1745 |
| Lys | Lys | Met | Phe | Pro | Gln | Tyr | Trp | Phe | Glu | Leu | Thr | Gln | Gly | Phe | Ser | |
| | | 300 | | | | 305 | | | | 310 | | | | | | |
| TTA | TTA | TTT | TAT | GGT | GTA | GGT | TCG | AAA | CGT | AAT | TTT | TTG | GAA | GAG | TTT | 1793 |
| Leu | Leu | Phe | Tyr | Gly | Val | Gly | Ser | Lys | Arg | Asn | Phe | Leu | Glu | Glu | Phe | |
| | 315 | | | | 320 | | | | | 325 | | | | | | |
| GCC | ATT | GAC | TAC | TTG | TCT | CCG | AAA | ATC | GCG | TAC | TCG | CAA | CTG | GCT | TAT | 1841 |
| Ala | Ile | Asp | Tyr | Leu | Ser | Pro | Lys | Ile | Ala | Tyr | Ser | Gln | Leu | Ala | Tyr | |
| 330 | | | | | 335 | | | | | 340 | | | | | 345 | |
| GAG | AAT | GAA | TTA | CAA | CAA | AAC | AAA | CCT | GTA | AAT | TCC | ATC | CCA | TGC | CTT | 1889 |
| Glu | Asn | Glu | Leu | Gln | Gln | Asn | Lys | Pro | Val | Asn | Ser | Ile | Pro | Cys | Leu | |
| | | | | 350 | | | | | 355 | | | | | 360 | | |
| ATT | TTA | AAT | GGT | TAC | AAC | CCT | AGC | TGT | AAC | TAT | CGT | GAC | GTC | TTC | AAA | 1937 |
| Ile | Leu | Asn | Gly | Tyr | Asn | Pro | Ser | Cys | Asn | Tyr | Arg | Asp | Val | Phe | Lys | |
| | | | 365 | | | | | 370 | | | | | 375 | | | |

| | | | | | | | | | | | | | | | | |
|---|---|---|---|---|---|---|---|---|---|---|---|---|---|---|---|---|
| GAG | ATT | ACC | GAT | CTT | TTG | GTC | CCC | GCT | GAG | TTG | ACA | AGA | AGC | GAA | ACT | 1985 |
| Glu | Ile | Thr | Asp | Leu | Leu | Val | Pro | Ala | Glu | Leu | Thr | Arg | Ser | Glu | Thr | |
| | | 380 | | | | 385 | | | | | 390 | | | | | |
| AAG | TAC | TGG | GGC | AAT | CAT | GTG | ATT | TTG | CAG | ATC | CAA | AAG | ATG | ATT | GAT | 2033 |
| Lys | Tyr | Trp | Gly | Asn | His | Val | Ile | Leu | Gln | Ile | Gln | Lys | Met | Ile | Asp | |
| | 395 | | | | 400 | | | | | 405 | | | | | | |
| TTC | TAC | AAA | AAT | CAA | CCT | TTA | GAT | ATC | AAA | TTA | ATA | CTT | GTA | GTG | CAT | 2081 |
| Phe | Tyr | Lys | Asn | Gln | Pro | Leu | Asp | Ile | Lys | Leu | Ile | Leu | Val | Val | His | |
| 410 | | | | | 415 | | | | | 420 | | | | | 425 | |
| AAT | CTG | GAT | GGT | CCT | AGC | ATA | AGG | AAA | AAC | ACT | TTT | CAG | ACG | ATG | CTA | 2129 |
| Asn | Leu | Asp | Gly | Pro | Ser | Ile | Arg | Lys | Asn | Thr | Phe | Gln | Thr | Met | Leu | |
| | | | 430 | | | | | 435 | | | | | | 440 | | |
| AGC | TTC | CTC | TCC | GTC | ATC | AGA | CAA | ATC | GCC | ATA | GTC | GCC | TCT | ACA | GAC | 2177 |
| Ser | Phe | Leu | Ser | Val | Ile | Arg | Gln | Ile | Ala | Ile | Val | Ala | Ser | Thr | Asp | |
| | | | 445 | | | | | 450 | | | | | 455 | | | |
| CAC | ATT | TAC | GCT | CCG | CTC | CTC | TGG | GAC | AAC | ATG | AAG | GCC | CAA | AAC | TAC | 2225 |
| His | Ile | Tyr | Ala | Pro | Leu | Leu | Trp | Asp | Asn | Met | Lys | Ala | Gln | Asn | Tyr | |
| | | 460 | | | | | 465 | | | | | 470 | | | | |
| AAC | TTT | GTC | TTT | CAT | GAT | ATT | TCG | AAT | TTT | GAA | CCG | TCG | ACA | GTC | GAG | 2273 |
| Asn | Phe | Val | Phe | His | Asp | Ile | Ser | Asn | Phe | Glu | Pro | Ser | Thr | Val | Glu | |
| | 475 | | | | 480 | | | | | 485 | | | | | | |
| TCT | ACG | TTC | CAA | GAT | GTG | ATG | AAG | ATG | GGT | AAA | AGC | GAT | ACC | AGC | AGT | 2321 |
| Ser | Thr | Phe | Gln | Asp | Val | Met | Lys | Met | Gly | Lys | Ser | Asp | Thr | Ser | Ser | |
| 490 | | | | | 495 | | | | | 500 | | | | | 505 | |
| GGT | GCT | GAA | GGT | GCG | AAA | TAC | GTC | TTA | CAA | TCA | CTT | ACT | GTG | AAC | TCC | 2369 |
| Gly | Ala | Glu | Gly | Ala | Lys | Tyr | Val | Leu | Gln | Ser | Leu | Thr | Val | Asn | Ser | |
| | | | | 510 | | | | | 515 | | | | | 520 | | |
| AAG | AAG | ATG | TAT | AAG | TTG | CTT | ATT | GAA | ACA | CAA | ATG | CAG | AAT | ATG | GGG | 2417 |
| Lys | Lys | Met | Tyr | Lys | Leu | Leu | Ile | Glu | Thr | Gln | Met | Gln | Asn | Met | Gly | |
| | | | 525 | | | | | 530 | | | | | 535 | | | |
| AAT | CTA | TCC | GCT | AAC | ACA | GGT | CCT | AAG | CGT | GGT | ACT | CAA | AGA | ACT | GGA | 2465 |
| Asn | Leu | Ser | Ala | Asn | Thr | Gly | Pro | Lys | Arg | Gly | Thr | Gln | Arg | Thr | Gly | |
| | | 540 | | | | | 545 | | | | | 550 | | | | |
| GTA | GAA | CTT | AAA | CTT | TTC | AAC | CAT | CTC | TGT | GCC | GCT | GAT | TTT | ATT | GCT | 2513 |
| Val | Glu | Leu | Lys | Leu | Phe | Asn | His | Leu | Cys | Ala | Ala | Asp | Phe | Ile | Ala | |
| | 555 | | | | | 560 | | | | | 565 | | | | | |
| TCT | AAT | GAG | ATA | GCT | CTA | AGG | TCG | ATG | CTT | AGA | GAA | TTC | ATA | GAA | CAT | 2561 |
| Ser | Asn | Glu | Ile | Ala | Leu | Arg | Ser | Met | Leu | Arg | Glu | Phe | Ile | Glu | His | |
| 570 | | | | | 575 | | | | | 580 | | | | | 585 | |
| AAA | ATG | GCC | AAC | ATA | ACT | AAG | AAC | AAT | TCT | GGA | ATG | GAA | ATT | ATT | TGG | 2609 |
| Lys | Met | Ala | Asn | Ile | Thr | Lys | Asn | Asn | Ser | Gly | Met | Glu | Ile | Ile | Trp | |
| | | | | 590 | | | | | 595 | | | | | 600 | | |
| GTA | CCC | TAC | ACG | TAT | GCG | GAA | CTT | GAA | AAA | CTT | CTG | AAA | ACC | GTT | TTA | 2657 |
| Val | Pro | Tyr | Thr | Tyr | Ala | Glu | Leu | Glu | Lys | Leu | Leu | Lys | Thr | Val | Leu | |
| | | | 605 | | | | | 610 | | | | | 615 | | | |
| AAT | ACT | CTA | TAAATGTATA | CATATCACGA | ACAATTGTAA | TAGTACTAGG | | | | | | | | | | 2706 |
| Asn | Thr | Leu | | | | | | | | | | | | | | |
| | | 620 | | | | | | | | | | | | | | |

CTTGCTAGCT TTGCTTTCCC ATAACCAACA ATACTTAGTG ATGTATCTTA AAACGACTAA 2766

AAAACTTCTC ATATAACCCT ACTGAAAAAC GTCTGATGAG CTC 2809

( 2 ) INFORMATION FOR SEQ ID NO:4:

( i ) SEQUENCE CHARACTERISTICS:
        ( A ) LENGTH: 620 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Leu | Asn | Gly | Glu | Asp | Phe | Val | Glu | His | Asn | Asp | Ile | Leu | Ser | Ser |
| 1 | | | | 5 | | | | | 10 | | | | | 15 | |
| Pro | Ala | Lys | Ser | Arg | Asn | Val | Thr | Pro | Lys | Arg | Val | Asp | Pro | His | Gly |
| | | | 20 | | | | | 25 | | | | | 30 | | |
| Glu | Arg | Gln | Leu | Arg | Arg | Ile | His | Ser | Ser | Lys | Lys | Asn | Leu | Leu | Glu |
| | | | 35 | | | | | 40 | | | | | 45 | | |
| Arg | Ile | Ser | Leu | Val | Gly | Asn | Glu | Arg | Lys | Asn | Thr | Ser | Pro | Asp | Pro |
| | | 50 | | | | | 55 | | | | | 60 | | | |
| Ala | Leu | Lys | Pro | Lys | Thr | Pro | Ser | Lys | Ala | Pro | Arg | Lys | Arg | Gly | Arg |
| 65 | | | | | 70 | | | | | 75 | | | | | 80 |
| Pro | Arg | Lys | Ile | Gln | Glu | Glu | Leu | Thr | Asp | Arg | Ile | Lys | Lys | Asp | Glu |
| | | | | 85 | | | | | 90 | | | | | 95 | |
| Lys | Asp | Thr | Ile | Ser | Ser | Lys | Lys | Arg | Lys | Leu | Asp | Lys | Asp | Thr | |
| | | | 100 | | | | | 105 | | | | | 110 | | |
| Ser | Gly | Asn | Val | Asn | Glu | Glu | Ser | Lys | Thr | Ser | Asn | Asn | Lys | Gln | Val |
| | | | 115 | | | | | 120 | | | | | 125 | | |
| Met | Glu | Lys | Thr | Gly | Ile | Lys | Glu | Lys | Arg | Glu | Arg | Glu | Lys | Ile | Gln |
| | 130 | | | | | 135 | | | | | 140 | | | | |
| Val | Ala | Thr | Thr | Thr | Tyr | Glu | Asp | Asn | Val | Thr | Pro | Gln | Thr | Asp | Asp |
| 145 | | | | | 150 | | | | | 155 | | | | | 160 |
| Asn | Phe | Val | Ser | Asn | Ser | Pro | Glu | Pro | Glu | Pro | Ala | Thr | Pro | Ser | |
| | | | | 165 | | | | | 170 | | | | | 175 | |
| Lys | Lys | Ser | Leu | Thr | Thr | Asn | His | Asp | Phe | Thr | Ser | Pro | Leu | Lys | Gln |
| | | | | 180 | | | | | 185 | | | | | 190 | |
| Ile | Ile | Met | Asn | Asn | Leu | Lys | Glu | Tyr | Lys | Asp | Ser | Thr | Ser | Pro | Gly |
| | | | 195 | | | | | 200 | | | | | 205 | | |
| Lys | Leu | Thr | Leu | Ser | Arg | Asn | Phe | Thr | Pro | Thr | Pro | Val | Pro | Lys | Asn |
| | | 210 | | | | | 215 | | | | | 220 | | | |
| Lys | Lys | Leu | Tyr | Gln | Thr | Ser | Glu | Thr | Lys | Ser | Ala | Ser | Ser | Phe | Leu |
| 225 | | | | | 230 | | | | | 235 | | | | | 240 |
| Asp | Thr | Phe | Glu | Gly | Tyr | Phe | Asp | Gln | Arg | Lys | Ile | Val | Arg | Thr | Asn |
| | | | | 245 | | | | | 250 | | | | | 255 | |
| Ala | Lys | Ser | Arg | His | Thr | Met | Ser | Met | Ala | Pro | Asp | Val | Thr | Arg | Glu |
| | | | 260 | | | | | 265 | | | | | 270 | | |
| Glu | Phe | Ser | Leu | Val | Ser | Asn | Phe | Phe | Asn | Glu | Asn | Phe | Gln | Lys | Arg |
| | | 275 | | | | | 280 | | | | | 285 | | | |
| Pro | Arg | Gln | Lys | Leu | Phe | Glu | Ile | Gln | Lys | Lys | Met | Phe | Pro | Gln | Tyr |
| | | 290 | | | | | 295 | | | | | 300 | | | |
| Trp | Phe | Glu | Leu | Thr | Gln | Gly | Phe | Ser | Leu | Leu | Phe | Tyr | Gly | Val | Gly |
| 305 | | | | | 310 | | | | | 315 | | | | | 320 |
| Ser | Lys | Arg | Asn | Phe | Leu | Glu | Glu | Phe | Ala | Ile | Asp | Tyr | Leu | Ser | Pro |
| | | | | 325 | | | | | 330 | | | | | 335 | |
| Lys | Ile | Ala | Tyr | Ser | Gln | Leu | Ala | Tyr | Glu | Asn | Glu | Leu | Gln | Gln | Asn |
| | | | 340 | | | | | 345 | | | | | 350 | | |
| Lys | Pro | Val | Asn | Ser | Ile | Pro | Cys | Leu | Ile | Leu | Asn | Gly | Tyr | Asn | Pro |
| | | | 355 | | | | | 360 | | | | | 365 | | |
| Ser | Cys | Asn | Tyr | Arg | Asp | Val | Phe | Lys | Glu | Ile | Thr | Asp | Leu | Leu | Val |
| | 370 | | | | | 375 | | | | | 380 | | | | |
| Pro | Ala | Glu | Leu | Thr | Arg | Ser | Glu | Thr | Lys | Tyr | Trp | Gly | Asn | His | Val |
| 385 | | | | | 390 | | | | | 395 | | | | | 400 |
| Ile | Leu | Gln | Ile | Gln | Lys | Met | Ile | Asp | Phe | Tyr | Lys | Asn | Gln | Pro | Leu |
| | | | | 405 | | | | | 410 | | | | | 415 | |
| Asp | Ile | Lys | Leu | Ile | Leu | Val | Val | His | Asn | Leu | Asp | Gly | Pro | Ser | Ile |
| | | | 420 | | | | | 425 | | | | | 430 | | |

| | | | | | | | | | | | | | | |
|---|---|---|---|---|---|---|---|---|---|---|---|---|---|---|
|Arg|Lys|Asn|Thr|Phe|Gln|Thr|Met|Leu|Ser|Phe|Leu|Ser|Val|Ile|Arg|
| | |435| | | | |440| | | | |445| | | |
|Gln|Ile|Ala|Ile|Val|Ala|Ser|Thr|Asp|His|Ile|Tyr|Ala|Pro|Leu|Leu|
| |450| | | | |455| | | | |460| | | | |
|Trp|Asp|Asn|Met|Lys|Ala|Gln|Asn|Tyr|Asn|Phe|Val|Phe|His|Asp|Ile|
|465| | | |470| | | | |475| | | | |480| |
|Ser|Asn|Phe|Glu|Pro|Ser|Thr|Val|Glu|Ser|Thr|Phe|Gln|Asp|Val|Met|
| | | |485| | | | |490| | | | |495| | |
|Lys|Met|Gly|Lys|Ser|Asp|Thr|Ser|Ser|Gly|Ala|Glu|Gly|Ala|Lys|Tyr|
| | |500| | | | |505| | | | |510| | | |
|Val|Leu|Gln|Ser|Leu|Thr|Val|Asn|Ser|Lys|Lys|Met|Tyr|Lys|Leu|Leu|
| |515| | | | |520| | | | |525| | | | |
|Ile|Glu|Thr|Gln|Met|Gln|Asn|Met|Gly|Asn|Leu|Ser|Ala|Asn|Thr|Gly|
| |530| | | | |535| | | | |540| | | | |
|Pro|Lys|Arg|Gly|Thr|Gln|Arg|Thr|Gly|Val|Glu|Leu|Lys|Leu|Phe|Asn|
|545| | | |550| | | | |555| | | | |560| |
|His|Leu|Cys|Ala|Ala|Asp|Phe|Ile|Ala|Ser|Asn|Glu|Ile|Ala|Leu|Arg|
| | | |565| | | | |570| | | | |575| | |
|Ser|Met|Leu|Arg|Glu|Phe|Ile|Glu|His|Lys|Met|Ala|Asn|Ile|Thr|Lys|
| | |580| | | | |585| | | | |590| | | |
|Asn|Asn|Ser|Gly|Met|Glu|Ile|Ile|Trp|Val|Pro|Tyr|Thr|Tyr|Ala|Glu|
| |595| | | | |600| | | | |605| | | | |
|Leu|Glu|Lys|Leu|Leu|Lys|Thr|Val|Leu|Asn|Thr|Leu| | | | |
| |610| | | | |615| | | | |620| | | | |

( 2 ) INFORMATION FOR SEQ ID NO:5:

( i ) SEQUENCE CHARACTERISTICS:
  ( A ) LENGTH: 2700 base pairs
  ( B ) TYPE: nucleic acid
  ( C ) STRANDEDNESS: double
  ( D ) TOPOLOGY: linear ( i i ) MOLECULE TYPE: cDNA ( x i ) SEQUENCE DESCRIPTION: SEQ ID NO:5:

| | | | | | | |
|---|---|---|---|---|---|---|
|TCTGAAATAA|AAAGTACAAA|AAAGAAAACA|ATATACCAGA|TATGAACCCT|TTTAGTGAGA|60|
|TTCCAGCATG|TCTTTGCGCA|GATCCAAATC|TTTCTTTGTC|TTGAAATTTA|TTCAGTAAAT|120|
|TAAAAGTCAG|TTCTTTAGTA|GCATTCATCT|TCTTGGTAAG|TCTTTTTCTT|GTTTTTGAAA|180|
|AGAGTTCCT|GAAGTTTGTC|TACTGTGAAT|ATACTTGCA|CATTTGTTTA|ATTTTTAAAC|240|
|ACGCTATAAT|TTGTGTCATA|AAGAATTTTT|TGTAGAATAG|CTTTTTTTTT|AATAGGAAAA|300|
|AAAAATAAAA|AAAGGTGGAA|AAGACAATCT|TTTCCAGAAA|CTTGAAACTA|TACTGGAGAT|360|
|GAAGGGTTGT|CGTTGGTTGC|GTTACGAGAC|AGGCTTGACA|ATTTCACAAG|AGTAATGTTT|420|
|CATTACCTGC|TGTTTTATTA|TCTTTATATT|TAGTAAGACC|AGCAGAAACG|CTACACGTGA|480|
|TGATAATGGA|ACTAAGCATT|CTGTTAGATG|GTAAGAATTT|TTTTTACCTT|CCATTACCAC|540|
|TAACGCCTTT|TTTAGTGTCT|TTTTGATATT|TACTGACGTA|TTTTTCCGCA|CCGTAATTTG|600|
|AAGAAAAAGA|AAAGTGACAA|AAGATGGCAT|TGTTTACATA|CAGAGTCGTA|GTATCACAAG|660|
|AGTAGTCCAA|CAGGATGAGC|GACCTTAACC|AATCCAAAAA|GATGAACGTC|AGCGAGTTTG|720|
|CTGACGCCCA|AAGGAGCCAC|TATACAGTAT|ACCCCAGTTT|GCCTCAAAGT|AACAAAAATG|780|
|ATAAACACAT|TCCCTTTGTC|AAACTTCTAT|CAGGCAAAGA|ATCGGAAGTG|AACGTGGAAA|840|
|AAAGATGGGA|ATTGTATCAT|CAGTTACATT|CCCACTTTCA|TGATCAAGTA|GATCATATTA|900|

| | | | | | | |
|---|---|---|---|---|---|---|
| TCGATAATAT | TGAAGCAGAC | TTGAAAGCAG | AGATTTCAGA | CCTTTTATAT | AGTGAAACTA | 960 |
| CTCAGAAAAG | GCGATGCTTT | AACACTATTT | TCCTATTAGG | TTCAGATAGT | ACGACAAAAA | 1020 |
| TTGAACTTAA | AGACGAATCT | TCTCGCTACA | ACGTTTTGAT | TGAATTGACT | CCGAAAGAAT | 1080 |
| CTCCGAATGT | AAGAATGATG | CTTCGTAGGT | CTATGTACAA | ACTTACAGC | GCAGCTGATG | 1140 |
| CAGAAGAACA | TCCAACTATC | AAGTATGAAG | ACATTAACGA | TGAAGATGGC | GATTTTACCG | 1200 |
| AGCAAACAA | TGATGTATCA | TACGATCGT | CACTTGTGGA | AAACTTCAAA | AGGCTTTTG | 1260 |
| GAAAAGACTT | AGCAATGGTA | TTTAATTTTA | AAGATGTAGA | TTCTATTAAC | TTCAACACAT | 1320 |
| TGGATAACTT | CATAATTCTA | TTGAAAAGTG | CCTTCAAGTA | TGACCATGTT | AAAATAAGTT | 1380 |
| TAATCTTTAA | TATTAATACA | AACTTGTCAA | ATATTGAGAA | AAATTTGAGA | CAATCAACCA | 1440 |
| TACGACTTCT | GAAGAGAAAT | TATCATAAAC | TAGACGTGTC | GAGTAATAAA | GGATTTAAGT | 1500 |
| ACGGAAACCA | AATCTTTCAA | AGCTTTTTGG | ATACGGTTGA | TGGCAAACTA | AATCTTTCAG | 1560 |
| ATCGTTTTGT | GGAATTCATT | CTCAGCAAGA | TGGCAAATAA | TACTAATCAC | AACTTACAAT | 1620 |
| TATTGACGAA | GATGCTGGAT | TATTCGTTGA | TGTCGTACTT | TTTCCAGAAT | GCCTTTTCAG | 1680 |
| TATTCATTGA | CCCTGTAAAT | GTTGATTTTT | TGAACGACGA | CTACTTAAAA | ATACTGAGCA | 1740 |
| GATGTCCTAC | ATTCATGTTC | TTTGTCGAAG | GTCTTATAAA | GCAGCATGCT | CCTGCTGACG | 1800 |
| AAATTCTTTC | ATTATTGACA | ACAAAAACA | GAGGCCTAGA | AGAGTTTTTT | GTTGAGTTTT | 1860 |
| TGGTAAGAGA | GAACCCGATT | AACGGGCATG | CTAAGTTTGT | TGCTCGATTC | CTCGAAGAAG | 1920 |
| AATTGAATAT | AACCAATTTT | AATCTGATAG | AATTATATCA | TAATTTGCTT | ATTGGCAAAC | 1980 |
| TAGACTCCTA | TCTAGATCGT | TGGTCAGCAT | GTAAAGAGTA | TAAGGATCGG | CTTCATTTTG | 2040 |
| AACCCATTGA | TACAATTTTT | CAAGAGCTAT | TTACTTTGGA | CAACAGAAGT | GGATTACTTA | 2100 |
| CCCAGTCGAT | TTTCCCTTCT | TACAAGTCAA | ATATCGAAGA | TAACTTACTA | AGTTGGGAGC | 2160 |
| AGGTGCTGCC | TTCGCTTGAT | AAAGAAAATT | ATGATACTCT | TTCTGGAGAT | TTGGATAAAA | 2220 |
| TAATGGCTCC | GGTACTGGGT | CAGCTATTCA | AGCTTTATCG | TGAGGCGAAT | ATGACTATCA | 2280 |
| ACATTTACGA | TTTCTACATT | GCGTTCAGAG | AAACATTACC | AAAAGAGGAA | ATATTAAATT | 2340 |
| TCATAAGAAA | AGATCCCTCC | AACACCAAAC | TCTTAGAACT | AGCAGAAACA | CCGGACGCAT | 2400 |
| TTGACAAAGT | AGCACTAATT | TTATTCATGC | AAGCAATCTT | CGCCTTTGAA | AACATGGGTC | 2460 |
| TCATTAAGTT | TCAAAGCACC | AAGAGTTACG | ATCTGGTAGA | AAAATGTGTC | TGGAGAGGAA | 2520 |
| TTTAGATAAA | GAATGCACGG | ATAAATAAGT | AAATAAATAA | CCATACATAT | ATAGAACCAT | 2580 |
| AGAACCACGT | TTTTGTAATG | AACAGTCTAC | CTGTATCTCA | TCATTTTCT | GTGTTAACTA | 2640 |
| TTATTATTAT | TATTATCGAA | TGGAGGGTAA | TATTATGTAT | AGGTAAAATA | AATAGATAGT | 2700 |

( 2 ) INFORMATION FOR SEQ ID NO:6:

( i ) SEQUENCE CHARACTERISTICS:
        ( A ) LENGTH: 615 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Met  Ser  Asp  Leu  Asn  Gln  Ser  Lys  Lys  Met  Asn  Val  Ser  Glu  Phe  Ala
 1                  5                   10                      15

Asp  Ala  Gln  Arg  Ser  His  Tyr  Thr  Val  Tyr  Pro  Ser  Leu  Pro  Gln  Ser
            20                       25                      30

Asn  Lys  Asn  Asp  Lys  His  Ile  Pro  Phe  Val  Lys  Leu  Leu  Ser  Gly  Lys
```

|       | 35  |     |     |     |     | 40  |     |     |     |     | 45  |     |     |     |     |
|-------|-----|-----|-----|-----|-----|-----|-----|-----|-----|-----|-----|-----|-----|-----|-----|
| Glu   | Ser 50 | Glu | Val | Asn | Val 55 | Glu | Lys | Arg | Trp | Glu 60 | Leu | Tyr | His | Gln | Leu |
| His 65 | Ser | His | Phe | His | Asp 70 | Gln | Val | Asp | His | Ile 75 | Ile | Asp | Asn | Ile | Glu 80 |
| Ala | Asp | Leu | Lys | Ala 85 | Glu | Ile | Ser | Asp | Leu 90 | Leu | Tyr | Ser | Glu | Thr 95 | Thr |
| Gln | Lys | Arg | Arg 100 | Cys | Phe | Asn | Thr | Ile 105 | Phe | Leu | Leu | Gly | Ser 110 | Asp | Ser |
| Thr | Thr | Lys 115 | Ile | Glu | Leu | Lys | Asp 120 | Glu | Ser | Ser | Arg | Tyr 125 | Asn | Val | Leu |
| Ile | Glu 130 | Leu | Thr | Pro | Lys | Glu 135 | Ser | Pro | Asn | Val | Arg 140 | Met | Met | Leu | Arg |
| Arg 145 | Ser | Met | Tyr | Lys | Leu 150 | Tyr | Ser | Ala | Ala | Asp 155 | Ala | Glu | Glu | His | Pro 160 |
| Thr | Ile | Lys | Tyr | Glu 165 | Asp | Ile | Asn | Asp | Glu 170 | Asp | Gly | Asp | Phe | Thr 175 | Glu |
| Gln | Asn | Asn | Asp 180 | Val | Ser | Tyr | Asp | Leu 185 | Ser | Leu | Val | Glu | Asn 190 | Phe | Lys |
| Arg | Leu | Phe 195 | Gly | Lys | Asp | Leu | Ala 200 | Met | Val | Phe | Asn | Phe 205 | Lys | Asp | Val |
| Asp | Ser 210 | Ile | Asn | Phe | Asn | Thr 215 | Leu | Asp | Asn | Phe | Ile 220 | Ile | Leu | Leu | Lys |
| Ser 225 | Ala | Phe | Lys | Tyr | Asp 230 | His | Val | Lys | Ile | Ser 235 | Leu | Ile | Phe | Asn | Ile 240 |
| Asn | Thr | Asn | Leu | Ser 245 | Asn | Ile | Glu | Lys | Asn 250 | Leu | Arg | Gln | Ser | Thr 255 | Ile |
| Arg | Leu | Leu | Lys 260 | Arg | Asn | Tyr | His | Lys 265 | Leu | Asp | Val | Ser | Ser 270 | Asn | Lys |
| Gly | Phe | Lys 275 | Tyr | Gly | Asn | Gln | Ile 280 | Phe | Gln | Ser | Phe | Leu 285 | Asp | Thr | Val |
| Asp | Gly 290 | Lys | Leu | Asn | Leu | Ser 295 | Asp | Arg | Phe | Val | Glu 300 | Phe | Ile | Leu | Ser |
| Lys 305 | Met | Ala | Asn | Asn | Thr 310 | Asn | His | Asn | Leu | Gln 315 | Leu | Leu | Thr | Lys | Met 320 |
| Leu | Asp | Tyr | Ser | Leu 325 | Met | Ser | Tyr | Phe | Phe 330 | Gln | Asn | Ala | Phe | Ser 335 | Val |
| Phe | Ile | Asp | Pro 340 | Val | Asn | Val | Asp | Phe 345 | Leu | Asn | Asp | Asp | Tyr 350 | Leu | Lys |
| Ile | Leu | Ser 355 | Arg | Cys | Pro | Thr | Phe 360 | Met | Phe | Phe | Val | Glu 365 | Gly | Leu | Ile |
| Lys | Gln 370 | His | Ala | Pro | Ala | Asp 375 | Glu | Ile | Leu | Ser | Leu 380 | Leu | Thr | Asn | Lys |
| Asn 385 | Arg | Gly | Leu | Glu | Glu 390 | Phe | Phe | Val | Glu | Phe 395 | Leu | Val | Arg | Glu | Asn 400 |
| Pro | Ile | Asn | Gly | His 405 | Ala | Lys | Phe | Val | Ala 410 | Arg | Phe | Leu | Glu | Glu 415 | Glu |
| Leu | Asn | Ile | Thr 420 | Asn | Phe | Asn | Leu | Ile 425 | Glu | Leu | Tyr | His | Asn 430 | Leu | Leu |
| Ile | Gly | Lys 435 | Leu | Asp | Ser | Tyr | Leu 440 | Asp | Arg | Trp | Ser | Ala 445 | Cys | Lys | Glu |
| Tyr | Lys 450 | Asp | Arg | Leu | His | Phe 455 | Glu | Pro | Ile | Asp | Thr 460 | Ile | Phe | Gln | Glu |

| | | | | | | | | | | | | | | | |
|---|---|---|---|---|---|---|---|---|---|---|---|---|---|---|---|
| Leu | Phe | Thr | Leu | Asp | Asn | Arg | Ser | Gly | Leu | Leu | Thr | Gln | Ser | Ile | Phe |
| 465 | | | | | 470 | | | | | 475 | | | | | 480 |
| Pro | Ser | Tyr | Lys | Ser | Asn | Ile | Glu | Asp | Asn | Leu | Leu | Ser | Trp | Glu | Gln |
| | | | | 485 | | | | | 490 | | | | | 495 | |
| Val | Leu | Pro | Ser | Leu | Asp | Lys | Glu | Asn | Tyr | Asp | Thr | Leu | Ser | Gly | Asp |
| | | | 500 | | | | | 505 | | | | | 510 | | |
| Leu | Asp | Lys | Ile | Met | Ala | Pro | Val | Leu | Gly | Gln | Leu | Phe | Lys | Leu | Tyr |
| | | 515 | | | | | 520 | | | | | 525 | | | |
| Arg | Glu | Ala | Asn | Met | Thr | Ile | Asn | Ile | Tyr | Asp | Phe | Tyr | Ile | Ala | Phe |
| | 530 | | | | | 535 | | | | | 540 | | | | |
| Arg | Glu | Thr | Leu | Pro | Lys | Glu | Glu | Ile | Leu | Asn | Phe | Ile | Arg | Lys | Asp |
| 545 | | | | | 550 | | | | | 555 | | | | | 560 |
| Pro | Ser | Asn | Thr | Lys | Leu | Leu | Glu | Leu | Ala | Glu | Thr | Pro | Asp | Ala | Phe |
| | | | | 565 | | | | | 570 | | | | | 575 | |
| Asp | Lys | Val | Ala | Leu | Ile | Leu | Phe | Met | Gln | Ala | Ile | Phe | Ala | Phe | Glu |
| | | | 580 | | | | | 585 | | | | | 590 | | |
| Asn | Met | Gly | Leu | Ile | Lys | Phe | Gln | Ser | Thr | Lys | Ser | Tyr | Asp | Leu | Val |
| | | 595 | | | | | 600 | | | | | 605 | | | |
| Glu | Lys | Cys | Val | Trp | Arg | Gly | | | | | | | | | |
| 610 | | | | | | 615 | | | | | | | | | |

( 2 ) INFORMATION FOR SEQ ID NO:7:

( i ) SEQUENCE CHARACTERISTICS:
( A ) LENGTH: 2404 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:7:

| | | | | | |
|---|---|---|---|---|---|
| CTCGAGGCCA | CCAAGAAGAG | AAAGAGAAGA | GCCAGATATT | GACTGGAGTG | CAGCCAGAGG | 60 |
| TTCCAACTTC | CAAAGCTCCT | CGGAGCCACC | AAGAAGAGAA | AGAGAAAAGG | AAGAACCAGC | 120 |
| TTTGGATTGG | GGTGCTGCCA | GAGGTGCTCA | GTTTGGTAAG | CCTCAACAAA | CCAAAAATAC | 180 |
| CTACAAGGAT | AGGTCTCTAA | CTAACAAAAA | GACTACTGAT | GAGCAACCAA | AAATCCAGAA | 240 |
| GTCTGTTTAT | GATGTTTTAC | GTACTGAAGA | TGATGATGAA | GATGAAGAGG | CTGAAAAGCA | 300 |
| AAATGGAGAC | GCAAAAGAAA | ACAAAGTTGA | TGCGGCAGTT | GAAAAGCTAC | AGGATAAAAC | 360 |
| TGCTCAATTG | ACTGTTGAAG | ATGGTGACAA | TTGGGAAGTT | GTTGGTAAGA | AATAGAGTGT | 420 |
| TGTATGATGA | TAAAATGTAC | ATTTGTATTT | ACTGTTTGCT | TTTTTTCTTT | CTTGTTTTTC | 480 |
| TACTCTCCTT | TCTACCAGGT | ATTCTAACTC | TATTATATAA | TTAAAAAAAA | AATAACCATA | 540 |
| TATTTTGTAT | TAAGTTTCAT | ACATGTGTTC | AAGTGTATTT | TTGGATTTAT | CATTTTTCTA | 600 |
| TGTGAGGTAA | GTTTTTGAAT | GTCCCATTTT | CCTTTCGTTT | TTGGAAAGTT | CTAAGAAAAA | 660 |
| GCATTAACAA | TTAAAAAAAA | AAAAAAAATC | TAAATAATAC | TGATAGAAAT | ATCAAATATA | 720 |
| AACTACTAAT | ATCGGTAATA | TTCAAAAGAA | GAAGCATGAC | TATAAGCGAA | GCTCGTCTAT | 780 |
| CACCGCAAGT | CAATCTTCTC | CCAATAAAGA | GGCACTCAAA | CGAAGAGGTA | GAGGAGACTG | 840 |
| CAGCGATTCT | AAAAAAGCGT | ACTATAGATA | ATGAAAGTG | TAAAGACAGC | GACCCTGGTT | 900 |
| TTGGTTCCCT | TCAAAGAAGG | TTACTGCAGC | AACTTTATGG | CACACTTCCT | ACGGACGAAA | 960 |
| AGATAATCTT | CACATATTTA | CAAGATTGTC | AACAAGAGAT | CGATAGAATC | ATTAAACAAT | 1020 |
| CCATTATTCA | GAAAGAGAGT | CATTCAGTAA | TTCTCGTGGG | GCCCAGACAA | AGTTACAAAA | 1080 |
| CATACTTATT | AGACTATGAA | CTGTCTTTGT | TGCAACAATC | TTATAAAGAG | CAGTTTATAA | 1140 |

| | | | | | |
|---|---|---|---|---|---|
| CTATCAGGTT | GAATGGGTTT | ATTCACTCCG | AACAAACAGC | TATTAACGGT | ATAGCAACTC | 1200 |
| AATTGGAACA | GCAGTTGCAG | AAAATTCATG | GCAGTGAAGA | AAAAATTGAC | GATACTTCAT | 1260 |
| TAGAGACTAT | TAGCAGTGGT | TCTTTGACAG | AAGTGTTTGA | GAAAATTCTT | TTACTCTTAG | 1320 |
| ATTCGACCAC | GAAGACAAGA | AATGAAGATA | GTGGTGAGGT | TGACAGAGAG | AGTATAACAA | 1380 |
| AGATAACAGT | TGTTTTTATA | TTCGATGAAA | TTGATACATT | TGCTGGGCCT | GTGAGGCAAA | 1440 |
| CTTTATTATA | CAATCTTTTT | GACATGGTAG | AACATTCTCG | GGTACCTGTT | TGCATTTTTG | 1500 |
| GCTGCACAAC | GAAATTAAAT | ATCTTGGAAT | ATTTAGAAAA | GAGGGTAAAG | AGTAGATTTT | 1560 |
| CTCAAAGAGT | GATTTATATG | CCGCAAATAC | AGAATCTAGA | CGATATGGTT | GACGCCGTCA | 1620 |
| GAAATTTACT | TACAGTTCGC | TCTGAAATCT | CCCCCTGGGT | TTCACAATGG | AATGAAACGT | 1680 |
| TGGAAAAAGA | ACTATCCGAC | CCTCGATCGA | ATTTGAATAG | ACATATTAGG | ATGAATTTCG | 1740 |
| AAACCTTTAG | GTCATTACCT | ACATTGAAAA | ATAGCATAAT | TCCATTAGTA | GCGACATCCA | 1800 |
| AAAATTTTGG | TTCACTCTGC | ACTGCCATAA | AATCGTGTTC | TTTTCTTGAC | ATATACAATA | 1860 |
| AGAACCAACT | ATCTAATAAT | TTAACAGGAA | GGCTCCAATC | TTTATCCGAT | TTAGAGTTAG | 1920 |
| CCATTTTGAT | CTCAGCCGCT | AGGGTTGCCT | TAAGGGCGAA | AGACGGATCT | TTTAATTTTA | 1980 |
| ATTTAGCTTA | TGCAGAGTAT | GAAAAGATGA | TTAAAGCTAT | CAACTCCAGA | ATTCCCACCG | 2040 |
| TGGCTCCTAC | TACAAATGTG | GGAACAGGTC | AAAGTACTTT | TTCTATCGAC | AATACTATCA | 2100 |
| AACTATGGTT | GAAAAAGGAC | GTCAAGAACG | TTTGGGAAAA | TTTAGTGCAA | CTGGATTTTT | 2160 |
| TTACCGAGAA | ATCAGCCGTT | GGTTTGAGAG | ATAATGCGAC | CGCAGCATTT | TACGCTAGCA | 2220 |
| ATTATCAATT | TCAGGGCACC | ATGATCCCGT | TTGACTTGAG | AAGTTACCAG | ATGCAGATCA | 2280 |
| TTCTTCAGGA | ATTAAGAAGA | ATTATCCCCA | AATCTAATAT | GTACTACTCC | TGGACACAAC | 2340 |
| TGTGAATCTT | GGGAACAATA | TACAGACATT | TTATTGGCGG | TAGCAACTCT | GATATTCCAC | 2400 |
| TGTT | | | | | | 2404 |

( 2 ) INFORMATION FOR SEQ ID NO:8:

( i ) SEQUENCE CHARACTERISTICS:
        ( A ) LENGTH: 529 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Met Thr Ile Ser Glu Ala Arg Leu Ser Pro Gln Val Asn Leu Leu Pro
 1               5                  10                  15

Ile Lys Arg His Ser Asn Glu Glu Val Glu Glu Thr Ala Ala Ile Leu
                20                  25                  30

Lys Lys Arg Thr Ile Asp Asn Glu Lys Cys Lys Asp Ser Asp Pro Gly
            35                  40                  45

Phe Gly Ser Leu Gln Arg Arg Leu Leu Gln Gln Leu Tyr Gly Thr Leu
 50                  55                  60

Pro Thr Asp Glu Lys Ile Ile Phe Thr Tyr Leu Gln Asp Cys Gln Gln
65                  70                  75                  80

Glu Ile Asp Arg Ile Ile Lys Gln Ser Ile Ile Gln Lys Glu Ser His
                85                  90                  95

Ser Val Ile Leu Val Gly Pro Arg Gln Ser Tyr Lys Thr Tyr Leu Leu
                100                 105                 110

Asp Tyr Glu Leu Ser Leu Leu Gln Gln Ser Tyr Lys Glu Gln Phe Ile
```

```
                    115                         120                         125
Thr  Ile  Arg  Leu  Asn  Gly  Phe  Ile  His  Ser  Glu  Gln  Thr  Ala  Ile  Asn
     130                        135                        140
Gly  Ile  Ala  Thr  Gln  Leu  Glu  Gln  Gln  Leu  Gln  Lys  Ile  His  Gly  Ser
145                        150                        155                        160
Glu  Glu  Lys  Ile  Asp  Asp  Thr  Ser  Leu  Glu  Thr  Ile  Ser  Ser  Gly  Ser
                    165                        170                        175
Leu  Thr  Glu  Val  Phe  Glu  Lys  Ile  Leu  Leu  Leu  Asp  Ser  Thr  Thr
                    180                        185                        190
Lys  Thr  Arg  Asn  Glu  Asp  Ser  Gly  Glu  Val  Asp  Arg  Glu  Ser  Ile  Thr
               195                        200                        205
Lys  Ile  Thr  Val  Val  Phe  Ile  Phe  Asp  Glu  Ile  Asp  Thr  Phe  Ala  Gly
     210                        215                        220
Pro  Val  Arg  Gln  Thr  Leu  Leu  Tyr  Asn  Leu  Phe  Asp  Met  Val  Glu  His
225                        230                        235                        240
Ser  Arg  Val  Pro  Val  Cys  Ile  Phe  Gly  Cys  Thr  Thr  Lys  Leu  Asn  Ile
                    245                        250                        255
Leu  Glu  Tyr  Leu  Glu  Lys  Arg  Val  Lys  Ser  Arg  Phe  Ser  Gln  Arg  Val
                    260                        265                        270
Ile  Tyr  Met  Pro  Gln  Ile  Gln  Asn  Leu  Asp  Asp  Met  Val  Asp  Ala  Val
               275                        280                        285
Arg  Asn  Leu  Leu  Thr  Val  Arg  Ser  Glu  Ile  Ser  Pro  Trp  Val  Ser  Gln
     290                        295                        300
Trp  Asn  Glu  Thr  Leu  Glu  Lys  Glu  Leu  Ser  Asp  Pro  Arg  Ser  Asn  Leu
305                        310                        315                        320
Asn  Arg  His  Ile  Arg  Met  Asn  Phe  Glu  Thr  Phe  Arg  Ser  Leu  Pro  Thr
                    325                        330                        335
Leu  Lys  Asn  Ser  Ile  Ile  Pro  Leu  Val  Ala  Thr  Ser  Lys  Asn  Phe  Gly
                    340                        345                        350
Ser  Leu  Cys  Thr  Ala  Ile  Lys  Ser  Cys  Ser  Phe  Leu  Asp  Ile  Tyr  Asn
               355                        360                        365
Lys  Asn  Gln  Leu  Ser  Asn  Asn  Leu  Thr  Gly  Arg  Leu  Gln  Ser  Leu  Ser
     370                        375                        380
Asp  Leu  Glu  Leu  Ala  Ile  Leu  Ile  Ser  Ala  Ala  Arg  Val  Ala  Leu  Arg
385                        390                        395                        400
Ala  Lys  Asp  Gly  Ser  Phe  Asn  Phe  Asn  Leu  Ala  Tyr  Ala  Glu  Tyr  Glu
                    405                        410                        415
Lys  Met  Ile  Lys  Ala  Ile  Asn  Ser  Arg  Ile  Pro  Thr  Val  Ala  Pro  Thr
                    420                        425                        430
Thr  Asn  Val  Gly  Thr  Gly  Gln  Ser  Thr  Phe  Ser  Ile  Asp  Asn  Thr  Ile
               435                        440                        445
Lys  Leu  Trp  Leu  Lys  Lys  Asp  Val  Lys  Asn  Val  Trp  Glu  Asn  Leu  Val
     450                        455                        460
Gln  Leu  Asp  Phe  Phe  Thr  Glu  Lys  Ser  Ala  Val  Gly  Leu  Arg  Asp  Asn
465                        470                        475                        480
Ala  Thr  Ala  Ala  Phe  Tyr  Ala  Ser  Asn  Tyr  Gln  Phe  Gln  Gly  Thr  Met
                    485                        490                        495
Ile  Pro  Phe  Asp  Leu  Arg  Ser  Tyr  Gln  Met  Gln  Ile  Ile  Leu  Gln  Glu
               500                        505                        510
Leu  Arg  Arg  Ile  Ile  Pro  Lys  Ser  Asn  Met  Tyr  Tyr  Ser  Trp  Thr  Gln
     515                        520                        525
Leu
```

( 2 ) INFORMATION FOR SEQ ID NO:9:

( i ) SEQUENCE CHARACTERISTICS:
        ( A ) LENGTH: 2306 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:9:

```
GCTATTTTTT  CATGCGTCAG  ATGTCACAAA  GCCTTTAATC  AAGTATTGTT  GCAAGAACAC    60
CTGATTCAAA  AACTACGTTC  TGATATCGAA  TCCTATTTAA  TTCAAGATTT  GAGATGCTCC   120
AGATGTCATA  AAGTGAAACG  TGACTATATG  AGTGCCCACT  GTCCATGTGC  CGGCGCGTGG   180
GAAGGAACTC  TCCCCAGAGA  AAGCATTGTT  CAAAAGTTAA  ATGTGTTTAA  GCAAGTAGCC   240
AAGTATTACG  GTTTTGATAT  ATTATTGAGT  TGTATTGCTG  ATTTGACCAT  ATGAGTAAGC   300
AGTATATAAC  GCGAGGTTCA  ATGGCCTCTT  TACCATGAAA  AAAAAAAAA   AAAAAAAAA   360
AAGGTAAGGA  AAAAGAGTAT  TTTCAATTCG  TTTCTGAACA  TATAAATATA  AATAACCGAA   420
AAATTAGCCC  TTGAACATAA  TTAACACTCT  TCTTTGATAT  TTAAATCACA  AGTACTTTTC   480
TTTTATTTTC  TTCTTAATAC  TTTTGGAAAT  AAAATGAATG  TGACCACTCC  GGAAGTTGCT   540
TTTAGGGAAT  ATCAAACCAA  CTGTCTCGCA  TCGTATATTT  CTGCTGATCC  AGACATAACT   600
CCTTCAAATT  TAATCTTGCA  AGGTTATAGT  GGAACAGGAA  AAACCTACAC  TTTGAAGAAG   660
TATTTTAATG  CGAATCCAAA  TTTGCATGCA  GTATGGCTGG  AACCTGTTGA  GTTGGTTTCT   720
TGGAAGCCCT  TACTGCAGGC  GATAGCACGT  ACTGTACAAT  ATAAATTGAA  AACCCTATAT   780
CCAAACATTC  CCACCACAGA  TTACGATCCT  TTACAGGTTG  AAGAGCCATT  TCTTTTGGTA   840
AAGACGTTGC  ACAATATTTT  TGTCCAATAT  GAATCTTTGC  AAGAAAAGAC  TTGCTTGTTC   900
TTGATATTGG  ATGGTTTCGA  TAGTTTACAA  GATTTAGACG  CCGCACTGTT  TAACAAATAT   960
ATCAAACTAA  ATGAATTACT  TCCAAAAGAT  TCTAAAATTA  ATATAAAATT  CATTTACACG  1020
ATGTTAGAGA  CATCATTTTT  GCAAAGATAT  TCTACACATT  GCATTCCAAC  TGTTATGTTT  1080
CCGAGGTATA  ATGTGGACGA  AGTTTCTACT  ATATTAGTGA  TGTCTAGATG  TGGCGAACTC  1140
ATGGAAGATT  CTTGTCTACG  TAAGCGTATC  ATTGAAGAGC  AGATAACGGA  CTGTACAGAC  1200
GATCAATTTC  AAAATGTAGC  TGCGAACTTC  ATTCACTTAA  TTGTGCAGGC  TTTTCATTCT  1260
TATACTGGAA  ACGACATATT  CGCATTGAAT  GACTTGATAG  ACTTCAAATG  GCCCAAGTAT  1320
GTATCTCGCA  TTACTAAGGA  AAACATATTT  GAACCACTGG  CTCTTTACAA  AAGTGCCATC  1380
AAACTATTTT  TAAGCACAGA  TGATAATTTA  AGTGAAAATG  GACAAGGTGA  AAGCGCGATA  1440
ACCACAAATC  GTGATGACCT  TGAGAACAGT  CAAACTTACG  ACTTATCAAT  AATTTCGAAG  1500
TATCTGCTCA  TAGCCTCATA  TATTTGTTCA  TATCTGGAAC  CTAGATACGA  TGCGAGTATT  1560
TTCTCTAGGA  AAACACGTAT  CATACAAGGT  AGAGCTGCTT  ATGGACGAAG  AAAGAAGAAA  1620
GAAGTTAACC  CTAGATATTT  ACAGCCTTCT  TTATTTGCTA  TTGAAAGACT  TTTGGCTATT  1680
TTCCAAGCTA  TATTCCCTAT  TCAAGGTAAG  GCGGAGAGTG  GTTCCCTATC  TGCACTTCGT  1740
GAGGAATCCT  TAATGAAAGC  GAATATCGAG  GTTTTTCAAA  ATTTATCCGA  ATTGCATACA  1800
TTGAAATTAA  TAGCTACAAC  CATGAACAAG  AATATCGACT  ATTTGAGTCC  TAAAGTCAGG  1860
TGGAAAGTAA  ACGTTCCCTG  GGAAATTATT  AAAGAAATAT  CAGAATCTGT  TCATTTCAAT  1920
ATCAGCGATT  ACTTCAGCGA  TATTCACGAA  TGATTATCTC  CCTGGAAGGT  ATCCAGAGGG  1980
CAGGATACGT  TCGAAACAAC  AACTACGTTA  TATAAATATT  TATACATAGT  GGGATAGAAT  2040
```

-continued

```
GAACAATTAT CAAGTAAACC TTGTATTTTT TGTTCCCACG CTCTACGCTC TGTTTCTTGG    2100

ATATGGTAAT CAAAGATTAA TACGTATAAC CGTTATTAAT TCAGTCCACT AGAAACTATT    2160

AAAAGCGCCC TACTGTATGG AAAAACAATG AATGAGGAGA CTGAACGGCG CAAAATTGTT    2220

AGTTTAGTTG CTCTTTTTGG CGGCCGGCGA TAATGTTCTT CACTTGGTAT TCTTACCAGG    2280

ATTGAGCCTG ATTTGTTTT GTCTTA                                         2306
```

( 2 ) INFORMATION FOR SEQ ID NO:10:

( i ) SEQUENCE CHARACTERISTICS:
        ( A ) LENGTH: 479 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

```
Met Asn Val Thr Thr Pro Glu Val Ala Phe Arg Glu Tyr Gln Thr Asn
1               5                   10                  15

Cys Leu Ala Ser Tyr Ile Ser Ala Asp Pro Asp Ile Thr Pro Ser Asn
            20                  25                  30

Leu Ile Leu Gln Gly Tyr Ser Gly Thr Gly Lys Thr Tyr Thr Leu Lys
        35                  40                  45

Lys Tyr Phe Asn Ala Asn Pro Asn Leu His Ala Val Trp Leu Glu Pro
50                  55                  60

Val Glu Leu Val Ser Trp Lys Pro Leu Leu Gln Ala Ile Ala Arg Thr
65                  70                  75                  80

Val Gln Tyr Lys Leu Lys Thr Leu Tyr Pro Asn Ile Pro Thr Thr Asp
                85                  90                  95

Tyr Asp Pro Leu Gln Val Glu Glu Pro Phe Leu Leu Val Lys Thr Leu
                100                 105                 110

His Asn Ile Phe Val Gln Tyr Glu Ser Leu Gln Glu Lys Thr Cys Leu
            115                 120                 125

Phe Leu Ile Leu Asp Gly Phe Asp Ser Leu Gln Asp Leu Asp Ala Ala
130                 135                 140

Leu Phe Asn Lys Tyr Ile Lys Leu Asn Glu Leu Leu Pro Lys Asp Ser
145                 150                 155                 160

Lys Ile Asn Ile Lys Phe Ile Tyr Thr Met Leu Glu Thr Ser Phe Leu
                165                 170                 175

Gln Arg Tyr Ser Thr His Cys Ile Pro Thr Val Met Phe Pro Arg Tyr
            180                 185                 190

Asn Val Asp Glu Val Ser Thr Ile Leu Val Met Ser Arg Cys Gly Glu
        195                 200                 205

Leu Met Glu Asp Ser Cys Leu Arg Lys Arg Ile Ile Glu Glu Gln Ile
210                 215                 220

Thr Asp Cys Thr Asp Asp Gln Phe Gln Asn Val Ala Ala Asn Phe Ile
225                 230                 235                 240

His Leu Ile Val Gln Ala Phe His Ser Tyr Thr Gly Asn Asp Ile Phe
                245                 250                 255

Ala Leu Asn Asp Leu Ile Asp Phe Lys Trp Pro Lys Tyr Val Ser Arg
            260                 265                 270

Ile Thr Lys Glu Asn Ile Phe Glu Pro Leu Ala Leu Tyr Lys Ser Ala
        275                 280                 285

Ile Lys Leu Phe Leu Ser Thr Asp Asp Asn Leu Ser Glu Asn Gly Gln
290                 295                 300
```

| | | | | | | | | | | | | | | | |
|---|---|---|---|---|---|---|---|---|---|---|---|---|---|---|---|
| Gly | Glu | Ser | Ala | Ile | Thr | Thr | Asn | Arg | Asp | Asp | Leu | Glu | Asn | Ser | Gln |
| 305 | | | | 310 | | | | | 315 | | | | | | 320 |
| Thr | Tyr | Asp | Leu | Ser | Ile | Ile | Ser | Lys | Tyr | Leu | Leu | Ile | Ala | Ser | Tyr |
| | | | | 325 | | | | 330 | | | | | 335 | | |
| Ile | Cys | Ser | Tyr | Leu | Glu | Pro | Arg | Tyr | Asp | Ala | Ser | Ile | Phe | Ser | Arg |
| | | | 340 | | | | | 345 | | | | | 350 | | |
| Lys | Thr | Arg | Ile | Ile | Gln | Gly | Arg | Ala | Ala | Tyr | Gly | Arg | Arg | Lys | Lys |
| | | 355 | | | | | 360 | | | | | 365 | | | |
| Lys | Glu | Val | Asn | Pro | Arg | Tyr | Leu | Gln | Pro | Ser | Leu | Phe | Ala | Ile | Glu |
| | 370 | | | | | 375 | | | | 380 | | | | | |
| Arg | Leu | Leu | Ala | Ile | Phe | Gln | Ala | Ile | Phe | Pro | Ile | Gln | Gly | Lys | Ala |
| 385 | | | | | 390 | | | | | 395 | | | | | 400 |
| Glu | Ser | Gly | Ser | Leu | Ser | Ala | Leu | Arg | Glu | Glu | Ser | Leu | Met | Lys | Ala |
| | | | | 405 | | | | | 410 | | | | | 415 | |
| Asn | Ile | Glu | Val | Phe | Gln | Asn | Leu | Ser | Glu | Leu | His | Thr | Leu | Lys | Leu |
| | | | 420 | | | | | 425 | | | | | 430 | | |
| Ile | Ala | Thr | Thr | Met | Asn | Lys | Asn | Ile | Asp | Tyr | Leu | Ser | Pro | Lys | Val |
| | | 435 | | | | 440 | | | | | | 445 | | | |
| Arg | Trp | Lys | Val | Asn | Val | Pro | Trp | Glu | Ile | Ile | Lys | Glu | Ile | Ser | Glu |
| 450 | | | | | | 455 | | | | | 460 | | | | |
| Ser | Val | His | Phe | Asn | Ile | Ser | Asp | Tyr | Phe | Ser | Asp | Ile | His | Glu | |
| 465 | | | | | 470 | | | | | 475 | | | | | |

( 2 ) INFORMATION FOR SEQ ID NO:11:

( i ) SEQUENCE CHARACTERISTICS:
        ( A ) LENGTH: 1975 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 443..1747

( x i ) SEQUENCE DESCRIPTION: SEQ ID NO:11:

```
CGTGTGCTCT TCTATAGTAA TTTGACATTC TCTAAACGCA GAGACCTCTT ATAAAGATTC      60

AACAAATAAG GAATGTTACC TATGCTAGTC GCAACTCTCT CGTAAGTTGA GGGTTGCTAA     120

CAGAAAAACG ATGAGAAGAA ACTTTTGAAA AATATTGTGT GAAAGCAGCA CGAAACAGAG     180

TATGAAAAAA GAATGCGGGC GTCCGTAAAG AGCTAGAATC GCAAGTGTCC AGAATATGCA     240

AGGCTTTCGA ATACACTCCT CACGCTTCTC TTCAGCAAAA ATCAACTCTT TGTGATAAAA     300

CTGTGTATTT CTTTGTTCTT TGCCGTTGTT TACGTTAGTA AGAAATCGGC ATTGAAAAAA     360

AAAATCTCAC ACTAAAATTG CAGAAAAAAG TGTACAATAT CAGTAAATAA AATTGGCCAA     420
```

| | | | | | | | | | | | | | | |
|---|---|---|---|---|---|---|---|---|---|---|---|---|---|---|
| AACAATACCA TTAAAACCAG TC | ATG | TCC | ATG | CAA | CAA | GTC | CAA | CAT | TGT | GTC | | | | 472 |
| | Met | Ser | Met | Gln | Gln | Val | Gln | His | Cys | Val | | | | |
| | | | | | 625 | | | | | 630 | | | | |
| GCA | GAA | GTA | CTT | CGA | CTA | GAT | CCA | CAA | GAA | AAA | CCG | GAC | TGG | TCG | AGC | 520 |
| Ala | Glu | Val | Leu | Arg | Leu | Asp | Pro | Gln | Glu | Lys | Pro | Asp | Trp | Ser | Ser |
| | | | | 635 | | | | | 640 | | | | | 645 | |
| GGA | TAT | TTG | AAG | AAG | TTG | ACT | AAT | GCG | ACA | TCG | ATT | TTA | TAT | AAT | ACT | 568 |
| Gly | Tyr | Leu | Lys | Lys | Leu | Thr | Asn | Ala | Thr | Ser | Ile | Leu | Tyr | Asn | Thr |
| | | | 650 | | | | | 655 | | | | | 660 | | |
| TCA | CTG | AAC | AAG | GTA | ATG | CTG | AAA | CAA | GAT | GAA | GAG | GTT | GCT | AGA | TGT | 616 |
| Ser | Leu | Asn | Lys | Val | Met | Leu | Lys | Gln | Asp | Glu | Glu | Val | Ala | Arg | Cys |
| | | 665 | | | | | 670 | | | | | 675 | | | |

| Codon 1 | Codon 2 | Codon 3 | Codon 4 | Codon 5 | Codon 6 | Codon 7 | Codon 8 | Codon 9 | Codon 10 | Codon 11 | Codon 12 | Codon 13 | Codon 14 | Codon 15 | Codon 16 | Position |
|---|---|---|---|---|---|---|---|---|---|---|---|---|---|---|---|---|
| CAC His 680 | ATA Ile | TGT Cys | GCA Ala | TAC Tyr | ATA Ile 685 | GCG Ala | TCA Ser | CAG Gln | AAA Lys | ATG Met 690 | AAT Asn | GAA Glu | AAA Lys | CAC His | ATG Met | 664 |
| CCT Pro 695 | GAC Asp | CTT Leu | TGC Cys | TAT Tyr | TAT Tyr 700 | ATA Ile | GAC Asp | AGT Ser | ATT Ile | CCC Pro 705 | TTG Leu | GAG Glu | CCG Pro | AAA Lys | AAA Lys 710 | 712 |
| GCC Ala | AAG Lys | CAT His | TTA Leu | ATG Met 715 | AAC Asn | CTT Leu | TTC Phe | AGA Arg | CAA Gln 720 | AGT Ser | TTA Leu | TCT Ser | AAT Asn | TCT Ser 725 | TCA Ser | 760 |
| CCT Pro | ATG Met | AAA Lys | CAA Gln 730 | TTT Phe | GCT Ala | TGG Trp | ACA Thr | CCG Pro 735 | AGC Ser | CCC Pro | AAA Lys | AAG Lys | AAC Asn 740 | AAA Lys | CGC Arg | 808 |
| AGT Ser | CCA Pro | GTA Val 745 | AAG Lys | AAC Asn | GGT Gly | GGG Gly | AGG Arg 750 | TTT Phe | ACT Thr | TCT Ser | TCT Ser | GAT Asp 755 | CCG Pro | AAA Lys | GAG Glu | 856 |
| TTG Leu | AGG Arg 760 | AAT Asn | CAA Gln | CTG Leu | TTT Phe | GGT Gly 765 | ACA Thr | CCA Pro | ACT Thr | AAA Lys | GTT Val 770 | AGG Arg | AAA Lys | AGC Ser | CAA Gln | 904 |
| AAT Asn 775 | AAT Asn | GAT Asp | TCG Ser | TTC Phe | GTA Val 780 | ATA Ile | CCA Pro | GAA Glu | CTA Leu | CCC Pro 785 | CCC Pro | ATG Met | CAA Gln | ACC Thr | AAT Asn 790 | 952 |
| GAA Glu | TCG Ser | CCG Pro | TCT Ser | ATT Ile | ACT Thr 795 | AGG Arg | AGA Arg | AAG Lys | TTA Leu | GCA Ala 800 | TTT Phe | GAA Glu | GAG Glu | GAT Asp | GAG Glu 805 | 1000 |
| GAT Asp | GAG Glu | GAT Asp | GAA Glu 810 | GAG Glu | GAA Glu | CCA Pro | GGA Gly | AAC Asn 815 | GAC Asp | GGT Gly | TTG Leu | TCT Ser | TTA Leu 820 | AAA Lys | AGC Ser | 1048 |
| CAT His | AGT Ser | AAT Asn 825 | AAG Lys | AGC Ser | ATT Ile | ACT Thr | GGA Gly 830 | ACC Thr | AGA Arg | AAT Asn | GTA Val | GAT Asp 835 | TCT Ser | GAT Asp | GAG Glu | 1096 |
| TAT Tyr | GAA Glu 840 | AAC Asn | CAT His | GAA Glu | AGT Ser | GAC Asp 845 | CCT Pro | ACA Thr | AGT Ser | GAG Glu | GAA Glu 850 | GAG Glu | CCA Pro | TTA Leu | GGT Gly | 1144 |
| GTG Val 855 | CAA Gln | GAA Glu | AGC Ser | AGA Arg | AGC Ser 860 | GGG Gly | AGA Arg | ACG Thr | AAA Lys | CAA Gln 865 | AAT Asn | AAG Lys | GCA Ala | GTT Val | GGA Gly 870 | 1192 |
| AAA Lys | CCG Pro | CAA Gln | TCA Ser | GAA Glu 875 | TTG Leu | AAG Lys | ACG Thr | GCA Ala | AAA Lys 880 | GCC Ala | CTG Leu | AGG Arg | AAA Lys | AGG Arg 885 | GGC Gly | 1240 |
| AGA Arg | ATA Ile | CCA Pro | AAT Asn 890 | TCT Ser | TTG Leu | TTA Leu | GTA Val | AAG Lys 895 | AAG Lys | TAT Tyr | TGC Cys | AAA Lys | ATG Met 900 | ACT Thr | ACT Thr | 1288 |
| GAA Glu | GAA Glu | ATA Ile | ATA Ile 905 | CGG Arg | CTT Leu | TGC Cys | AAC Asn | GAT Asp 910 | TTT Phe | GAA Glu | TTA Leu | CCA Pro | AGA Arg 915 | GAA Glu | GTA Val | 1336 |
| GCA Ala | TAT Tyr | AAA Lys 920 | ATT Ile | GTG Val | GAT Asp | GAG Glu | TAC Tyr 925 | AAC Asn | ATA Ile | AAC Asn | GCG Ala | TCA Ser 930 | AGA Arg | TTG Leu | GTT Val | 1384 |
| TGC Cys 935 | CCA Pro | TGG Trp | CAA Gln | TTA Leu | GTG Val 940 | TGT Cys | GGG Gly | TTA Leu | GTA Val | TTA Leu 945 | AAT Asn | TGT Cys | ACA Thr | TTC Phe | ATT Ile 950 | 1432 |
| GTA Val | TTT Phe | AAT Asn | GAA Glu | AGA Arg 955 | AGA Arg | CGC Arg | AAG Lys | GAT Asp | CCA Pro 960 | AGA Arg | ATT Ile | GAC Asp | CAT His | TTT Phe 965 | ATA Ile | 1480 |
| GTC Val | AGT Ser | AAG Lys | ATG Met 970 | TGC Cys | AGC Ser | TTG Leu | ATG Met | TTG Leu 975 | ACG Thr | TCA Ser | AAA Lys | GTG Val | GAT Asp 980 | GAT Asp | GTT Val | 1528 |
| ATT Ile | GAA Glu | TGT Cys | GTA Val | AAA Lys 985 | TTA Leu | GTG Val | AAG Lys | GAA Glu | TTA Leu 990 | ATT Ile | ATC Ile | GGT Gly | GAA Glu | AAA Lys 995 | TGG Trp | 1576 |

| | | | | | | | | | | | | | | | | |
|---|---|---|---|---|---|---|---|---|---|---|---|---|---|---|---|---|
|TTC|AGA|GAT|TTG|CAA|ATT|AGG|TAT|GAT|GAT|TTT|GAT|GGC|ATC|AGA|TAC|1624|
|Phe|Arg|Asp|Leu|Gln|Ile|Arg|Tyr|Asp|Asp|Phe|Asp|Gly|Ile|Arg|Tyr| |
| |1000| | | |1005| | | | |1010| | | | | | |
|GAT|GAA|ATT|ATA|TTT|AGG|AAA|CTG|GGA|TCG|ATG|TTA|CAA|ACC|ACC|AAT|1672|
|Asp|Glu|Ile|Ile|Phe|Arg|Lys|Leu|Gly|Ser|Met|Leu|Gln|Thr|Thr|Asn| |
|1015| | | | |1020| | | | |1025| | | | |1030| |
|ATT|TTG|GTC|ACA|GAC|GAC|CAG|TAC|AAT|ATT|TGG|AAG|AAA|AGA|ATT|GAA|1720|
|Ile|Leu|Val|Thr|Asp|Asp|Gln|Tyr|Asn|Ile|Trp|Lys|Lys|Arg|Ile|Glu| |
| | | | |1035| | | |1040| | | | |1045| | | |
|ATG|GAT|TTG|GCA|TTA|ACA|GAA|CCT|TTA|TAACATATCC|AGTATTAACT| | | | | |1767|
|Met|Asp|Leu|Ala|Leu|Thr|Glu|Pro|Leu| | | | | | | | |
| |1050| | | | |1055| | | | | | | | | | |

AAAAGTATAT ATTTGACCAA TACCTGACAT ATCTTCTAAA GCATGCCTTT AGCCCTATAA  1827

CGAGCTAATG TTAGCTCCAT CTTTGCACTT ATGATTGGAT CAGCCCTCAA ACGCTTTTGT  1887

ATCTTTGCAG CTTCCGCGAA GGTAGTAGCT TGAAGTTTTT CATCCATAGT TCTTGCTAAA  1947

ATTGCAGAAT CTTCAAACAA TTCTATGG  1975

( 2 ) INFORMATION FOR SEQ ID NO:12:

( i ) SEQUENCE CHARACTERISTICS:
        ( A ) LENGTH: 435 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
|Met|Ser|Met|Gln|Gln|Val|Gln|His|Cys|Val|Ala|Glu|Val|Leu|Arg|Leu|
|1| | | |5| | | | |10| | | | |15| |
|Asp|Pro|Gln|Glu|Lys|Pro|Asp|Trp|Ser|Ser|Gly|Tyr|Leu|Lys|Lys|Leu|
| | | |20| | | | |25| | | | |30| | |
|Thr|Asn|Ala|Thr|Ser|Ile|Leu|Tyr|Asn|Thr|Ser|Leu|Asn|Lys|Val|Met|
| | | |35| | | | |40| | | | |45| | |
|Leu|Lys|Gln|Asp|Glu|Glu|Val|Ala|Arg|Cys|His|Ile|Cys|Ala|Tyr|Ile|
| | |50| | | | |55| | | | |60| | | |
|Ala|Ser|Gln|Lys|Met|Asn|Glu|Lys|His|Met|Pro|Asp|Leu|Cys|Tyr|Tyr|
|65| | | | |70| | | | |75| | | | |80|
|Ile|Asp|Ser|Ile|Pro|Leu|Glu|Pro|Lys|Lys|Ala|Lys|His|Leu|Met|Asn|
| | | | |85| | | | |90| | | | |95| |
|Leu|Phe|Arg|Gln|Ser|Leu|Ser|Asn|Ser|Ser|Pro|Met|Lys|Gln|Phe|Ala|
| | | |100| | | | |105| | | | |110| | |
|Trp|Thr|Pro|Ser|Pro|Lys|Lys|Asn|Lys|Arg|Ser|Pro|Val|Lys|Asn|Gly|
| | |115| | | | |120| | | | |125| | | |
|Gly|Arg|Phe|Thr|Ser|Ser|Asp|Pro|Lys|Glu|Leu|Arg|Asn|Gln|Leu|Phe|
| |130| | | | |135| | | | |140| | | | |
|Gly|Thr|Pro|Thr|Lys|Val|Arg|Lys|Ser|Gln|Asn|Asn|Asp|Ser|Phe|Val|
|145| | | | |150| | | | |155| | | | |160|
|Ile|Pro|Glu|Leu|Pro|Pro|Met|Gln|Thr|Asn|Glu|Ser|Pro|Ser|Ile|Thr|
| | | | |165| | | | |170| | | | |175| |
|Arg|Arg|Lys|Leu|Ala|Phe|Glu|Glu|Asp|Glu|Asp|Glu|Asp|Glu|Glu|Glu|
| | | |180| | | | |185| | | | |190| | |
|Pro|Gly|Asn|Asp|Gly|Leu|Ser|Leu|Lys|Ser|His|Ser|Asn|Lys|Ser|Ile|
| | |195| | | | |200| | | | |205| | | |
|Thr|Gly|Thr|Arg|Asn|Val|Asp|Ser|Asp|Glu|Tyr|Glu|Asn|His|Glu|Ser|
| |210| | | | |215| | | | |220| | | | |
|Asp|Pro|Thr|Ser|Glu|Glu|Glu|Pro|Leu|Gly|Val|Gln|Glu|Ser|Arg|Ser|
|225| | | | |230| | | | |235| | | | |240|

|   |   |   |   |   |   |   |   |   |   |   |   |   |   |   |
|---|---|---|---|---|---|---|---|---|---|---|---|---|---|---|
| Gly | Arg | Thr | Lys | Gln | Asn | Lys | Ala | Val | Gly | Lys | Pro | Gln | Ser | Glu | Leu |
|  |  |  |  | 245 |  |  |  |  | 250 |  |  |  | 255 |  |
| Lys | Thr | Ala | Lys | Ala | Leu | Arg | Lys | Arg | Gly | Arg | Ile | Pro | Asn | Ser | Leu |
|  |  |  | 260 |  |  |  |  | 265 |  |  |  |  | 270 |  |  |
| Leu | Val | Lys | Lys | Tyr | Cys | Lys | Met | Thr | Thr | Glu | Glu | Ile | Ile | Arg | Leu |
|  |  | 275 |  |  |  |  | 280 |  |  |  |  | 285 |  |  |  |
| Cys | Asn | Asp | Phe | Glu | Leu | Pro | Arg | Glu | Val | Ala | Tyr | Lys | Ile | Val | Asp |
|  |  | 290 |  |  |  |  | 295 |  |  |  |  | 300 |  |  |  |
| Glu | Tyr | Asn | Ile | Asn | Ala | Ser | Arg | Leu | Val | Cys | Pro | Trp | Gln | Leu | Val |
| 305 |  |  |  |  | 310 |  |  |  |  | 315 |  |  |  |  | 320 |
| Cys | Gly | Leu | Val | Leu | Asn | Cys | Thr | Phe | Ile | Val | Phe | Asn | Glu | Arg | Arg |
|  |  |  |  | 325 |  |  |  |  | 330 |  |  |  |  | 335 |  |
| Arg | Lys | Asp | Pro | Arg | Ile | Asp | His | Phe | Ile | Val | Ser | Lys | Met | Cys | Ser |
|  |  |  | 340 |  |  |  |  | 345 |  |  |  |  | 350 |  |  |
| Leu | Met | Leu | Thr | Ser | Lys | Val | Asp | Asp | Val | Ile | Glu | Cys | Val | Lys | Leu |
|  |  | 355 |  |  |  |  | 360 |  |  |  |  | 365 |  |  |  |
| Val | Lys | Glu | Leu | Ile | Ile | Gly | Glu | Lys | Trp | Phe | Arg | Asp | Leu | Gln | Ile |
|  | 370 |  |  |  |  | 375 |  |  |  |  | 380 |  |  |  |  |
| Arg | Tyr | Asp | Asp | Phe | Asp | Gly | Ile | Arg | Tyr | Asp | Glu | Ile | Ile | Phe | Arg |
| 385 |  |  |  |  | 390 |  |  |  |  | 395 |  |  |  |  | 400 |
| Lys | Leu | Gly | Ser | Met | Leu | Gln | Thr | Thr | Asn | Ile | Leu | Val | Thr | Asp | Asp |
|  |  |  |  | 405 |  |  |  |  | 410 |  |  |  |  | 415 |  |
| Gln | Tyr | Asn | Ile | Trp | Lys | Lys | Arg | Ile | Glu | Met | Asp | Leu | Ala | Leu | Thr |
|  |  |  | 420 |  |  |  |  | 425 |  |  |  |  | 430 |  |  |
| Glu | Pro | Leu |
|  |  | 435 |

( 2 ) INFORMATION FOR SEQ ID NO:13:

( i ) SEQUENCE CHARACTERISTICS:
( A ) LENGTH: 3278 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:13:

```
CAAGGAATGG TGCATGCAAG GAGATGGCGC CCAACAGTCC CCGCCACGGG CCTGCCACCA      60
TACCCACGCC GAAACAAGCG CTCATGAGCC CGAAGTGGCG AGCCCGATCT TCCCCATCGG     120
TGATGTCGGC GATATAGGCG CCAGCAACCG CACCTGTGGC GCCGGTGATG CCGGCCACGA     180
TGCGTCCGGC GTAGAGGATC TTAATTCAGT AAACAGAGGA ACCGTGTAAC AACCAATATG     240
CTATGAGATA AAAGAATGCT ACGGAAACAG GTAGCTGTCA TTTCAACATA CTTGGCCAGC     300
AAGTAACTMC NACTAGTTTA GGAAGGNNTT ACTGCATTTT AACGGTTATC TGATTATTTT     360
TCCTTTTTAT TCCGTGGTAG CGAGTTTATT AGGCATGGCG TCAACGTTAG CTGAGTTTGA     420
AGTTCAATGG GAAATACAGA AGACAGACTT GAAGGGGAAT CTCATTGCTG AAACTCCTAG     480
GCGAAGAAGA AGAGGAGATG CTACAGAACA TGAAGTGATT AATTTGGTAC GATACGATGG     540
AGTCAGACTT TATCCTGGTG TTACGATTGT GTGCAAGGTA GAGGGTGCAG ACGAGTTATC     600
AGCGTATATG ATCCATGAGG TGCGATTGAA TACAAGCAAT TACGTAGAAC TCTGGTGTTT     660
GAACTATTTG AGTTGGTACG AGATCAATGC TGCGGAAAGA TATAAACAGC TTGATGGAGA     720
GTTTATGAG ACTAATAAGG AAAAAGGTGA CAAATTTTTT GAGGAAACCT TCGCGTCACA     780
ATCGATAAAG AACGAATTGT ATTTGACAGC TGAGCTTTCA GAGATTTATC TACGGGACTT     840
```

| | | | | | | |
|---|---|---|---|---|---|---|
| GCAATTTGTA | GCTAATATTA | AAAATGAAAA | GGAGTATTTA | GACTCTGTCA | ATGAAGGGAA | 900 |
| AATGGATTCT | AATATGTTTT | TATGTCGATC | TGCATGCTTG | CCTTCAGGAA | CTAATCTGGC | 960 |
| GGATTTAGAT | ATACATTTCT | TTGAAGAAAA | AATACGTTCC | TCGAATCCTA | AGGTGTCTCT | 1020 |
| GGAGTATTTG | CGTGATATTA | CTTTACCCAA | GCTTCCAAAA | CCTTTAAATA | AATCCAAGGT | 1080 |
| CCACGCACGA | GAGAAGGTAG | TGGCGACGAA | ATTGCAGTCC | GACAACACAC | CAAGCAAAAA | 1140 |
| AAGCTTTCAA | CAAACAGTGA | GCAAACCAA | CGCTGAAGTC | CAACGCATTG | CATCTACTAT | 1200 |
| TGTTAACGAA | AAGGAAGCTA | TATCAGATAA | TGAATCGGAT | TTATCTGAAT | ATCACGAAAG | 1260 |
| TAAAGAAGAG | TTTGCAAACG | CATCCTCTTC | GGACAGTGAT | GAAGAGTTTG | AAGATTACCA | 1320 |
| GTCTGCAGAA | GAGCTTGCAA | TTGTAGAACC | TGCCAAGAAA | AAGGTGAGAT | CTATTAAACC | 1380 |
| AGATATACCC | ATTTCACCAG | TAAAATCACA | GACTCCATTG | CAGCCATCAG | CAGTTCATTC | 1440 |
| ATCTCCTAGA | AAGTTCTTTA | AGAATAATAT | AGTGCGCGCT | AAAAAGGCAT | ATACTCCATT | 1500 |
| TTCCAAACGG | TATAAGAATC | CGAAGATTCC | TGACTTGAAC | GATATTTTCC | AAAGGCATAA | 1560 |
| TAATGATTTG | GATATAGCTG | CATTAGAGGA | GAGATTCAGA | ACAGTTTCTG | CTAAAGGCAA | 1620 |
| AATGGAGACT | ATTTTTTCTA | AGGTGAAGAA | GCAATTGAAC | TCAAGGAATA | GCAAAGAAGA | 1680 |
| AATTGTCAAA | GCTGCTGATT | TCGACAATTA | TCTTCCGGCA | AGAGAAAATG | AATTTGCAAG | 1740 |
| TATATACCTC | TCACTTTACA | GTGCAATTGA | AGCAGGCACT | AGCACCAGTA | TTTACATTGC | 1800 |
| CGGGACGCCA | GGCGTTGGTA | AAACTTTGAC | GGTTCGAGAG | GTAGTTAAGG | ATTTAATGAC | 1860 |
| ATCTGCAGAC | CAAAAGAAC | TTCCAAGATT | CCAATACATT | GAAATCAATG | GTTTAAAGAT | 1920 |
| TGTCAAAGCA | AGTGATAGTT | ATGAAGTCTT | TTGGCAAAAA | ATATCTGGAG | AAAAGCTTAC | 1980 |
| ATCTGGAGCT | GCCATGGAAT | CTCTGGAGTT | TTATTTAAC | AAAGTTCCAG | CTACGAAAAA | 2040 |
| ACGTCCTATC | GTTGTGTTAT | TGGATGAGCT | TGATGCATTA | GTTAGCAAGA | GCCAAGATGT | 2100 |
| AATGTACAAC | TTCTTTAACT | GGGCTACCTA | TTCAAATGCG | AAACTTATTG | TTGTAGCTGT | 2160 |
| CGCAAACACC | TTAGATCTCC | CCGAACGCCA | TCTTGGTAAC | AAGATTTCGT | CCAGAATTGG | 2220 |
| TTTTACTAGA | ATTATGTTCA | CTGGTTACAC | GCATGAAGAG | CTTAGAACAA | TCATCAATTT | 2280 |
| GAGACTTAAA | TATTTGAACG | AATCTAGTTT | CTATGTCGAC | CCGGAGACAG | GGAGTTCGTA | 2340 |
| CATGATCTCT | CCGGATAGTA | GTACTATAGA | AACTGATGAA | GAAGAAAAGC | GAAAAGACTT | 2400 |
| CTCTAACTAT | AAACGACTAA | AACTTAGGAT | TAATCCTGAT | GCCATTGAGA | TTGCATCAAG | 2460 |
| AAAAATTGCT | AGTGTCAGTG | GTGATGTGCG | GAGAGCTTTA | AAGGTGGTCA | AAGAGCGGT | 2520 |
| AGAATATGCG | GAAAATGATT | ACTTAAAGAG | GCTTAGATAT | GAGCGACTAG | TCAATTCCAA | 2580 |
| AAAAGATACT | AGTGGCAATG | GTACAGGAAA | TGAAGAATTA | CAGAGTGTAG | AAATTAAGCA | 2640 |
| TATTACCAAG | GCATTAAACG | AAAGTTCGAC | CTCTCCGGAA | CAACAATTCA | TATCTGGTCT | 2700 |
| GTCATTTAGC | GGAAAACTTT | TCCTATACGC | ATTAATCAAT | TTAATTAAGA | AGAAGCAAAC | 2760 |
| TGACGTACAA | CTTGGTGATA | TCGTAGAAGA | AATGAGGCTC | CTCATTGATG | TCAATGGGAA | 2820 |
| TAACAAATAC | ATTTTAGAGT | TGAAACGGAT | TTTATTCCAA | AATGATTCTG | TTGATACAAA | 2880 |
| GGAACAGTTA | AGGGCCGTGT | CTTGGGACTA | TATTTTATTG | CAATTATTGG | ATGCAGGTGT | 2940 |
| TGTAGTAAGG | CAATATTTCA | AGAATGAGAG | GCTCTCGACG | ATCAAATTAA | ATATTTCCAT | 3000 |
| GGAAGATGCG | GACGAATGCT | TGCATGAAGA | TGAAATGTTG | AAGACATTTT | AGTATATGCC | 3060 |
| TTCAAGACGC | CTTTGCTGCT | ATTATAATTG | CTACTTAGGT | TGTCATGTAG | CGTACGTTAA | 3120 |
| GTAGAATATG | AAACTGCTTT | TTNCAACTAT | TTAATTATAA | GATAGAAAGA | TATAATAAAG | 3180 |
| GATGCATTTT | TTTTAACTAC | TATTTTACCG | TGTTTATTCA | TTCTTTACCC | TCCGCTTCGG | 3240 |

CAAGATGAAC GTGATCACGT AATAGGAGGT AGGTGATT                                    3278

( 2 ) INFORMATION FOR SEQ ID NO:14:

( i ) SEQUENCE CHARACTERISTICS:
        ( A ) LENGTH: 885 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

```
Met Ala Ser Thr Leu Ala Glu Phe Glu Val Gln Trp Glu Ile Gln Lys
 1               5                  10                  15

Thr Asp Leu Lys Gly Asn Leu Ile Ala Glu Thr Pro Arg Arg Arg Arg
            20                  25                  30

Arg Gly Asp Ala Thr Glu His Glu Val Ile Asn Leu Val Arg Tyr Asp
        35                  40                  45

Gly Val Arg Leu Tyr Pro Gly Val Thr Ile Val Cys Lys Val Glu Gly
    50                  55                  60

Ala Asp Glu Leu Ser Ala Tyr Met Ile His Glu Val Arg Leu Asn Thr
65                  70                  75                  80

Ser Asn Tyr Val Glu Leu Trp Cys Leu Asn Tyr Leu Ser Trp Tyr Glu
                85                  90                  95

Ile Asn Ala Ala Glu Arg Tyr Lys Gln Leu Asp Gly Glu Phe Tyr Glu
                100                 105                 110

Thr Asn Lys Glu Lys Gly Asp Lys Phe Phe Glu Glu Thr Phe Ala Ser
            115                 120                 125

Gln Ser Ile Lys Asn Glu Leu Tyr Leu Thr Ala Glu Leu Ser Glu Ile
    130                 135                 140

Tyr Leu Arg Asp Leu Gln Phe Val Ala Asn Ile Lys Asn Glu Lys Glu
145                 150                 155                 160

Tyr Leu Asp Ser Val Asn Glu Gly Lys Met Asp Ser Asn Met Phe Leu
                165                 170                 175

Cys Arg Ser Ala Cys Leu Pro Ser Gly Thr Asn Leu Ala Asp Leu Asp
                180                 185                 190

Ile His Phe Phe Glu Glu Lys Ile Arg Ser Ser Asn Pro Lys Val Ser
            195                 200                 205

Leu Glu Tyr Leu Arg Asp Ile Thr Leu Pro Lys Leu Pro Lys Pro Leu
    210                 215                 220

Asn Lys Ser Lys Val His Ala Arg Glu Lys Val Val Ala Thr Lys Leu
225                 230                 235                 240

Gln Ser Asp Asn Thr Pro Ser Lys Lys Ser Phe Gln Gln Thr Val Ser
                245                 250                 255

Lys Thr Asn Ala Glu Val Gln Arg Ile Ala Ser Thr Ile Val Asn Glu
                260                 265                 270

Lys Glu Ala Ile Ser Asp Asn Glu Ser Asp Leu Ser Glu Tyr His Glu
            275                 280                 285

Ser Lys Glu Glu Phe Ala Asn Ala Ser Ser Ser Asp Ser Asp Glu Glu
    290                 295                 300

Phe Glu Asp Tyr Gln Ser Ala Glu Glu Leu Ala Ile Val Glu Pro Ala
305                 310                 315                 320

Lys Lys Lys Val Arg Ser Ile Lys Pro Asp Ile Pro Ile Ser Pro Val
                325                 330                 335

Lys Ser Gln Thr Pro Leu Gln Pro Ser Ala Val His Ser Ser Pro Arg
```

-continued

|   |     |     |     | 340 |     |     |     | 345 |     |     |     | 350 |     |     |
|---|-----|-----|-----|-----|-----|-----|-----|-----|-----|-----|-----|-----|-----|-----|
| Lys | Phe | Phe 355 | Lys | Asn | Asn | Ile | Val 360 | Arg | Ala | Lys | Lys | Ala 365 | Tyr | Thr | Pro |
| Phe | Ser | Lys 370 | Arg | Tyr | Lys | Asn | Pro 375 | Lys | Ile | Pro | Asp | Leu 380 | Asn | Asp | Ile |
| Phe 385 | Gln | Arg | His | Asn | Asn 390 | Asp | Leu | Asp | Ile | Ala 395 | Ala | Leu | Glu | Glu | Arg 400 |
| Phe | Arg | Thr | Val | Ser 405 | Ala | Lys | Gly | Lys | Met 410 | Glu | Thr | Ile | Phe | Ser 415 | Lys |
| Val | Lys | Lys | Gln 420 | Leu | Asn | Ser | Arg | Asn 425 | Ser | Lys | Glu | Glu | Ile 430 | Val | Lys |
| Ala | Ala | Asp 435 | Phe | Asp | Asn | Tyr | Leu 440 | Pro | Ala | Arg | Glu | Asn 445 | Glu | Phe | Ala |
| Ser | Ile 450 | Tyr | Leu | Ser | Leu | Tyr 455 | Ser | Ala | Ile | Glu | Ala 460 | Gly | Thr | Ser | Thr |
| Ser 465 | Ile | Tyr | Ile | Ala | Gly 470 | Thr | Pro | Gly | Val | Gly 475 | Lys | Thr | Leu | Thr | Val 480 |
| Arg | Glu | Val | Val | Lys 485 | Asp | Leu | Met | Thr | Ser 490 | Ala | Asp | Gln | Lys | Glu 495 | Leu |
| Pro | Arg | Phe | Gln 500 | Tyr | Ile | Glu | Ile | Asn 505 | Gly | Leu | Lys | Ile | Val 510 | Lys | Ala |
| Ser | Asp | Ser 515 | Tyr | Glu | Val | Phe | Trp 520 | Gln | Lys | Ile | Ser | Gly 525 | Glu | Lys | Leu |
| Thr | Ser 530 | Gly | Ala | Ala | Met | Glu 535 | Ser | Leu | Glu | Phe | Tyr 540 | Phe | Asn | Lys | Val |
| Pro | Ala | Thr | Lys | Lys 550 | Arg | Pro | Ile | Val | Val 555 | Leu | Leu | Asp | Glu | Leu | Asp 560 |
| Pro 545 |     |     |     |     |     |     |     |     |     |     |     |     |     |     |     |
| Ala | Leu | Val | Ser | Lys 565 | Ser | Gln | Asp | Val | Met 570 | Tyr | Asn | Phe | Phe | Asn 575 | Trp |
| Ala | Thr | Tyr | Ser 580 | Asn | Ala | Lys | Leu | Ile 585 | Val | Val | Ala | Val | Ala 590 | Asn | Thr |
| Leu | Asp | Leu 595 | Pro | Glu | Arg | His | Leu 600 | Gly | Asn | Lys | Ile | Ser 605 | Ser | Arg | Ile |
| Gly | Phe 610 | Thr | Arg | Ile | Met | Phe 615 | Thr | Gly | Tyr | Thr | His 620 | Glu | Glu | Leu | Arg |
| Thr 625 | Ile | Ile | Asn | Leu | Arg 630 | Leu | Lys | Tyr | Leu | Asn 635 | Glu | Ser | Ser | Phe | Tyr 640 |
| Val | Asp | Pro | Glu | Thr 645 | Gly | Ser | Ser | Tyr | Met 650 | Ile | Ser | Pro | Asp | Ser 655 | Ser |
| Thr | Ile | Glu | Thr 660 | Asp | Glu | Glu | Glu | Lys 665 | Arg | Lys | Asp | Phe | Ser 670 | Asn | Tyr |
| Lys | Arg | Leu 675 | Lys | Leu | Arg | Ile | Asn 680 | Pro | Asp | Ala | Ile | Glu 685 | Ile | Ala | Ser |
| Arg | Lys 690 | Ile | Ala | Ser | Val | Ser 695 | Gly | Asp | Val | Arg | Arg 700 | Ala | Leu | Lys | Val |
| Val 705 | Lys | Arg | Ala | Val | Glu 710 | Tyr | Ala | Glu | Asn | Asp 715 | Tyr | Leu | Lys | Arg | Leu 720 |
| Arg | Tyr | Glu | Arg | Leu 725 | Val | Asn | Ser | Lys | Lys 730 | Asp | Thr | Ser | Gly | Asn 735 | Gly |
| Thr | Gly | Asn | Glu 740 | Glu | Leu | Gln | Ser | Val 745 | Glu | Ile | Lys | His | Ile 750 | Thr | Lys |
| Ala | Leu | Asn 755 | Glu | Ser | Ser | Thr | Ser 760 | Pro | Glu | Gln | Gln | Phe 765 | Ile | Ser | Gly |

| | | | | | | | | | | | | | | |
|---|---|---|---|---|---|---|---|---|---|---|---|---|---|---|
| Leu | Ser | Phe | Ser | Gly | Lys | Leu | Phe | Leu | Tyr | Ala | Leu | Ile | Asn | Leu | Ile |
| 770 | | | | | 775 | | | | | 780 | | | | |
| Lys | Lys | Lys | Gln | Thr | Asp | Val | Gln | Leu | Gly | Asp | Ile | Val | Glu | Glu | Met |
| 785 | | | | 790 | | | | | 795 | | | | | 800 |
| Arg | Leu | Leu | Ile | Asp | Val | Asn | Gly | Asn | Asn | Lys | Tyr | Ile | Leu | Glu | Leu |
| | | | | 805 | | | | | 810 | | | | | 815 | |
| Lys | Arg | Ile | Leu | Phe | Gln | Asn | Asp | Ser | Val | Asp | Thr | Lys | Glu | Gln | Leu |
| | | | 820 | | | | | 825 | | | | 830 | | | |
| Arg | Ala | Val | Ser | Trp | Asp | Tyr | Ile | Leu | Leu | Gln | Leu | Leu | Asp | Ala | Gly |
| | | 835 | | | | | 840 | | | | | 845 | | | |
| Val | Val | Val | Arg | Gln | Tyr | Phe | Lys | Asn | Glu | Arg | Leu | Ser | Thr | Ile | Lys |
| | 850 | | | | | 855 | | | | | 860 | | | | |
| Leu | Asn | Ile | Ser | Met | Glu | Asp | Ala | Asp | Glu | Cys | Leu | His | Glu | Asp | Glu |
| 865 | | | | | 870 | | | | | 875 | | | | | 880 |
| Met | Leu | Lys | Thr | Phe | | | | | | | | | | | |
| | | | | 885 | | | | | | | | | | | |

( 2 ) INFORMATION FOR SEQ ID NO:15:

( i ) SEQUENCE CHARACTERISTICS:
( A ) LENGTH: 2504 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:15:

| | | | | | |
|---|---|---|---|---|---|
| TACGAGTCTT | GTTAGTCCAG | CACTACAACT | CAGGATAACT | TTGACCATTG | CAATGTTGAT | 60 |
| AAACTAGTGT | TGAACTTCTC | TTAATATGCC | TAGAAGAAAG | TCATTGAGGA | GTCAACTATT | 120 |
| AATTAACGGC | ATTGATAAAA | GTCTGCTATC | TGATGACAGC | GCTGACAGTT | CTGATATTGA | 180 |
| CGAAGAGGAA | GTTACGGTG | TTTGGACTGA | AGAGCCCTTT | CAAAAGAGG | CTGGACGTTC | 240 |
| TTATTACAGA | TCTTTAAAGA | AAAACGATGT | AATATATCGC | GTTGGAGATG | ATATTACTGT | 300 |
| ACATGATGGA | GACTCAAGCT | TTTATCTGGG | GGTAATTTGT | AAATTGTACG | AAAAAGCAAT | 360 |
| TGATAAGCAT | TCTGGAAAGA | AATATGTTGA | AGCAATTTGG | TATAGTCGAG | CTTATGCTAA | 420 |
| GAGAATGGAA | ATTAAACCTG | AATATTTGTT | GCCAGACCGG | CATATAAATG | AGGTGTACGT | 480 |
| TTCTTGTGGC | CGGGATGAAA | ACCTGACTTC | ATGTATAATA | GAGCATTGTA | ATGTCTACTC | 540 |
| TGAAGCAGAG | TTTTTTTCAA | AATTTCCCGC | TGGAATTCCT | ACAAAACGAA | AAGATTTGTT | 600 |
| TCCTTGTAAC | TTCTTTATCC | GACGCGGTGT | ACACTTGAAA | GTGAACAAAT | ACACAGAACC | 660 |
| TCTCGATTGG | TCTTATTATG | CTCATAATCT | TGAAAGGATA | GAAGATCTTT | TGGTTGAGAT | 720 |
| GGAAGAAAAT | TTGCGACCAA | CTAAAAAGAA | ATCTGGTTCT | AGAGGTCGTG | GTCGCCCTCG | 780 |
| TAAATATCCT | TTACCAAATG | TCGAAAGCAA | AGAAAGCAGT | TCCAAAGTTA | ACTCTAAGGA | 840 |
| TGAAAATTTT | GATTTACAAG | ATGATAGTGA | ATCTTCAGAA | GATAATTTGA | CTATACAACC | 900 |
| TCAGACACCA | AGGCGCCGTC | ATAAAAGATC | AAGACACAAT | TCATCAAATT | TGGCTTCTAC | 960 |
| TCCAAAAAGA | AATGGCTACA | ACAACCATT | ACAAATTACT | CCGCTACCTA | TTCGTATGCT | 1020 |
| GTCCCTTGAG | GAGTTTCAGG | GTTCTCCTCA | TAGAAAGCT | AGGGCTATGC | TTCATGTTGC | 1080 |
| TTCAGTTCCA | AGCACATTAC | AATGTCGCGA | TAACGAATTT | CTACCATAT | TTTCGAACTT | 1140 |
| AGAAAGTGCC | ATTGAAGAAG | AGACAGGGGC | TTGTCTCTAT | ATATCTGGTA | CGCCGGGAAC | 1200 |
| AGGAAAAACT | GCTACTGTTC | ACGAAGTAAT | TTGGAATCTT | CAGGAATTAT | CTCGAGAAGG | 1260 |
| ACAACTTCCT | GAATTTTCAT | TCTGCGAAAT | TAATGGAATG | CGTGTAACCA | GTGCAAACCA | 1320 |

```
GGCATATTCT ATTCTCTGGG AATCTTTGAC GGGTGAAAGA GTTACTCCAA TCCATGCAAT    1380

GGACCTTCTT GATAACCGAT TTACTCATGC TTCTCCAAAC CGCAGTAGTT GTGTTGTTCT    1440

TATGGATGAG CTCGATCAAC TAGTCACCCA TAATCAAAAA GTTTTATACA ATTTTTTCAA    1500

TTGGCCGTCT CTACCACATT CACGGTTAAT CGTTGTTGCA GTTGCTAATA CGATGGACTT    1560

ACCTGAACGT ATTTTATCAA ATCGCATTTC ATCACGTTTA GGTTTGTCCA GAGTTCCGTT    1620

TGAGCCTTAT ACGCATACTC AGCTAGAAAT AATAATCGCT GCCCGTTTGG AGGCTGTTCG    1680

GGATGACGAT GTTTTTTCTT CAGATGCAAT TCGGTTTGCA GCTCGAAAAG TAGCTGCGGT    1740

TAGCGGTGAT GCTAGAAGAG CCCTTGATAT ATGTCGTCGT GCGTCAGAGC TTGCTGAAAA    1800

CAAAAACGGC AAAGTTACAC CTGGATTAAT TCATCAAGCA ATTTCCGAAA TGACAGCTTC    1860

ACCGCTTCAA AAAGTATTAC GAAATCTCTC ATTCATGCAG AAAGTATTTT TATGTGCTAT    1920

AGTCAATCGT ATGCGCCGGT CTGGATTTGC AGAGTCGTAT GTTTATGAAG TACTTGAAGA    1980

AGCTGAACGG TTGTTGCGAG TCATGACTAC TCCTGATGCT GAAGCAAAAT TTGGCGAGTT    2040

AATATTGAGA AGACCAGAGT TTGGATATGT TTTATCAAGT CTAAGCGAGA ATGGTGTTCT    2100

CTACCTTGAA AATAAAAGTA GTAGGAATGC AAGAGTACGG CTAGCAATTG CAGATGATGA    2160

GATTAAATTG GCATTTCGTG GAGATTCGGA ACTTGCTGGG ATAGCATAAA AGCTATACTT    2220

TTTGGATGAA ATAGGCAATT TACCGATTGA ACAAAGTATA AAAACTTTCC TTACCTTACC    2280

TCTTGAATTT TAAAATGTTT ACTTCTAATT ATAAATTACG ACTTAAATTA TCTTTTAATT    2340

TGCCCATGAW AAMRAARMWR WAAAMRMRWR WWWWAWWMMG ATACTACTAC TTCTATTATT    2400

ACTACCTATA GAGAACCGGG TGACGATACT TATTGTGTTA TCTAGTAAAG TAAAAGAGAA    2460

GTAATAGCTA CTGATTAACC TTAGTTGTAA AATTTCAAAA ATTC                     2504
```

( 2 ) INFORMATION FOR SEQ ID NO:16:

( i ) SEQUENCE CHARACTERISTICS:
        ( A ) LENGTH: 706 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

```
Met Pro Arg Arg Lys Ser Leu Arg Ser Gln Leu Leu Ile Asn Gly Ile
1               5                   10                  15

Asp Lys Ser Leu Leu Ser Asp Asp Ser Ala Asp Ser Ser Asp Ile Asp
            20                  25                  30

Glu Glu Glu Val Tyr Gly Val Trp Thr Glu Glu Pro Phe Gln Lys Glu
        35                  40                  45

Ala Gly Arg Ser Tyr Tyr Arg Ser Leu Lys Lys Asn Asp Val Ile Tyr
    50                  55                  60

Arg Val Gly Asp Asp Ile Thr Val His Asp Gly Asp Ser Ser Phe Tyr
65                  70                  75                  80

Leu Gly Val Ile Cys Lys Leu Tyr Glu Lys Ala Ile Asp Lys His Ser
                85                  90                  95

Gly Lys Lys Tyr Val Glu Ala Ile Trp Tyr Ser Arg Ala Tyr Ala Lys
            100                 105                 110

Arg Met Glu Ile Lys Pro Glu Tyr Leu Leu Pro Asp Arg His Ile Asn
        115                 120                 125

Glu Val Tyr Val Ser Cys Gly Arg Asp Glu Asn Leu Thr Ser Cys Ile
    130                 135                 140
```

```
Ile Glu His Cys Asn Val Tyr Ser Glu Ala Glu Phe Phe Ser Lys Phe
145                 150                 155                 160

Pro Ala Gly Ile Pro Thr Lys Arg Lys Asp Leu Phe Pro Cys Asn Phe
                165                 170                 175

Phe Ile Arg Arg Gly Val His Leu Lys Val Asn Lys Tyr Thr Glu Pro
            180                 185                 190

Leu Asp Trp Ser Tyr Tyr Ala His Asn Leu Glu Arg Ile Glu Asp Leu
            195                 200                 205

Leu Val Glu Met Glu Glu Asn Leu Arg Pro Thr Lys Lys Ser Gly
            210                 215                 220

Ser Arg Gly Arg Gly Arg Pro Arg Lys Tyr Pro Leu Pro Asn Val Glu
225                 230                 235                 240

Ser Lys Glu Ser Ser Ser Lys Val Asn Ser Lys Asp Glu Asn Phe Asp
                245                 250                 255

Leu Gln Asp Asp Ser Glu Ser Ser Glu Asp Asn Leu Thr Ile Gln Pro
            260                 265                 270

Gln Thr Pro Arg Arg Arg His Lys Arg Ser Arg His Asn Ser Ser Asn
        275                 280                 285

Leu Ala Ser Thr Pro Lys Arg Asn Gly Tyr Lys Gln Pro Leu Gln Ile
290                 295                 300

Thr Pro Leu Pro Ile Arg Met Leu Ser Leu Glu Glu Phe Gln Gly Ser
305                 310                 315                 320

Pro His Arg Lys Ala Arg Ala Met Leu His Val Ala Ser Val Pro Ser
                325                 330                 335

Thr Leu Gln Cys Arg Asp Asn Glu Phe Ser Thr Ile Phe Ser Asn Leu
            340                 345                 350

Glu Ser Ala Ile Glu Glu Glu Thr Gly Ala Cys Leu Tyr Ile Ser Gly
            355                 360                 365

Thr Pro Gly Thr Gly Lys Thr Ala Thr Val His Glu Val Ile Trp Asn
370                 375                 380

Leu Gln Glu Leu Ser Arg Glu Gly Gln Leu Pro Glu Phe Ser Phe Cys
385                 390                 395                 400

Glu Ile Asn Gly Met Arg Val Thr Ser Ala Asn Gln Ala Tyr Ser Ile
                405                 410                 415

Leu Trp Glu Ser Leu Thr Gly Glu Arg Val Thr Pro Ile His Ala Met
            420                 425                 430

Asp Leu Leu Asp Asn Arg Phe Thr His Ala Ser Pro Asn Arg Ser Ser
        435                 440                 445

Cys Val Val Leu Met Asp Glu Leu Asp Gln Leu Val Thr His Asn Gln
450                 455                 460

Lys Val Leu Tyr Asn Phe Phe Asn Trp Pro Ser Leu Pro His Ser Arg
465                 470                 475                 480

Leu Ile Val Val Ala Val Ala Asn Thr Met Asp Leu Pro Glu Arg Ile
                485                 490                 495

Leu Ser Asn Arg Ile Ser Ser Arg Leu Gly Leu Ser Arg Val Pro Phe
            500                 505                 510

Glu Pro Tyr Thr His Thr Gln Leu Glu Ile Ile Ile Ala Ala Arg Leu
        515                 520                 525

Glu Ala Val Arg Asp Asp Asp Val Phe Ser Ser Asp Ala Ile Arg Phe
530                 535                 540

Ala Ala Arg Lys Val Ala Ala Val Ser Gly Asp Ala Arg Arg Ala Leu
545                 550                 555                 560

Asp Ile Cys Arg Arg Ala Ser Glu Leu Ala Glu Asn Lys Asn Gly Lys
```

|  | 565 |  |  |  |  | 570 |  |  |  |  | 575 |  |  |
|---|---|---|---|---|---|---|---|---|---|---|---|---|---|

Val Thr Pro Gly Leu Ile His Gln Ala Ile Ser Glu Met Thr Ala Ser
           580                           585                       590

Pro Leu Gln Lys Val Leu Arg Asn Leu Ser Phe Met Gln Lys Val Phe
        595                       600                   605

Leu Cys Ala Ile Val Asn Arg Met Arg Arg Ser Gly Phe Ala Glu Ser
    610                       615                    620

Tyr Val Tyr Glu Val Leu Glu Glu Ala Glu Arg Leu Leu Arg Val Met
625                 630                    635               640

Thr Thr Pro Asp Ala Glu Ala Lys Phe Gly Glu Leu Ile Leu Arg Arg
           645                     650                 655

Pro Glu Phe Gly Tyr Val Leu Ser Ser Leu Ser Glu Asn Gly Val Leu
             660                   665               670

Tyr Leu Glu Asn Lys Ser Ser Arg Asn Ala Arg Val Arg Leu Ala Ile
       675                   680                  685

Ala Asp Asp Glu Ile Lys Leu Ala Phe Arg Gly Asp Ser Glu Leu Ala
    690                     695                  700

Gly Ile
705

( 2 ) INFORMATION FOR SEQ ID NO:17:

( i ) SEQUENCE CHARACTERISTICS:
        ( A ) LENGTH: 3214 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 220..2802

( x i ) SEQUENCE DESCRIPTION: SEQ ID NO:17:

```
CCGGGGCCAC GCGATTGGCG CGAAGTTTTC TTTTCTCCTT CCACCTTCTT TTCATTTCTA        60

GTGAGACACA CGCTTTGGTC CTGGCTTTCG GCCCGTAGTT GTAGAAGGAG CCCTGCTGGT       120

GCAGGTTAGA GGTGCCGCAT CCCCCGGAGC TCTCGAAGTG GAGGCGGTAG GAAACGGAGG       180

GCTTGCGGCT AGCCGGAGGA AGCTTTGGAG CCGGAAGCC ATG GCA CAC TAC CCC         234
                                            Met Ala His Tyr Pro
                                                              440

ACA AGG CTG AAG ACC AGA AAA ACT TAT TCA TGG GTT GGC AGG CCC TTG        282
Thr Arg Leu Lys Thr Arg Lys Thr Tyr Ser Trp Val Gly Arg Pro Leu
            445                 450                 455

TTG GAT CGA AAA CTG CAC TAC CAA ACC TAT AGA GAA ATG TGT GTG AAA        330
Leu Asp Arg Lys Leu His Tyr Gln Thr Tyr Arg Glu Met Cys Val Lys
        460                 465                 470

ACA GAA GGT TGT TCC ACC GAG ATT CAC ATC CAG ATT GGA CAG TTT GTG        378
Thr Glu Gly Cys Ser Thr Glu Ile His Ile Gln Ile Gly Gln Phe Val
    475                 480                 485

TTG ATT GAA GGG GAT GAT GAT GAA AAC CCG TAT GTT GCT AAA TTG CTT        426
Leu Ile Glu Gly Asp Asp Asp Glu Asn Pro Tyr Val Ala Lys Leu Leu
490                 495                 500

GAG TTG TTC GAA GAT GAC TCT GAT CCT CCT CCT AAG AAA CGT GCT CGA        474
Glu Leu Phe Glu Asp Asp Ser Asp Pro Pro Pro Lys Lys Arg Ala Arg
505                 510                 515                 520

GTA CAG TGG TTT GTC CGA TTC TGT GAA GTC CCT GCC TGT AAA CGG CAT        522
Val Gln Trp Phe Val Arg Phe Cys Glu Val Pro Ala Cys Lys Arg His
                525                 530                 535
```

| | | | | | | | | | | | | | | | | |
|---|---|---|---|---|---|---|---|---|---|---|---|---|---|---|---|---|
| TTG | TTG | GGC | CGG | AAG | CCT | GGT | GCA | CAG | GAA | ATA | TTC | TGG | TAT | GAT | TAC | 570 |
| Leu | Leu | Gly | Arg | Lys | Pro | Gly | Ala | Gln | Glu | Ile | Phe | Trp | Tyr | Asp | Tyr | |
| | | | 540 | | | | | 545 | | | | | 550 | | | |
| CCG | GCC | TGT | GAC | AGC | AAC | ATT | AAT | GCG | GAG | ACC | ATC | ATT | GGC | CTT | GTT | 618 |
| Pro | Ala | Cys | Asp | Ser | Asn | Ile | Asn | Ala | Glu | Thr | Ile | Ile | Gly | Leu | Val | |
| | | | 555 | | | | | 560 | | | | | 565 | | | |
| CGG | GTG | ATA | CCT | TTA | GCC | CCA | AAG | GAT | GTG | GTA | CCG | ACG | AAT | CTG | AAA | 666 |
| Arg | Val | Ile | Pro | Leu | Ala | Pro | Lys | Asp | Val | Val | Pro | Thr | Asn | Leu | Lys | |
| | 570 | | | | | 575 | | | | | 580 | | | | | |
| AAT | GAG | AAG | ACA | CTC | TTT | GTG | AAA | CTA | TCC | TGG | AAT | GAG | AAG | AAA | TTC | 714 |
| Asn | Glu | Lys | Thr | Leu | Phe | Val | Lys | Leu | Ser | Trp | Asn | Glu | Lys | Lys | Phe | |
| 585 | | | | | 590 | | | | | 595 | | | | | 600 | |
| AGG | CCA | CTT | TCC | TCA | GAA | CTA | TTT | GCG | GAG | TTG | AAT | AAA | CCA | CAA | GAG | 762 |
| Arg | Pro | Leu | Ser | Ser | Glu | Leu | Phe | Ala | Glu | Leu | Asn | Lys | Pro | Gln | Glu | |
| | | | | 605 | | | | | 610 | | | | | 615 | | |
| AGT | GCA | GCC | AAG | TGC | CAG | AAA | CCC | GTG | AGA | GCC | AAG | AGT | AAG | AGT | GCA | 810 |
| Ser | Ala | Ala | Lys | Cys | Gln | Lys | Pro | Val | Arg | Ala | Lys | Ser | Lys | Ser | Ala | |
| | | | 620 | | | | | 625 | | | | | 630 | | | |
| GAG | AGC | CCT | TCT | TGG | ACC | CCA | GCA | GAA | CAT | GTG | GCC | AAA | AGG | ATT | GAA | 858 |
| Glu | Ser | Pro | Ser | Trp | Thr | Pro | Ala | Glu | His | Val | Ala | Lys | Arg | Ile | Glu | |
| | | | 635 | | | | | 640 | | | | | 645 | | | |
| TCA | AGG | CAC | TCC | GCC | TCC | AAA | TCT | CGC | CAA | ACT | CCT | ACC | CAT | CCT | CTT | 906 |
| Ser | Arg | His | Ser | Ala | Ser | Lys | Ser | Arg | Gln | Thr | Pro | Thr | His | Pro | Leu | |
| | 650 | | | | | 655 | | | | | 660 | | | | | |
| ACC | CCA | AGA | GCC | AGA | AAG | AGG | CTG | GAG | CTT | GGC | AAC | TTA | GGT | AAC | CCT | 954 |
| Thr | Pro | Arg | Ala | Arg | Lys | Arg | Leu | Glu | Leu | Gly | Asn | Leu | Gly | Asn | Pro | |
| 665 | | | | | 670 | | | | | 675 | | | | | 680 | |
| CAG | ATG | TCC | CAG | CAG | ACT | TCA | TGT | GCC | TCC | TTG | GAT | TCT | CCA | GGA | AGA | 1002 |
| Gln | Met | Ser | Gln | Gln | Thr | Ser | Cys | Ala | Ser | Leu | Asp | Ser | Pro | Gly | Arg | |
| | | | | 685 | | | | | 690 | | | | | 695 | | |
| ATA | AAA | CGG | AAA | GTG | GCC | TTC | TCG | GAG | ATC | ACC | TCA | CCT | TCT | AAG | AGA | 1050 |
| Ile | Lys | Arg | Lys | Val | Ala | Phe | Ser | Glu | Ile | Thr | Ser | Pro | Ser | Lys | Arg | |
| | | | 700 | | | | | 705 | | | | | 710 | | | |
| TCT | CAG | CCT | GAT | AAA | CTT | CAA | ACC | TTG | TCT | CCA | GCT | CTG | AAA | GCC | CCA | 1098 |
| Ser | Gln | Pro | Asp | Lys | Leu | Gln | Thr | Leu | Ser | Pro | Ala | Leu | Lys | Ala | Pro | |
| | | 715 | | | | | 720 | | | | | 725 | | | | |
| GAG | AAA | ACC | AGA | GAG | ACT | GGA | CTC | TCT | TAT | ACT | GAG | GAT | GAC | AAG | AAG | 1146 |
| Glu | Lys | Thr | Arg | Glu | Thr | Gly | Leu | Ser | Tyr | Thr | Glu | Asp | Asp | Lys | Lys | |
| | 730 | | | | | 735 | | | | | 740 | | | | | |
| GCT | TCA | CCT | GAA | CAT | CGC | ATA | ATC | CTG | AGA | ACC | CGA | ATT | GCA | GCT | TCG | 1194 |
| Ala | Ser | Pro | Glu | His | Arg | Ile | Ile | Leu | Arg | Thr | Arg | Ile | Ala | Ala | Ser | |
| 745 | | | | | 750 | | | | | 755 | | | | | 760 | |
| AAA | ACC | ATA | GAC | ATT | AGA | GAG | GAG | AGA | ACA | CTT | ACC | CCT | ATC | AGT | GGG | 1242 |
| Lys | Thr | Ile | Asp | Ile | Arg | Glu | Glu | Arg | Thr | Leu | Thr | Pro | Ile | Ser | Gly | |
| | | | | 765 | | | | | 770 | | | | | 775 | | |
| GGA | CAG | AGA | TCT | TCA | GTG | GTG | CCA | TCC | GTG | ATT | CTG | AAA | CCA | GAA | AAC | 1290 |
| Gly | Gln | Arg | Ser | Ser | Val | Val | Pro | Ser | Val | Ile | Leu | Lys | Pro | Glu | Asn | |
| | | | 780 | | | | | 785 | | | | | 790 | | | |
| ATC | AAA | AAG | AGG | GAT | GCA | AAA | GAA | GCA | AAA | GCC | CAG | AAT | GAA | GCG | ACC | 1338 |
| Ile | Lys | Lys | Arg | Asp | Ala | Lys | Glu | Ala | Lys | Ala | Gln | Asn | Glu | Ala | Thr | |
| | | | 795 | | | | | 800 | | | | | 805 | | | |
| TCT | ACT | CCC | CAT | CGT | ATC | CGC | AGA | AAG | AGT | TCT | GTC | TTG | ACT | ATG | AAT | 1386 |
| Ser | Thr | Pro | His | Arg | Ile | Arg | Arg | Lys | Ser | Ser | Val | Leu | Thr | Met | Asn | |
| | 810 | | | | | 815 | | | | | 820 | | | | | |
| CGG | ATT | AGG | CAG | CAG | CTT | CGG | TTT | CTA | GGT | AAT | AGT | AAA | AGT | GAC | CAA | 1434 |
| Arg | Ile | Arg | Gln | Gln | Leu | Arg | Phe | Leu | Gly | Asn | Ser | Lys | Ser | Asp | Gln | |
| 825 | | | | | 830 | | | | | 835 | | | | | 840 | |
| GAA | GAG | AAA | GAG | ATT | CTG | CCA | GCA | GCA | GAG | ATT | TCA | GAC | TCT | AGC | AGT | 1482 |
| Glu | Glu | Lys | Glu | Ile | Leu | Pro | Ala | Ala | Glu | Ile | Ser | Asp | Ser | Ser | Ser | |
| | | | | 845 | | | | | 850 | | | | | 855 | | |

| | |
|---|---|
| GAC GAA GAA GAG GCT TCC ACA CCG CCC CTT CCA AGG AGA GCA CCC AGA<br>Asp Glu Glu Glu Ala Ser Thr Pro Pro Leu Pro Arg Arg Ala Pro Arg<br>                860                           865                    870 | 1530 |
| ACT GTG TCC AGG AAC CTG CGA TCT TCC TTG AAG TCA TCC TTA CAT ACC<br>Thr Val Ser Arg Asn Leu Arg Ser Ser Leu Lys Ser Ser Leu His Thr<br>         875                       880                    885 | 1578 |
| CTC ACG AAG GTG CCA AAG AAG AGT CTC AAG CCT AGA ACG CCA CGT TGT<br>Leu Thr Lys Val Pro Lys Lys Ser Leu Lys Pro Arg Thr Pro Arg Cys<br>    890                        895                    900 | 1626 |
| GCC GCT CCT CAG ATC CGT AGT CGA AGC CTG GCT GCC CAG GAG CCA GCC<br>Ala Ala Pro Gln Ile Arg Ser Arg Ser Leu Ala Ala Gln Glu Pro Ala<br>905                    910                    915                    920 | 1674 |
| AGT GTG CTG GAG GAA GCC CGA CTG AGG CTG CAT GTT TCT GCT GTA CCT<br>Ser Val Leu Glu Glu Ala Arg Leu Arg Leu His Val Ser Ala Val Pro<br>                  925                        930                    935 | 1722 |
| GAG TCT CTT CCC TGT CGG GAA CAG GAA TTC CAA GAC ATC TAC AAT TTT<br>Glu Ser Leu Pro Cys Arg Glu Gln Glu Phe Gln Asp Ile Tyr Asn Phe<br>            940                        945                    950 | 1770 |
| GTG GAA AGC AAA CTC CTT GAC CAT ACC GGA GGG TGC ATG TAC ATC TCC<br>Val Glu Ser Lys Leu Leu Asp His Thr Gly Gly Cys Met Tyr Ile Ser<br>        955                        960                    965 | 1818 |
| GGT GTC CCT GGG ACA GGG AAG ACT GCC ACT GTT CAT GAA GTG ATA CGC<br>Gly Val Pro Gly Thr Gly Lys Thr Ala Thr Val His Glu Val Ile Arg<br>970                    975                    980 | 1866 |
| TGC CTG CAG CAG GCA GCC CAA GCC AAT GAT GTT CCT CCC TTT CAA TAC<br>Cys Leu Gln Gln Ala Ala Gln Ala Asn Asp Val Pro Pro Phe Gln Tyr<br>985                    990                    995                  1000 | 1914 |
| ATT GAG GTC AAT GGC ATG AAG CTG ACG GAG CCC CAC CAA GTC TAT GTG<br>Ile Glu Val Asn Gly Met Lys Leu Thr Glu Pro His Gln Val Tyr Val<br>                  1005                      1010                  1015 | 1962 |
| CAC ATC TTG CAG AAG CTA ACA GGC CAA AAA GCA ACA GCC AAC CAT GCG<br>His Ile Leu Gln Lys Leu Thr Gly Gln Lys Ala Thr Ala Asn His Ala<br>            1020                      1025                  1030 | 2010 |
| GCA GAA CTG CTG GCA AAG CAA TTC TGC ACC CGA GGG TCA CCT CAG GAA<br>Ala Glu Leu Leu Ala Lys Gln Phe Cys Thr Arg Gly Ser Pro Gln Glu<br>        1035                      1040                    1045 | 2058 |
| ACC ACC GTC CTG CTT GTG GAT GAG CTC GAC CTT CTG TGG ACT CAC AAA<br>Thr Thr Val Leu Leu Val Asp Glu Leu Asp Leu Leu Trp Thr His Lys<br>1050                      1055                      1060 | 2106 |
| CAA GAC ATA ATG TAC AAT CTC TTT GAC TGG CCC ACT CAT AAG GAG GCC<br>Gln Asp Ile Met Tyr Asn Leu Phe Asp Trp Pro Thr His Lys Glu Ala<br>1065                    1070                      1075                  1080 | 2154 |
| CGG CTT GTG GTC CTG GCA ATT GCC AAC ACA ATG GAC CTG CCA GAG CGA<br>Arg Leu Val Val Leu Ala Ile Ala Asn Thr Met Asp Leu Pro Glu Arg<br>                  1085                      1090                  1095 | 2202 |
| ATC ATG ATG AAC CGG GTG TCC AGC CGA CTG GGT CTT ACC AGG ATG TGC<br>Ile Met Met Asn Arg Val Ser Ser Arg Leu Gly Leu Thr Arg Met Cys<br>            1100                      1105                  1110 | 2250 |
| TTC CAG CCC TAT ACA TAT AGC CAG CTG CAG CAG ATC CTA AGG TCC CGG<br>Phe Gln Pro Tyr Thr Tyr Ser Gln Leu Gln Gln Ile Leu Arg Ser Arg<br>        1115                      1120                    1125 | 2298 |
| CTC AAG CAT CTA AAG GCC TTT GAA GAT GAT GCC ATC CAG CTG GTA GCC<br>Leu Lys His Leu Lys Ala Phe Glu Asp Asp Ala Ile Gln Leu Val Ala<br>        1130                      1135                    1140 | 2346 |
| AGG AAG GTA GCA GCA CTG TCT GGA GAT GCA CGA CGG TGC CTG GAC ATC<br>Arg Lys Val Ala Ala Leu Ser Gly Asp Ala Arg Arg Cys Leu Asp Ile<br>1145                      1150                      1155                  1160 | 2394 |
| TGC AGG CGT GCC ACA GAG ATC TGT GAG TTC TCC CAG CAG AAG CCT GAC<br>Cys Arg Arg Ala Thr Glu Ile Cys Glu Phe Ser Gln Gln Lys Pro Asp<br>            1165                      1170                  1175 | 2442 |

-continued

```
TCC CCT GGC CTG GTC ACC ATA GCC CAC TCA ATG GAA GCT GTG GAT GAG          2490
Ser Pro Gly Leu Val Thr Ile Ala His Ser Met Glu Ala Val Asp Glu
            1180            1185                1190

ATG TTT TCA TCA TCA TAC ATC ACG GCC ATC AAA AAT TCC TCT GTT CTG          2538
Met Phe Ser Ser Ser Tyr Ile Thr Ala Ile Lys Asn Ser Ser Val Leu
            1195            1200                1205

GAA CAG AGC TTC CTG AGA GCC ATC CTC GCA GAG TTC CGT CGA TCA GGA          2586
Glu Gln Ser Phe Leu Arg Ala Ile Leu Ala Glu Phe Arg Arg Ser Gly
            1210            1215                1220

CTG GAG GAA GCC ACG TTT CAA CAG ATA TAT AGT CAA CAT GTG GCA CTG          2634
Leu Glu Glu Ala Thr Phe Gln Gln Ile Tyr Ser Gln His Val Ala Leu
1225            1230            1235                1240

TGC AGA ATG GAG GGA CTG CCG TAC CCC ACC ATG TCA GAG ACC ATG GCC          2682
Cys Arg Met Glu Gly Leu Pro Tyr Pro Thr Met Ser Glu Thr Met Ala
                1245            1250                1255

GTG TGT TCT CAC CTG GGC TCC TGT CGC CTC CTG CTT GTG GAG CCC AGC          2730
Val Cys Ser His Leu Gly Ser Cys Arg Leu Leu Leu Val Glu Pro Ser
            1260            1265                1270

AGG AAC GAT CTG CTC CTT CGG GTG CGG CTC AAC GTC AGC CAG GAT GAT          2778
Arg Asn Asp Leu Leu Leu Arg Val Arg Leu Asn Val Ser Gln Asp Asp
            1275            1280                1285

GTG CTG TAT GCG CTG AAA GAC GAG TAAAGGGCT TCACAAGTTA AAAGACTGGG          2832
Val Leu Tyr Ala Leu Lys Asp Glu
            1290            1295

GTCTTGCTGG GTTTTGTTTT TTGAGACAGG GTCTTGCTCT GTCGCCCAGG CTGGAGTGCA        2892

GTGGCACGAT CATGGCTCAC TGCAGCCTTG ACTTCTCAGG CTTAGGTGAC CCCCCAACCT        2952

CATCCTCCCA GGTGGCTGAA ACTACAGGCA CATGCCACCA TGCCCAGCTG ATTTTTTGTA        3012

GAGACAGGGC TTCACCATGT TGCCAAGCTA GTCTACAAAG CATCTGATTT TGGAAGTACA        3072

TGGAATTGTT GTAACAAAGT ATATTGAATG GAAATGGCTC TCATGTATTT TGGAATTTTC        3132

CATTAAATAA TTTGCTTTTT AAAAAAAAAA AAAAAAAAAA AAAAAAAAAA AAAAAAAAAA        3192

AAAAAAAAAA AAAAAAAAAA AA                                                 3214
```

( 2 ) INFORMATION FOR SEQ ID NO:18:

( i ) SEQUENCE CHARACTERISTICS:
        ( A ) LENGTH: 861 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Met Ala His Tyr Pro Thr Arg Leu Lys Thr Arg Lys Thr Tyr Ser Trp
 1               5                  10                  15

Val Gly Arg Pro Leu Leu Asp Arg Lys Leu His Tyr Gln Thr Tyr Arg
                20                  25                  30

Glu Met Cys Val Lys Thr Glu Gly Cys Ser Thr Glu Ile His Ile Gln
            35                  40                  45

Ile Gly Gln Phe Val Leu Ile Glu Gly Asp Asp Glu Asn Pro Tyr
    50                  55                  60

Val Ala Lys Leu Leu Glu Leu Phe Glu Asp Asp Ser Asp Pro Pro Pro
65                  70                  75                  80

Lys Lys Arg Ala Arg Val Gln Trp Phe Val Arg Phe Cys Glu Val Pro
                85                  90                  95

Ala Cys Lys Arg His Leu Leu Gly Arg Lys Pro Gly Ala Gln Glu Ile
            100                 105                 110

Phe Trp Tyr Asp Tyr Pro Ala Cys Asp Ser Asn Ile Asn Ala Glu Thr
```

|     |     |     | 115 |     |     |     | 120 |     |     |     | 125 |     |     |     |
| --- | --- | --- | --- | --- | --- | --- | --- | --- | --- | --- | --- | --- | --- | --- |
| Ile | Ile | Gly | Leu | Val | Arg | Val | Ile | Pro | Leu | Ala | Pro | Lys | Asp | Val | Val |
|     | 130 |     |     |     |     | 135 |     |     |     |     | 140 |     |     |     |     |
| Pro | Thr | Asn | Leu | Lys | Asn | Glu | Lys | Thr | Leu | Phe | Val | Lys | Leu | Ser | Trp |
| 145 |     |     |     |     | 150 |     |     |     |     | 155 |     |     |     |     | 160 |
| Asn | Glu | Lys | Lys | Phe | Arg | Pro | Leu | Ser | Ser | Glu | Leu | Phe | Ala | Glu | Leu |
|     |     |     |     | 165 |     |     |     |     | 170 |     |     |     |     | 175 |     |
| Asn | Lys | Pro | Gln | Glu | Ser | Ala | Ala | Lys | Cys | Gln | Lys | Pro | Val | Arg | Ala |
|     |     |     | 180 |     |     |     |     | 185 |     |     |     |     | 190 |     |     |
| Lys | Ser | Lys | Ser | Ala | Glu | Ser | Pro | Ser | Trp | Thr | Pro | Ala | Glu | His | Val |
|     |     | 195 |     |     |     |     | 200 |     |     |     |     | 205 |     |     |     |
| Ala | Lys | Arg | Ile | Glu | Ser | Arg | His | Ser | Ala | Ser | Lys | Ser | Arg | Gln | Thr |
|     | 210 |     |     |     |     | 215 |     |     |     |     | 220 |     |     |     |     |
| Pro | Thr | His | Pro | Leu | Thr | Pro | Arg | Ala | Arg | Lys | Arg | Leu | Glu | Leu | Gly |
| 225 |     |     |     |     | 230 |     |     |     |     | 235 |     |     |     |     | 240 |
| Asn | Leu | Gly | Asn | Pro | Gln | Met | Ser | Gln | Gln | Thr | Ser | Cys | Ala | Ser | Leu |
|     |     |     |     | 245 |     |     |     |     | 250 |     |     |     |     | 255 |     |
| Asp | Ser | Pro | Gly | Arg | Ile | Lys | Arg | Lys | Val | Ala | Phe | Ser | Glu | Ile | Thr |
|     |     |     | 260 |     |     |     |     | 265 |     |     |     |     | 270 |     |     |
| Ser | Pro | Ser | Lys | Arg | Ser | Gln | Pro | Asp | Lys | Leu | Gln | Thr | Leu | Ser | Pro |
|     |     | 275 |     |     |     |     | 280 |     |     |     |     | 285 |     |     |     |
| Ala | Leu | Lys | Ala | Pro | Glu | Lys | Thr | Arg | Glu | Thr | Gly | Leu | Ser | Tyr | Thr |
|     | 290 |     |     |     |     | 295 |     |     |     |     | 300 |     |     |     |     |
| Glu | Asp | Asp | Lys | Lys | Ala | Ser | Pro | Glu | His | Arg | Ile | Ile | Leu | Arg | Thr |
| 305 |     |     |     |     | 310 |     |     |     |     | 315 |     |     |     |     | 320 |
| Arg | Ile | Ala | Ala | Ser | Lys | Thr | Ile | Asp | Ile | Arg | Glu | Glu | Arg | Thr | Leu |
|     |     |     |     | 325 |     |     |     |     | 330 |     |     |     |     | 335 |     |
| Thr | Pro | Ile | Ser | Gly | Gly | Gln | Arg | Ser | Ser | Val | Val | Pro | Ser | Val | Ile |
|     |     |     | 340 |     |     |     |     | 345 |     |     |     |     | 350 |     |     |
| Leu | Lys | Pro | Glu | Asn | Ile | Lys | Lys | Arg | Asp | Ala | Lys | Glu | Ala | Lys | Ala |
|     |     | 355 |     |     |     |     | 360 |     |     |     |     | 365 |     |     |     |
| Gln | Asn | Glu | Ala | Thr | Ser | Thr | Pro | His | Arg | Ile | Arg | Arg | Lys | Ser | Ser |
|     | 370 |     |     |     |     | 375 |     |     |     |     | 380 |     |     |     |     |
| Val | Leu | Thr | Met | Asn | Arg | Ile | Arg | Gln | Gln | Leu | Arg | Phe | Leu | Gly | Asn |
| 385 |     |     |     |     | 390 |     |     |     |     | 395 |     |     |     |     | 400 |
| Ser | Lys | Ser | Asp | Gln | Glu | Glu | Lys | Glu | Ile | Leu | Pro | Ala | Ala | Glu | Ile |
|     |     |     |     | 405 |     |     |     |     | 410 |     |     |     |     | 415 |     |
| Ser | Asp | Ser | Ser | Ser | Asp | Glu | Glu | Ala | Ser | Thr | Pro | Pro | Leu | Pro |
|     |     |     | 420 |     |     |     |     | 425 |     |     |     |     | 430 |     |     |
| Arg | Arg | Ala | Pro | Arg | Thr | Val | Ser | Arg | Asn | Leu | Arg | Ser | Ser | Leu | Lys |
|     |     | 435 |     |     |     |     | 440 |     |     |     |     | 445 |     |     |     |
| Ser | Ser | Leu | His | Thr | Leu | Thr | Lys | Val | Pro | Lys | Lys | Ser | Leu | Lys | Pro |
|     | 450 |     |     |     |     | 455 |     |     |     |     | 460 |     |     |     |     |
| Arg | Thr | Pro | Arg | Cys | Ala | Ala | Pro | Gln | Ile | Arg | Ser | Arg | Ser | Leu | Ala |
| 465 |     |     |     |     | 470 |     |     |     |     | 475 |     |     |     |     | 480 |
| Ala | Gln | Glu | Pro | Ala | Ser | Val | Leu | Glu | Glu | Ala | Arg | Leu | Arg | Leu | His |
|     |     |     |     | 485 |     |     |     |     | 490 |     |     |     |     | 495 |     |
| Val | Ser | Ala | Val | Pro | Glu | Ser | Leu | Pro | Cys | Arg | Glu | Gln | Glu | Phe | Gln |
|     |     |     | 500 |     |     |     |     | 505 |     |     |     |     | 510 |     |     |
| Asp | Ile | Tyr | Asn | Phe | Val | Glu | Ser | Lys | Leu | Leu | Asp | His | Thr | Gly | Gly |
|     |     |     | 515 |     |     |     |     | 520 |     |     |     |     | 525 |     |     |
| Cys | Met | Tyr | Ile | Ser | Gly | Val | Pro | Gly | Thr | Gly | Lys | Thr | Ala | Thr | Val |
|     |     |     | 530 |     |     |     |     | 535 |     |     |     |     | 540 |     |     |

| | | | | | | | | | | | | | | |
|---|---|---|---|---|---|---|---|---|---|---|---|---|---|---|
| His 545 | Glu | Val | Ile | Arg | Cys 550 | Leu | Gln | Gln | Ala | Ala 555 | Gln | Ala | Asn | Asp | Val 560 |
| Pro | Pro | Phe | Gln | Tyr 565 | Ile | Glu | Val | Asn | Gly 570 | Met | Lys | Leu | Thr | Glu 575 | Pro |
| His | Gln | Val | Tyr 580 | Val | His | Ile | Leu | Gln 585 | Lys | Leu | Thr | Gly | Gln 590 | Lys | Ala |
| Thr | Ala | Asn 595 | His | Ala | Ala | Glu | Leu 600 | Leu | Ala | Lys | Gln | Phe 605 | Cys | Thr | Arg |
| Gly | Ser 610 | Pro | Gln | Glu | Thr | Thr 615 | Val | Leu | Leu | Val | Asp 620 | Glu | Leu | Asp | Leu |
| Leu 625 | Trp | Thr | His | Lys | Gln 630 | Asp | Ile | Met | Tyr | Asn 635 | Leu | Phe | Asp | Trp | Pro 640 |
| Thr | His | Lys | Glu | Ala 645 | Arg | Leu | Val | Val | Leu 650 | Ala | Ile | Ala | Asn | Thr 655 | Met |
| Asp | Leu | Pro | Glu 660 | Arg | Ile | Met | Met | Asn 665 | Arg | Val | Ser | Ser | Arg 670 | Leu | Gly |
| Leu | Thr | Arg 675 | Met | Cys | Phe | Gln | Pro 680 | Tyr | Thr | Tyr | Ser | Gln 685 | Leu | Gln | Gln |
| Ile 690 | Leu | Arg | Ser | Arg | Leu 695 | Lys | His | Leu | Lys | Ala 700 | Phe | Glu | Asp | Asp | Ala |
| Ile 705 | Gln | Leu | Val | Ala | Arg 710 | Lys | Val | Ala | Ala | Leu 715 | Ser | Gly | Asp | Ala | Arg 720 |
| Arg | Cys | Leu | Asp | Ile 725 | Cys | Arg | Arg | Ala | Thr 730 | Glu | Ile | Cys | Glu | Phe 735 | Ser |
| Gln | Gln | Lys | Pro 740 | Asp | Ser | Pro | Gly | Leu 745 | Val | Thr | Ile | Ala | His 750 | Ser | Met |
| Glu | Ala | Val 755 | Asp | Glu | Met | Phe | Ser 760 | Ser | Ser | Tyr | Ile | Thr 765 | Ala | Ile | Lys |
| Asn | Ser 770 | Ser | Val | Leu | Glu | Gln 775 | Ser | Phe | Leu | Arg | Ala 780 | Ile | Leu | Ala | Glu |
| Phe 785 | Arg | Arg | Ser | Gly | Leu 790 | Glu | Glu | Ala | Thr | Phe 795 | Gln | Gln | Ile | Tyr | Ser 800 |
| Gln | His | Val | Ala | Leu 805 | Cys | Arg | Met | Glu | Gly 810 | Leu | Pro | Tyr | Pro | Thr 815 | Met |
| Ser | Glu | Thr | Met 820 | Ala | Val | Cys | Ser | His 825 | Leu | Gly | Ser | Cys | Arg 830 | Leu | Leu |
| Leu | Val | Glu 835 | Pro | Ser | Arg | Asn | Asp 840 | Leu | Leu | Leu | Arg | Val 845 | Arg | Leu | Asn |
| Val | Ser 850 | Gln | Asp | Asp | Val | Leu 855 | Tyr | Ala | Leu | Lys | Asp 860 | Glu | | | |

( 2 ) INFORMATION FOR SEQ ID NO:19:

( i ) SEQUENCE CHARACTERISTICS:
        ( A ) LENGTH: 1480 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 277..1365

( x i ) SEQUENCE DESCRIPTION: SEQ ID NO:19:

```
TGAATCGGGA ATCTGATTCA TATGTTTGGG GTTAATAGT CTCAGCTCAA ATAAATCTAG      60

GTTAAACTGT GTGGATCGAT TCATATATCC TCCGTCAAAA CCAAAACCAA ACCGATTTGT    120
```

```
CATAATTTTT TCTTATCATC CACTTTCATT GGCTAGAGGG ACATTGTAAC GGTGTCGTCG      180

TCGCCAAACG ATTTGCCTCT TCCTAAAGGA GATTCTTTCC TACATAGGAA TTGAGTTTAA      240

GGTGGAATTC TTCTGTTATT TTGTTGTTGC ACGAAA ATG GAG GAC ATT GAG AAC        294
                                        Met Glu Asp Ile Glu Asn
                                                            865

ATA GAA GAA GAT GAG TAT GGG TTT TCA AGA AAC TAC TTC TTG GCA AAA        342
Ile Glu Glu Asp Glu Tyr Gly Phe Ser Arg Asn Tyr Phe Leu Ala Lys
        870                 875                 880

GAA TTG GGT GGG GCG AGT AAG CGT TCT GCC CAC AAG CTC TCT GAT ATA        390
Glu Leu Gly Gly Ala Ser Lys Arg Ser Ala His Lys Leu Ser Asp Ile
885                 890                 895

CAT ATT GTT GAT GAG CAG GAG CTT AGA GAA ACG GCT TCT ACA ATT GAA        438
His Ile Val Asp Glu Gln Glu Leu Arg Glu Thr Ala Ser Thr Ile Glu
900                 905                 910                 915

ATG AAG CAC TCG AAA GAG ATA TCT GAG CTT ATG AGT GAT TAC AAG ACT        486
Met Lys His Ser Lys Glu Ile Ser Glu Leu Met Ser Asp Tyr Lys Thr
                920                 925                 930

ATG TAC TCA AAG TGG GTC TTT GAG CTC AGG TGT GGC TTT GGC CTT CTA        534
Met Tyr Ser Lys Trp Val Phe Glu Leu Arg Cys Gly Phe Gly Leu Leu
            935                 940                 945

ATG TAT GGC TTT GGA TCT AAG AAA GCT TTA GTT GAA GAT TTT GCT TCT        582
Met Tyr Gly Phe Gly Ser Lys Lys Ala Leu Val Glu Asp Phe Ala Ser
        950                 955                 960

GCT TCT TTG ACT GAC TAT TCT GTT GTG GTC ATC AAT GGC TAC CTC CCT        630
Ala Ser Leu Thr Asp Tyr Ser Val Val Val Ile Asn Gly Tyr Leu Pro
965                 970                 975

TCC GTA AAT CTA AAG CAG GTT CTT TTG GCA TTA GCT GAA CTT CTA TCC        678
Ser Val Asn Leu Lys Gln Val Leu Leu Ala Leu Ala Glu Leu Leu Ser
980                 985                 990                 995

GAG CTT TTG AAA TGT AAA AGA AAG AGT TCC GGG AGT TTG TCT AAA GGT        726
Glu Leu Leu Lys Cys Lys Arg Lys Ser Ser Gly Ser Leu Ser Lys Gly
                1000                1005                1010

CAA GAA ACA TTT CCT TCA CGC TCC ATG GAT GAT ATT CTT TCC TTT CTA        774
Gln Glu Thr Phe Pro Ser Arg Ser Met Asp Asp Ile Leu Ser Phe Leu
            1015                1020                1025

CAT GGT CCA CAG TCT GGA GAT AAA GAC TGC TTC ATA TGC GTT GTT GTT        822
His Gly Pro Gln Ser Gly Asp Lys Asp Cys Phe Ile Cys Val Val Val
        1030                1035                1040

CAT AAC ATT GAC GGC CCT GCT CTA AGA GAT CCC GAA TCA CAA CAA ACT        870
His Asn Ile Asp Gly Pro Ala Leu Arg Asp Pro Glu Ser Gln Gln Thr
1045                1050                1055

CTT GCC CGG CTT TCT TCT TGT TCA CAC ATA CGC TTG GTT GCC TCT ATT        918
Leu Ala Arg Leu Ser Ser Cys Ser His Ile Arg Leu Val Ala Ser Ile
1060                1065                1070                1075

GAC CAT GTC AAC GCT CCA TTA TTG TGG GAC AAG AAA ATG GTG CAC AAA        966
Asp His Val Asn Ala Pro Leu Leu Trp Asp Lys Lys Met Val His Lys
                1080                1085                1090

CAG TTT AAC TGG CTA TGG CAC CAT GTT CCA ACA TTT GCA CCA TAC AAT        1014
Gln Phe Asn Trp Leu Trp His His Val Pro Thr Phe Ala Pro Tyr Asn
            1095                1100                1105

GTC GAA GGT GTA TTC TTC CCG TTG GTT CTT GCA CAG GGA AGC ACA GCC        1062
Val Glu Gly Val Phe Phe Pro Leu Val Leu Ala Gln Gly Ser Thr Ala
        1110                1115                1120

CAA ACC GCC AAA ACA GCA GCC ATT GTT TTA CAG AGT TTA ACA CCA AAC        1110
Gln Thr Ala Lys Thr Ala Ala Ile Val Leu Gln Ser Leu Thr Pro Asn
1125                1130                1135

GGT CAG AAT GTC TTC AAG ATT CTT GCT GAG TAC CAA CTT TCA CAC CCA        1158
Gly Gln Asn Val Phe Lys Ile Leu Ala Glu Tyr Gln Leu Ser His Pro
1140                1145                1150                1155
```

```
GAT GAA GAT GGG ATG CCC ACT GAT GAT CTG TAT TCA GCG TCT CGG GAA    1206
Asp Glu Asp Gly Met Pro Thr Asp Asp Leu Tyr Ser Ala Ser Arg Glu
            1160                1165                1170

CGC TTC TTT GTG AGC AGT CAA GTG ACT TTA AAC TCT CAT CTC ACG GAA    1254
Arg Phe Phe Val Ser Ser Gln Val Thr Leu Asn Ser His Leu Thr Glu
            1175                1180                1185

TTT AAA GAC CAC GAA CTG GTT AAG ACC AAG AGA AAC TCC GAT GGT CAA    1302
Phe Lys Asp His Glu Leu Val Lys Thr Lys Arg Asn Ser Asp Gly Gln
        1190                1195                1200

GAG TGT TTG AAT ATA CCG CTC ACT TCG GAT GCA ATT CGA CAG CTT TTG    1350
Glu Cys Leu Asn Ile Pro Leu Thr Ser Asp Ala Ile Arg Gln Leu Leu
    1205                1210                1215

CTT GAT CTC AAT CAG TAGCCTGAAA TTGTATTTCT GATATGATTC ATTTTATTG      1405
Leu Asp Leu Asn Gln
1220

CTTGAACGAG TTATTATAGT TCACACAGTT TACATGTTTA ATTGAATGTT ATAGTCAGCA  1465

CTCACAGCTC TTATT                                                   1480
```

( 2 ) INFORMATION FOR SEQ ID NO:20:

( i ) SEQUENCE CHARACTERISTICS:
        ( A ) LENGTH: 363 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Met Glu Asp Ile Glu Asn Ile Glu Glu Asp Glu Tyr Gly Phe Ser Arg
 1               5                  10                  15

Asn Tyr Phe Leu Ala Lys Glu Leu Gly Gly Ala Ser Lys Arg Ser Ala
                20                  25                  30

His Lys Leu Ser Asp Ile His Ile Val Asp Glu Gln Glu Leu Arg Glu
                35                  40                  45

Thr Ala Ser Thr Ile Glu Met Lys His Ser Lys Glu Ile Ser Glu Leu
        50                  55                  60

Met Ser Asp Tyr Lys Thr Met Tyr Ser Lys Trp Val Phe Glu Leu Arg
65                  70                  75                  80

Cys Gly Phe Gly Leu Leu Met Tyr Gly Phe Gly Ser Lys Lys Ala Leu
                85                  90                  95

Val Glu Asp Phe Ala Ser Ala Ser Leu Thr Asp Tyr Ser Val Val
                100                 105                 110

Ile Asn Gly Tyr Leu Pro Ser Val Asn Leu Lys Gln Val Leu Leu Ala
                115                 120                 125

Leu Ala Glu Leu Leu Ser Glu Leu Leu Lys Cys Lys Arg Lys Ser Ser
        130                 135                 140

Gly Ser Leu Ser Lys Gly Gln Glu Thr Phe Pro Ser Arg Ser Met Asp
145                 150                 155                 160

Asp Ile Leu Ser Phe Leu His Gly Pro Gln Ser Gly Asp Lys Asp Cys
                165                 170                 175

Phe Ile Cys Val Val Val His Asn Ile Asp Gly Pro Ala Leu Arg Asp
                180                 185                 190

Pro Glu Ser Gln Gln Thr Leu Ala Arg Leu Ser Ser Cys Ser His Ile
                195                 200                 205

Arg Leu Val Ala Ser Ile Asp His Val Asn Ala Pro Leu Leu Trp Asp
        210                 215                 220

Lys Lys Met Val His Lys Gln Phe Asn Trp Leu Trp His His Val Pro
```

5,589,341

```
225                         230                        235                        240
Thr  Phe  Ala  Pro  Tyr  Asn  Val  Glu  Gly  Val  Phe  Phe  Pro  Leu  Val  Leu
                    245                      250                      255

Ala  Gln  Gly  Ser  Thr  Ala  Gln  Thr  Ala  Lys  Thr  Ala  Ala  Ile  Val  Leu
               260                      265                      270

Gln  Ser  Leu  Thr  Pro  Asn  Gly  Gln  Asn  Val  Phe  Lys  Ile  Leu  Ala  Glu
          275                      280                      285

Tyr  Gln  Leu  Ser  His  Pro  Asp  Glu  Asp  Gly  Met  Pro  Thr  Asp  Asp  Leu
     290                      295                      300

Tyr  Ser  Ala  Ser  Arg  Glu  Arg  Phe  Phe  Val  Ser  Ser  Gln  Val  Thr  Leu
305                      310                      315                      320

Asn  Ser  His  Leu  Thr  Glu  Phe  Lys  Asp  His  Glu  Leu  Val  Lys  Thr  Lys
                    325                      330                      335

Arg  Asn  Ser  Asp  Gly  Gln  Glu  Cys  Leu  Asn  Ile  Pro  Leu  Thr  Ser  Asp
               340                      345                      350

Ala  Ile  Arg  Gln  Leu  Leu  Leu  Asp  Leu  Asn  Gln
               355                      360
```

( 2 ) INFORMATION FOR SEQ ID NO:21:

( i ) SEQUENCE CHARACTERISTICS:
        ( A ) LENGTH: 1676 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 13..1302

( x i ) SEQUENCE DESCRIPTION: SEQ ID NO:21:

```
AAGTTTGAGA AA  ATG  CCA  CGG  CCA  AAA  ATT  TTG  AAA  CGA  GCA  ACT  GTC        48
               Met  Pro  Arg  Pro  Lys  Ile  Leu  Lys  Arg  Ala  Thr  Val
                    365                      370                      375

CAG  CCC  AGT  GCC  GCC  GTT  CCT  GTG  AAA  AAA  TCG  ACT  CCA  GAA  AAA  GAA    96
Gln  Pro  Ser  Ala  Ala  Val  Pro  Val  Lys  Lys  Ser  Thr  Pro  Glu  Lys  Glu
               380                      385                      390

GGA  TCC  AGA  CAG  AAA  AAG  ACG  AAT  GGA  AAA  GAG  AAT  GCT  TCT  AGA  AAT   144
Gly  Ser  Arg  Gln  Lys  Lys  Thr  Asn  Gly  Lys  Glu  Asn  Ala  Ser  Arg  Asn
               395                      400                      405

TTG  CAA  TCA  AAT  TTA  GAA  GAA  GAT  TTG  GAA  CAA  CTG  GGC  TTC  GAG  GAT   192
Leu  Gln  Ser  Asn  Leu  Glu  Glu  Asp  Leu  Glu  Gln  Leu  Gly  Phe  Glu  Asp
               410                      415                      420

GAA  ACT  GTA  TCA  ATG  GCT  CAA  TCA  GCA  ATC  GAA  AAT  TAC  TTT  ATG  CAA   240
Glu  Thr  Val  Ser  Met  Ala  Gln  Ser  Ala  Ile  Glu  Asn  Tyr  Phe  Met  Gln
     425                      430                      435

GGA  AAA  TCG  GCG  TCA  GAA  CGA  ATG  AAT  AAT  GCG  AAA  TCC  CGT  CGT  GGA   288
Gly  Lys  Ser  Ala  Ser  Glu  Arg  Met  Asn  Asn  Ala  Lys  Ser  Arg  Arg  Gly
440                      445                      450                      455

AGA  CGT  GCT  GGA  AAT  GGA  AAT  ACT  GAA  GAA  ATT  GAG  GAA  GAC  GAT  GAG   336
Arg  Arg  Ala  Gly  Asn  Gly  Asn  Thr  Glu  Glu  Ile  Glu  Glu  Asp  Asp  Glu
               460                      465                      470

ATC  AGT  AAT  GCT  ATC  ACT  GAT  TTC  ACA  AAA  TGT  GAT  CTC  CCT  GGA  CTT   384
Ile  Ser  Asn  Ala  Ile  Thr  Asp  Phe  Thr  Lys  Cys  Asp  Leu  Pro  Gly  Leu
               475                      480                      485

CGA  AAT  TAT  ATT  ACC  AAA  AAA  GAT  AAC  ACG  GAA  TTC  GAA  AAA  CGA  TTG   432
Arg  Asn  Tyr  Ile  Thr  Lys  Lys  Asp  Asn  Thr  Glu  Phe  Glu  Lys  Arg  Leu
               490                      495                      500

GAG  CAT  CTC  GCG  GAT  AAT  GAT  TTC  GGA  AAA  TGG  AAG  CTT  TAC  CTA  GCA   480
```

-continued

```
                Glu  His  Leu  Ala  Asp  Asn  Asp  Phe  Gly  Lys  Trp  Lys  Leu  Tyr  Leu  Ala
                505                     510                          515

GCT  GGA  TTT  AAT  ATT  CTT  TTG  CAC  GGT  GTC  GGT  TCG  AAG  CGT  GAT  GTT               528
Ala  Gly  Phe  Asn  Ile  Leu  Leu  His  Gly  Val  Gly  Ser  Lys  Arg  Asp  Val
520                     525                          530                          535

CTC  ACA  GAA  TTT  GAG  AAT  GAG  CTA  TCC  GAT  TAT  ACA  TAT  ATG  AGA  GTG               576
Leu  Thr  Glu  Phe  Glu  Asn  Glu  Leu  Ser  Asp  Tyr  Thr  Tyr  Met  Arg  Val
                    540                          545                          550

GAT  GCA  CGG  AAA  GAT  GGG  CTC  AAT  GTA  AAA  GTT  CTT  CTT  GGA  GCT  ATC               624
Asp  Ala  Arg  Lys  Asp  Gly  Leu  Asn  Val  Lys  Val  Leu  Leu  Gly  Ala  Ile
               555                          560                          565

AAT  GAG  AAT  ATG  AAG  CTG  AAT  TGT  AAT  GTG  AAG  AGA  GGC  CAA  TCT  ACG               672
Asn  Glu  Asn  Met  Lys  Leu  Asn  Cys  Asn  Val  Lys  Arg  Gly  Gln  Ser  Thr
               570                          575                          580

ATT  AGT  TGG  GCT  CGA  TCT  ATT  CGC  AGA  AAA  ATG  AAT  AGC  CAA  CAG  TTG               720
Ile  Ser  Trp  Ala  Arg  Ser  Ile  Arg  Arg  Lys  Met  Asn  Ser  Gln  Gln  Leu
585                     590                          595

ATT  CTT  ATC  ATT  GAT  AAT  ATT  GAA  GCT  CCT  GAT  TGG  AGA  AGT  GAT  CAA               768
Ile  Leu  Ile  Ile  Asp  Asn  Ile  Glu  Ala  Pro  Asp  Trp  Arg  Ser  Asp  Gln
600                     605                          610                          615

GAA  GCA  TTT  TGC  GAA  CTT  CTT  GAG  AAT  CGG  GAT  TCG  GTG  AAA  TTG  ATT               816
Glu  Ala  Phe  Cys  Glu  Leu  Leu  Glu  Asn  Arg  Asp  Ser  Val  Lys  Leu  Ile
                    620                          625                          630

GCT  ACA  GTT  GAT  CAC  ATT  TAC  TCG  ACG  TTC  ATC  TGG  AAT  TCG  CGT  CAA               864
Ala  Thr  Val  Asp  His  Ile  Tyr  Ser  Thr  Phe  Ile  Trp  Asn  Ser  Arg  Gln
               635                          640                          645

CTA  TCA  TCA  CTC  TCA  TTC  GTT  CAC  ATC  ACA  ATC  AAC  ACC  TTC  GAA  ATT               912
Leu  Ser  Ser  Leu  Ser  Phe  Val  His  Ile  Thr  Ile  Asn  Thr  Phe  Glu  Ile
               650                          655                          660

CCA  CTT  CAA  GAA  TTA  ATG  ACT  GGA  GAT  TCT  CGT  CTT  CTT  GGT  CTT  GAT               960
Pro  Leu  Gln  Glu  Leu  Met  Thr  Gly  Asp  Ser  Arg  Leu  Leu  Gly  Leu  Asp
665                     670                          675

GCT  CGT  TCG  AAT  CAA  TCC  TCT  CAT  ACA  ATG  TCA  TCG  CTT  GAT  GTG  TTC              1008
Ala  Arg  Ser  Asn  Gln  Ser  Ser  His  Thr  Met  Ser  Ser  Leu  Asp  Val  Phe
680                     685                          690                          695

TGG  AAA  TCT  CTT  GCC  GTC  AAT  TCA  CAA  AAA  TTA  TTC  CGT  CTC  TTT  TTC              1056
Trp  Lys  Ser  Leu  Ala  Val  Asn  Ser  Gln  Lys  Leu  Phe  Arg  Leu  Phe  Phe
                    700                          705                          710

CAA  ATG  TAC  TTT  GAC  ACC  AAG  AAG  CCT  GTC  AAA  TTC  TGG  GAT  TTG  TTC              1104
Gln  Met  Tyr  Phe  Asp  Thr  Lys  Lys  Pro  Val  Lys  Phe  Trp  Asp  Leu  Phe
               715                          720                          725

AAT  GCG  GCA  AAA  GAT  GAT  TTC  ATT  GCT  TCA  ACT  GAC  GCT  GCT  CTT  CGA              1152
Asn  Ala  Ala  Lys  Asp  Asp  Phe  Ile  Ala  Ser  Thr  Asp  Ala  Ala  Leu  Arg
               730                          735                          740

ACC  CAA  CTT  GTC  GAA  TTC  AAG  GAT  CAT  CGG  GTT  TTG  AAG  TGG  ACC  CGT              1200
Thr  Gln  Leu  Val  Glu  Phe  Lys  Asp  His  Arg  Val  Leu  Lys  Trp  Thr  Arg
745                     750                          755

GGT  GAT  GAC  GGA  AAC  GAT  CAG  CTG  TCG  GGC  ATT  GTC  GAA  TTA  CGA  TTA              1248
Gly  Asp  Asp  Gly  Asn  Asp  Gln  Leu  Ser  Gly  Ile  Val  Glu  Leu  Arg  Leu
760                     765                          770                          775

GTG  ACC  GAA  TTT  CTC  GAA  TCG  AAG  AAC  ATG  CCG  TTA  GAC  GAA  AAG  AAA              1296
Val  Thr  Glu  Phe  Leu  Glu  Ser  Lys  Asn  Met  Pro  Leu  Asp  Glu  Lys  Lys
                    780                          785                          790

GAC  GAG  TAGCTGCTGC  TACTGCTGGA  GGACCTCAAA  AATGAACACA  CTCTGCCTCC                          1352
Asp  Glu
TTTTGACTCA  ATGTATTTAC  CTTCAATTGT  TTTATTTGTT  GACTCTGCGC  CCCCCGTCCG                        1412

TCCGTCGATG  CTTCTTCATC  CCATTTTTTT  TTACTTCAAT  TGAAACCTCA  ATCTTCACTT                        1472

ACTCTCATCT  GAACGCTCAT  ATTTAAGGCA  ATAATTTTCA  TTTTCAAATA  TATCAATTGA                        1532

AACCTTTATC  TACCGTAATA  CCAATTTTGT  GTACCTTTTC  AAAAATCTCA  TTTCCCCCTC                        1592
```

```
GGTTTTTTCT TCACGATTTC TCAATTATTT TCAGTTTCTC ACTATCAGTT TCACATTCCC        1652

ATATTGAAT GAATCTCATT TTCC                                                1676
```

( 2 ) INFORMATION FOR SEQ ID NO:22:

( i ) SEQUENCE CHARACTERISTICS:
        ( A ) LENGTH: 430 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Met Pro Arg Pro Lys Ile Leu Lys Arg Ala Thr Val Gln Pro Ser Ala
 1               5                  10                 15

Ala Val Pro Val Lys Lys Ser Thr Pro Glu Lys Glu Gly Ser Arg Gln
             20                  25                 30

Lys Lys Thr Asn Gly Lys Glu Asn Ala Ser Arg Asn Leu Gln Ser Asn
         35                  40                  45

Leu Glu Glu Asp Leu Glu Gln Leu Gly Phe Glu Asp Glu Thr Val Ser
 50                  55                  60

Met Ala Gln Ser Ala Ile Glu Asn Tyr Phe Met Gln Gly Lys Ser Ala
 65                  70                  75                 80

Ser Glu Arg Met Asn Asn Ala Lys Ser Arg Arg Gly Arg Arg Ala Gly
                 85                  90                 95

Asn Gly Asn Thr Glu Glu Ile Glu Glu Asp Asp Glu Ile Ser Asn Ala
             100                 105                110

Ile Thr Asp Phe Thr Lys Cys Asp Leu Pro Gly Leu Arg Asn Tyr Ile
             115                 120                125

Thr Lys Lys Asp Asn Thr Glu Phe Glu Lys Arg Leu Glu His Leu Ala
130                  135                 140

Asp Asn Asp Phe Gly Lys Trp Lys Leu Tyr Leu Ala Ala Gly Phe Asn
145                  150                 155                160

Ile Leu Leu His Gly Val Gly Ser Lys Arg Asp Val Leu Thr Glu Phe
                 165                 170                175

Glu Asn Glu Leu Ser Asp Tyr Thr Tyr Met Arg Val Asp Ala Arg Lys
             180                 185                 190

Asp Gly Leu Asn Val Lys Val Leu Leu Gly Ala Ile Asn Glu Asn Met
             195                 200                 205

Lys Leu Asn Cys Asn Val Lys Arg Gly Gln Ser Thr Ile Ser Trp Ala
210                  215                 220

Arg Ser Ile Arg Arg Lys Met Asn Ser Gln Gln Leu Ile Leu Ile Ile
225                  230                 235                240

Asp Asn Ile Glu Ala Pro Asp Trp Arg Ser Asp Gln Glu Ala Phe Cys
             245                 250                 255

Glu Leu Leu Glu Asn Arg Asp Ser Val Lys Leu Ile Ala Thr Val Asp
             260                 265                 270

His Ile Tyr Ser Thr Phe Ile Trp Asn Ser Arg Gln Leu Ser Ser Leu
             275                 280                 285

Ser Phe Val His Ile Thr Ile Asn Thr Phe Glu Ile Pro Leu Gln Glu
    290                 295                 300

Leu Met Thr Gly Asp Ser Arg Leu Leu Gly Leu Asp Ala Arg Ser Asn
305                  310                 315                320

Gln Ser Ser His Thr Met Ser Ser Leu Asp Val Phe Trp Lys Ser Leu
                 325                 330                 335
```

```
Ala  Val  Asn  Ser  Gln  Lys  Leu  Phe  Arg  Leu  Phe  Phe  Gln  Met  Tyr  Phe
               340                      345                      350

Asp  Thr  Lys  Lys  Pro  Val  Lys  Phe  Trp  Asp  Leu  Phe  Asn  Ala  Ala  Lys
               355                      360                      365

Asp  Asp  Phe  Ile  Ala  Ser  Thr  Asp  Ala  Ala  Leu  Arg  Thr  Gln  Leu  Val
          370                      375                      380

Glu  Phe  Lys  Asp  His  Arg  Val  Leu  Lys  Trp  Thr  Arg  Gly  Asp  Asp  Gly
385                           390                      395                      400

Asn  Asp  Gln  Leu  Ser  Gly  Ile  Val  Glu  Leu  Arg  Leu  Val  Thr  Glu  Phe
                    405                      410                      415

Leu  Glu  Ser  Lys  Asn  Met  Pro  Leu  Asp  Glu  Lys  Lys  Asp  Glu
               420                      425                      430
```

( 2 ) INFORMATION FOR SEQ ID NO:23:

( i ) SEQUENCE CHARACTERISTICS:
        ( A ) LENGTH: 2729 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 187..1917

( x i ) SEQUENCE DESCRIPTION: SEQ ID NO:23:

```
GGCGCGAATT  ACTGGAAATT  GGCTTTTCCC  GTTGGGGCCG  AAGGTACCTT  CCCTGCGGCG         60

GCGACTCAGC  GGGGTGTCGT  TCGGCCGGCG  TGACGCAGCC  GGATCGGCGC  CAGACGGAAA        120

CCTAGCGGTG  ACTGTATCTG  AATTTGCAG  CTGCAGAATG  TGTAGTACCT  TAAAAGGTTG        180

GCAACA ATG  AGT  AAA  CCA  GAA  TTA  AAG  GAA  GAC  AAG  ATG  CTG  GAG  GTT        228
       Met  Ser  Lys  Pro  Glu  Leu  Lys  Glu  Asp  Lys  Met  Leu  Glu  Val
                             435                      440

CAC  TTT  GTG  GGA  GAT  GAT  GAT  GTT  CTT  AAT  CAC  ATT  CTA  GAT  AGA  GAA        276
His  Phe  Val  Gly  Asp  Asp  Asp  Val  Leu  Asn  His  Ile  Leu  Asp  Arg  Glu
445                           450                      455                      460

GGA  GGA  GCT  AAA  TTG  AAG  AAG  GAG  CGA  GCG  CAC  GTT  TTG  GTC  AAC  CCC        324
Gly  Gly  Ala  Lys  Leu  Lys  Lys  Glu  Arg  Ala  His  Val  Leu  Val  Asn  Pro
                    465                      470                      475

AAA  AAA  ATA  ATA  AAG  AAG  CCA  GAA  TAT  GAT  TTG  GAG  GAA  GAT  GAC  CAG        372
Lys  Lys  Ile  Ile  Lys  Lys  Pro  Glu  Tyr  Asp  Leu  Glu  Glu  Asp  Asp  Gln
                    480                      485                      490

GAG  GTC  TTA  AAA  GAT  CAG  AAC  TAT  GTG  GAA  ATT  ATG  GGA  AGA  GAT  GTT        420
Glu  Val  Leu  Lys  Asp  Gln  Asn  Tyr  Val  Glu  Ile  Met  Gly  Arg  Asp  Val
               495                      500                      505

CAA  GAA  TCA  TTG  AAA  AAT  GGC  TCT  GCT  ACA  GGT  GGT  GGA  AAT  AAA  GTT        468
Gln  Glu  Ser  Leu  Lys  Asn  Gly  Ser  Ala  Thr  Gly  Gly  Gly  Asn  Lys  Val
          510                      515                      520

TAT  TCT  TTT  CAG  AAT  AGA  AAA  CAC  TCT  GAA  AAG  ATG  GCT  AAA  TTA  GCT        516
Tyr  Ser  Phe  Gln  Asn  Arg  Lys  His  Ser  Glu  Lys  Met  Ala  Lys  Leu  Ala
525                           530                      535                      540

TCA  GAA  CTA  GCA  AAA  ACA  CCA  CAA  AAA  AGT  GTT  TCA  TTC  AGT  TTG  AAG        564
Ser  Glu  Leu  Ala  Lys  Thr  Pro  Gln  Lys  Ser  Val  Ser  Phe  Ser  Leu  Lys
                    545                      550                      555

AAT  GAT  CCT  GAG  ATT  ACG  ATA  AAC  GTT  CCT  CAA  AGT  AGC  AAG  GGC  CAT        612
Asn  Asp  Pro  Glu  Ile  Thr  Ile  Asn  Val  Pro  Gln  Ser  Ser  Lys  Gly  His
               560                      565                      570

TCT  GCT  TCA  GAC  AAG  GTT  CAA  CCG  AAG  AAC  AAT  GAC  AAA  AGT  GAA  TTT        660
Ser  Ala  Ser  Asp  Lys  Val  Gln  Pro  Lys  Asn  Asn  Asp  Lys  Ser  Glu  Phe
          575                      580                      585
```

| | | | | | | | | | | | | | | | | |
|---|---|---|---|---|---|---|---|---|---|---|---|---|---|---|---|---|
| CTG | TCA | ACA | GCA | CCT | CGT | AGT | CTA | AGA | AAA | AGA | TTA | ATA | GTT | CCA | AGG | 708 |
| Leu | Ser | Thr | Ala | Pro | Arg | Ser | Leu | Arg | Lys | Arg | Leu | Ile | Val | Pro | Arg | |
| | 590 | | | | 595 | | | | | 600 | | | | | | |
| TCT | CAT | TCT | GAC | AGT | GAA | AGC | GAA | TAT | TCT | GCT | TCC | AAC | TCA | GAG | GAT | 756 |
| Ser | His | Ser | Asp | Ser | Glu | Ser | Glu | Tyr | Ser | Ala | Ser | Asn | Ser | Glu | Asp | |
| 605 | | | | | 610 | | | | 615 | | | | | | 620 | |
| GAT | GAA | GGG | GTT | GCA | CAG | GAA | CAT | GAA | GAG | GAC | ACT | AAT | GCA | GTC | ATA | 804 |
| Asp | Glu | Gly | Val | Ala | Gln | Glu | His | Glu | Glu | Asp | Thr | Asn | Ala | Val | Ile | |
| | | | | 625 | | | | | 630 | | | | | 635 | | |
| TTC | AGC | CAA | AAG | ATT | CAA | GCT | CAG | AAT | AGA | GTA | GTT | TCA | GCT | CCT | GTT | 852 |
| Phe | Ser | Gln | Lys | Ile | Gln | Ala | Gln | Asn | Arg | Val | Val | Ser | Ala | Pro | Val | |
| | | | 640 | | | | | 645 | | | | | 650 | | | |
| GGC | AAA | GAA | ACA | CCT | TCT | AAG | AGA | ATG | AAA | AGA | GAT | AAA | ACA | AGT | GAC | 900 |
| Gly | Lys | Glu | Thr | Pro | Ser | Lys | Arg | Met | Lys | Arg | Asp | Lys | Thr | Ser | Asp | |
| | | 655 | | | | | 660 | | | | | 665 | | | | |
| TTA | GTA | GAA | GAA | TAT | TTT | GAA | GCT | CAC | AGC | AGT | TCA | AAA | GTT | TTA | ACC | 948 |
| Leu | Val | Glu | Glu | Tyr | Phe | Glu | Ala | His | Ser | Ser | Ser | Lys | Val | Leu | Thr | |
| | 670 | | | | | 675 | | | | | 680 | | | | | |
| TCT | GAT | AGA | ACA | CTG | CAG | AAG | CTA | AAG | AGA | GCT | AAA | CTG | GAT | CAG | CAA | 996 |
| Ser | Asp | Arg | Thr | Leu | Gln | Lys | Leu | Lys | Arg | Ala | Lys | Leu | Asp | Gln | Gln | |
| 685 | | | | | 690 | | | | | 695 | | | | | 700 | |
| ACT | TTG | CGT | AAC | TTA | TTG | AGC | AAG | GTT | TCC | CCT | TCC | TTT | TCT | GCC | GAA | 1044 |
| Thr | Leu | Arg | Asn | Leu | Leu | Ser | Lys | Val | Ser | Pro | Ser | Phe | Ser | Ala | Glu | |
| | | | | | 705 | | | | | 710 | | | | | 715 | |
| CTT | AAA | CAA | CTA | AAT | CAA | CAG | TAT | GAA | AAA | TTA | TTT | CAT | AAA | TGG | ATG | 1092 |
| Leu | Lys | Gln | Leu | Asn | Gln | Gln | Tyr | Glu | Lys | Leu | Phe | His | Lys | Trp | Met | |
| | | | | 720 | | | | | 725 | | | | | 730 | | |
| CTG | CAA | TTA | CAC | CTT | GGG | TTC | AAC | ATT | GTG | CTT | TAT | GGT | TTG | GGT | TCT | 1140 |
| Leu | Gln | Leu | His | Leu | Gly | Phe | Asn | Ile | Val | Leu | Tyr | Gly | Leu | Gly | Ser | |
| | | | 735 | | | | | 740 | | | | | 745 | | | |
| AAG | AGA | GAT | TTA | CTA | GAA | AGG | TTT | CGA | ACC | ACT | ATG | CTG | CAA | GAT | TCC | 1188 |
| Lys | Arg | Asp | Leu | Leu | Glu | Arg | Phe | Arg | Thr | Thr | Met | Leu | Gln | Asp | Ser | |
| | 750 | | | | | 755 | | | | | 760 | | | | | |
| ATT | CAC | GTT | GTC | ATC | AAT | GGC | TTC | TTT | CCT | GGA | ATC | AGT | GTG | AAA | TCA | 1236 |
| Ile | His | Val | Val | Ile | Asn | Gly | Phe | Phe | Pro | Gly | Ile | Ser | Val | Lys | Ser | |
| 765 | | | | | 770 | | | | | 775 | | | | | 780 | |
| GTC | CTG | AAT | TCT | ATA | ACA | GAA | GAA | GTC | CTC | GAT | CAT | ATG | GGT | ACT | TTC | 1284 |
| Val | Leu | Asn | Ser | Ile | Thr | Glu | Glu | Val | Leu | Asp | His | Met | Gly | Thr | Phe | |
| | | | | 785 | | | | | 790 | | | | | 795 | | |
| CGC | AGT | ATA | CTG | GAT | CAG | CTA | GAC | TGG | ATA | GTA | AAC | AAA | TTT | AAA | GAA | 1332 |
| Arg | Ser | Ile | Leu | Asp | Gln | Leu | Asp | Trp | Ile | Val | Asn | Lys | Phe | Lys | Glu | |
| | | | 800 | | | | | 805 | | | | | 810 | | | |
| GAT | TCT | TCT | TTA | GAA | CTC | TTC | CTT | CTC | ATC | CAC | AAT | TTG | GAT | AGC | CAG | 1380 |
| Asp | Ser | Ser | Leu | Glu | Leu | Phe | Leu | Leu | Ile | His | Asn | Leu | Asp | Ser | Gln | |
| | | 815 | | | | | 820 | | | | | 825 | | | | |
| ATG | TTG | AGA | GGA | GAG | AAG | AGC | CAG | CAA | ATC | ATT | GGT | CAG | TTG | TCA | TCT | 1428 |
| Met | Leu | Arg | Gly | Glu | Lys | Ser | Gln | Gln | Ile | Ile | Gly | Gln | Leu | Ser | Ser | |
| | 830 | | | | | 835 | | | | | 840 | | | | | |
| TTG | CAT | AAC | ATT | TAC | CTT | ATA | GCA | TCC | ATT | GAC | CAC | CTC | AAT | GCT | CCT | 1476 |
| Leu | His | Asn | Ile | Tyr | Leu | Ile | Ala | Ser | Ile | Asp | His | Leu | Asn | Ala | Pro | |
| 845 | | | | | 850 | | | | | 855 | | | | | 860 | |
| CTC | ATG | TGG | GAT | CAT | GCA | AAG | CAG | AGT | CTT | TTT | AAC | TGG | CTC | TGG | TAT | 1524 |
| Leu | Met | Trp | Asp | His | Ala | Lys | Gln | Ser | Leu | Phe | Asn | Trp | Leu | Trp | Tyr | |
| | | | | 865 | | | | | 870 | | | | | 875 | | |
| GAA | ACT | ACT | ACA | TAC | AGT | CCT | TAT | ACT | GAA | GAA | ACC | TCC | TAT | GAG | AAC | 1572 |
| Glu | Thr | Thr | Thr | Tyr | Ser | Pro | Tyr | Thr | Glu | Glu | Thr | Ser | Tyr | Glu | Asn | |
| | | | 880 | | | | | 885 | | | | | 890 | | | |
| TCT | CTT | CTG | GTA | AAG | CAG | TCT | GGA | TCC | CTG | CCA | CTT | AGC | TCC | CTT | ACT | 1620 |
| Ser | Leu | Leu | Val | Lys | Gln | Ser | Gly | Ser | Leu | Pro | Leu | Ser | Ser | Leu | Thr | |
| | | 895 | | | | | 900 | | | | | 905 | | | | |

| | | | | | | | | | | | | | | | | |
|---|---|---|---|---|---|---|---|---|---|---|---|---|---|---|---|---|
| CAT | GTC | TTA | CGA | AGC | CTT | ACC | CCT | AAT | GCA | AGG | GGA | ATT | TTC | AGG | CTA | 1668 |
| His | Val | Leu | Arg | Ser | Leu | Thr | Pro | Asn | Ala | Arg | Gly | Ile | Phe | Arg | Leu | |
| | 910 | | | | | 915 | | | | | 920 | | | | | |
| CTA | ATA | AAA | TAC | CAG | CTG | GAC | AAC | CAG | GAT | AAC | CCT | TCT | TAC | ATT | GGC | 1716 |
| Leu | Ile | Lys | Tyr | Gln | Leu | Asp | Asn | Gln | Asp | Asn | Pro | Ser | Tyr | Ile | Gly | |
| 925 | | | | | 930 | | | | | 935 | | | | | 940 | |
| CTT | TCT | TTT | CAA | GAT | TTT | TAC | CAG | CAG | TGT | CGG | GAG | GCA | TTC | CTC | GTC | 1764 |
| Leu | Ser | Phe | Gln | Asp | Phe | Tyr | Gln | Gln | Cys | Arg | Glu | Ala | Phe | Leu | Val | |
| | | | | 945 | | | | | 950 | | | | | 955 | | |
| AAT | AGT | GAT | CTG | ACA | CTC | CGG | GCC | CAG | TTA | ACT | GAA | TTT | AGG | GAC | CAC | 1812 |
| Asn | Ser | Asp | Leu | Thr | Leu | Arg | Ala | Gln | Leu | Thr | Glu | Phe | Arg | Asp | His | |
| | | | 960 | | | | | 965 | | | | | 970 | | | |
| AAG | CTT | ATA | AGA | ACA | AAG | AAG | GGA | ACT | GAT | GGA | GTA | GAG | TAT | TTA | TTA | 1860 |
| Lys | Leu | Ile | Arg | Thr | Lys | Lys | Gly | Thr | Asp | Gly | Val | Glu | Tyr | Leu | Leu | |
| | | 975 | | | | | 980 | | | | | 985 | | | | |
| ATT | CCT | GTT | GAT | AAT | GGA | ACA | TTG | ACT | GAT | TTC | TTG | GAA | AAG | GAA | GAA | 1908 |
| Ile | Pro | Val | Asp | Asn | Gly | Thr | Leu | Thr | Asp | Phe | Leu | Glu | Lys | Glu | Glu | |
| | 990 | | | | | 995 | | | | | 1000 | | | | | |
| GAG | GAG | GCT | TGAAGCTTTC | CTTTATTCTT | GAATCTCCCA | TGGAAGGGTT | | | | | | | | | | 1957 |
| Glu | Glu | Ala | | | | | | | | | | | | | | |
| 1005 | | | | | | | | | | | | | | | | |

| | | | | |
|---|---|---|---|---|
| GTACCCCAGC | TGCCACTCCT | CTAGTTGAAA | GTGTTGTGTT | TACATCTGAC | ATTAAATTAT | 2017 |
| TTTTCCAGCA | TACAAGATTT | AAATTTGGGA | AGGGGGGGAT | GTCCTCAATT | AGAACTTTTT | 2077 |
| GATCAGCCTG | GCTGGTACCG | TCTAGTACTA | TGCAGCGGTC | CTCAAGTTGG | AGAAAATGTG | 2137 |
| CCTTTCATTC | ATTACCTCTC | TGGAGACTTC | TTGCTGGAAT | GAACAGTGTG | CTCAGGGACT | 2197 |
| ATTGGAACT | GGATGTTTTT | GAATTATTTT | ATACTTAGAG | ATATTCTGAA | TTTTTTGAGG | 2257 |
| GCCTTTTAAC | ACTCCCCGAG | CTGATTGTTT | GCAAGTGTGT | TTGTTCCAGA | GTGTGGAAGT | 2317 |
| ATAAAGACAT | GGGCATCACG | TAAATTGGTT | TTGTTTGCTA | TTCTGTGTGT | CAGAACCAAC | 2377 |
| GAGTGTAATG | GAGAGGGCAG | GTCATCTCTT | ATTGTTTCTA | AACAACTTA | AAAGGTGTAG | 2437 |
| ATTGGGAAGA | GGTGAGTGAT | CCAGCTTTCT | CCTTTGGAT | TGAGGCTATG | TACTTGGTGG | 2497 |
| GGGCAGGGGA | GGGAATATAT | TATAATACTA | TTCAGTTGGG | ATAATGGGAA | AAACAGAGTA | 2557 |
| TATAGGGTAT | CTACCCAGCC | TAGAAAGCAC | AGGAACAATA | CGTCATATAT | TTGGAACAGT | 2617 |
| TATTGTCTGT | GCCATGACCT | TCATGATACC | AGTGAGAAGC | CAGGCTAGAG | AAATAAAATC | 2677 |
| CTGAATTACA | TTTTAGTAAT | TGTTTTCAAG | ACAACAAAAA | ATAAAACATT | TC | 2729 |

( 2 ) INFORMATION FOR SEQ ID NO:24:

( i ) SEQUENCE CHARACTERISTICS:
        ( A ) LENGTH: 577 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

| | | | | | | | | | | | | | | |
|---|---|---|---|---|---|---|---|---|---|---|---|---|---|---|
| Met | Ser | Lys | Pro | Glu | Leu | Lys | Glu | Asp | Lys | Met | Leu | Glu | Val | His | Phe |
| 1 | | | | 5 | | | | | 10 | | | | | 15 | |
| Val | Gly | Asp | Asp | Asp | Val | Leu | Asn | His | Ile | Leu | Asp | Arg | Glu | Gly | Gly |
| | | | 20 | | | | | 25 | | | | | 30 | | |
| Ala | Lys | Leu | Lys | Lys | Glu | Arg | Ala | His | Val | Leu | Val | Asn | Pro | Lys | Lys |
| | | | 35 | | | | 40 | | | | | 45 | | | |
| Ile | Ile | Lys | Lys | Pro | Glu | Tyr | Asp | Leu | Glu | Glu | Asp | Asp | Gln | Glu | Val |
| | | 50 | | | | | 55 | | | | | 60 | | | |
| Leu | Lys | Asp | Gln | Asn | Tyr | Val | Glu | Ile | Met | Gly | Arg | Asp | Val | Gln | Glu |

|     |     |     | 65  |     |     |     | 70  |     |     |     | 75  |     |     |     | 80  |
| --- | --- | --- | --- | --- | --- | --- | --- | --- | --- | --- | --- | --- | --- | --- | --- |

Ser Leu Lys Asn Gly Ser Ala Thr Gly Gly Asn Lys Val Tyr Ser
              85                  90                  95

Phe Gln Asn Arg Lys His Ser Glu Lys Met Ala Lys Leu Ala Ser Glu
            100                 105                 110

Leu Ala Lys Thr Pro Gln Lys Ser Val Ser Phe Ser Leu Lys Asn Asp
            115                 120                 125

Pro Glu Ile Thr Ile Asn Val Pro Gln Ser Ser Lys Gly His Ser Ala
    130                 135                 140

Ser Asp Lys Val Gln Pro Lys Asn Asn Asp Lys Ser Glu Phe Leu Ser
145                 150                 155                 160

Thr Ala Pro Arg Ser Leu Arg Lys Arg Leu Ile Val Pro Arg Ser His
                165                 170                 175

Ser Asp Ser Glu Ser Glu Tyr Ser Ala Ser Asn Ser Glu Asp Asp Glu
                180                 185                 190

Gly Val Ala Gln Glu His Glu Glu Asp Thr Asn Ala Val Ile Phe Ser
            195                 200                 205

Gln Lys Ile Gln Ala Gln Asn Arg Val Val Ser Ala Pro Val Gly Lys
    210                 215                 220

Glu Thr Pro Ser Lys Arg Met Lys Arg Asp Lys Thr Ser Asp Leu Val
225                 230                 235                 240

Glu Glu Tyr Phe Glu Ala His Ser Ser Ser Lys Val Leu Thr Ser Asp
                245                 250                 255

Arg Thr Leu Gln Lys Leu Lys Arg Ala Lys Leu Asp Gln Gln Thr Leu
            260                 265                 270

Arg Asn Leu Leu Ser Lys Val Ser Pro Ser Phe Ser Ala Glu Leu Lys
            275                 280                 285

Gln Leu Asn Gln Gln Tyr Glu Lys Leu Phe His Lys Trp Met Leu Gln
    290                 295                 300

Leu His Leu Gly Phe Asn Ile Val Leu Tyr Gly Leu Gly Ser Lys Arg
305                 310                 315                 320

Asp Leu Leu Glu Arg Phe Arg Thr Thr Met Leu Gln Asp Ser Ile His
                325                 330                 335

Val Val Ile Asn Gly Phe Phe Pro Gly Ile Ser Val Lys Ser Val Leu
            340                 345                 350

Asn Ser Ile Thr Glu Glu Val Leu Asp His Met Gly Thr Phe Arg Ser
        355                 360                 365

Ile Leu Asp Gln Leu Asp Trp Ile Val Asn Lys Phe Lys Glu Asp Ser
    370                 375                 380

Ser Leu Glu Leu Phe Leu Leu Ile His Asn Leu Asp Ser Gln Met Leu
385                 390                 395                 400

Arg Gly Glu Lys Ser Gln Gln Ile Ile Gly Gln Leu Ser Ser Leu His
                405                 410                 415

Asn Ile Tyr Leu Ile Ala Ser Ile Asp His Leu Asn Ala Pro Leu Met
            420                 425                 430

Trp Asp His Ala Lys Gln Ser Leu Phe Asn Trp Leu Trp Tyr Glu Thr
        435                 440                 445

Thr Thr Tyr Ser Pro Tyr Thr Glu Glu Thr Ser Tyr Glu Asn Ser Leu
    450                 455                 460

Leu Val Lys Gln Ser Gly Ser Leu Pro Leu Ser Ser Leu Thr His Val
465                 470                 475                 480

Leu Arg Ser Leu Thr Pro Asn Ala Arg Gly Ile Phe Arg Leu Leu Ile
                485                 490                 495

| | | | | | | | | | | | | | | | |
|---|---|---|---|---|---|---|---|---|---|---|---|---|---|---|---|
| Lys | Tyr | Gln | Leu<br>500 | Asp | Asn | Gln | Asp | Asn<br>505 | Pro | Ser | Tyr | Ile | Gly<br>510 | Leu | Ser |
| Phe | Gln | Asp<br>515 | Phe | Tyr | Gln | Gln | Cys<br>520 | Arg | Glu | Ala | Phe | Leu<br>525 | Val | Asn | Ser |
| Asp | Leu<br>530 | Thr | Leu | Arg | Ala | Gln<br>535 | Leu | Thr | Glu | Phe | Arg<br>540 | Asp | His | Lys | Leu |
| Ile<br>545 | Arg | Thr | Lys | Lys | Gly<br>550 | Thr | Asp | Gly | Val | Glu<br>555 | Tyr | Leu | Leu | Ile | Pro<br>560 |
| Val | Asp | Asn | Gly | Thr<br>565 | Leu | Thr | Asp | Phe | Leu<br>570 | Glu | Lys | Glu | Glu | Glu<br>575 | Glu |
| Ala | | | | | | | | | | | | | | | |

ORIGIN OF REPLICATION COMPLEX GENES AND METHODS OF USING THE SAME

The research carried out in the subject application was supported in part by grants from the National Institutes of Health. The government may have rights in any patent issuing on this application.

RELATED APPLICATION

This application is a division of Ser. No. 08/168,479 filed Dec. 16, 1993 now abandoned, directed to the invention of the non-elected group III.

INTRODUCTION

1. Field of the Invention

The field of this invention is genes involved in replication and their use in drug screening.

2. Background

The identification of new pharmaceuticals is a multibillion dollar industry. The goal of therapeutic intervention is frequently to control cell growth, whether the cell be a host cell (e.g a cancer cell) or a foreign cell (e.g. an infectious pathogen). Cellular components involved in the initiation of DNA synthesis have provided proven targets for therapeutic intervention to control cell growth. Such targets find immediate industrial application in the screening of chemical libraries for inhibitors of cellular replication. Study of the control and regulation of DNA synthesis in the yeast *Saccharomyces cerevisiae* has identified a mutiprotein complex, the origin recognition complex (ORC), which is essential for DNA replication (Bell and Stillman, 1992). Disclosed herein are ORC genes and proteins from a number of representative animal species.

Relevant Literature

A multi-protein complex that recognizes cellular origins of DNA replication was reported in Bell and Stillman (1992) Nature 357, 128–134. ORC genes have been reported in Micklem et at. (1993) Nature 366, 87–89, Foss et at. (1993) Science 262, 1838–1844, Li and Herskowicz (1993) Science 262, 1870–1874, Bell et at. (1993), Science 262, 1844–1870 and Liang, Weinreich and Stillman (1995) Cell 81 (Jun. 1, 1995) issue.

SUMMARY OF THE INVENTION

The invention provides methods and compositions relating to Origin of Replication Complex (ORC) genes. The compositions include nucleic acids which encode ORC proteins and hybridization reagents, probes and primers capable of hybridizing with ORC genes. The invention includes methods for screening chemical libraries for lead compounds for pharmacological agents useful in the diagnosis or treatment of disease associated undesirable cell growth. In one embodiment, the methods involve (1) forming a mixture comprising a recombinant ORC protein, a natural intracellular ORC protein binding target, and a candidate pharmacological agent; (2) incubating the mixture under conditions whereby, but for the presence of said candidate pharmacological agent, said ORC protein selectively binds said binding target; and (3) detecting the presence or absence of specific binding of said ORC protein to said binding target, wherein the absence of said selective binding indicates that said candidate pharmacological agent is a lead compound for a pharmacological agent capable of disrupting ORC protein function and inhibiting cell growth.

DETAILED DESCRIPTION OF THE INVENTION

The invention provides methods and compositions relating to the eukaryotic origin of replication complex. The complex comprises six proteins which are highly conserved across eukaryotes. The nucleotide sequences of cDNAs of natural transcripts encoding *S. Cerevisiae* ORC 1–6 are shown as SEQUENCE ID NO:1, 3, 5, 7, 9 and 11, respectively; and the full corresponding conceptual translates of these cDNAs are shown as SEQUENCE ID NOS:2, 4, 6, 8, 10 and 12. The nucleotide sequences of cDNAs of natural transcripts encoding *K. lactis, S. pombe* and human ORC1 are shown as SEQUENCE ID NOS:13, 15 and 17, respectively; and the full corresponding conceptual translates of these cDNAs are shown as SEQUENCE ID NOS: 14, 16 and 18. The nucleotide sequences of cDNAs of natural transcripts encoding *A. thaliana, C. elegans* and human ORC2 are shown as SEQUENCE ID NOS: 19, 21 and 23, respectively; and the full corresponding conceptual translates of these cDNAs are shown as SEQUENCE ID NOS:20, 22 and 24.

The subject ORC proteins of the invention may be incomplete translates of the cDNA sequences or deletion mutants of the corresponding conceptual translates, which translates or deletion mutants have the ORC binding activity and specificity described herein. The subject ORC proteins are isolated, partially pure or pure and are typically recombinantly produced. An "isolated" protein for example, is unaccompanied by at least some of the material with which it is associated in its natural state and constitutes at least about 0.5%, preferably at least about 2%, and more preferably at least about 5% by weight of the total protein in a given sample; a partially pure protein constitutes at least about 10%, preferably at least about 30%, and more preferably at least about 60% by weight of the total protein in a given sample; and a pure protein constitutes at least about 70%, preferably at least about 90%, and more preferably at least about 95% by weight of the total protein in a given sample. A wide variety of molecular and biochemical methods are available for generating and expressing the subject compositions, see e.g. Molecular Cloning, A Laboratory Manual (Sambrook, et al. Cold Spring Harbor Laboratory), Current Protocols in Molecular Biology (Eds. Aufubel, et al., Greene Publ. Assoc., Wiley-Interscience, New York) or that are otherwise known in the art.

The invention provides ORC-specific binding agents including natural intracellular binding targets such as ori sites, other ORC proteins, etc. and methods of identifying and making such agents, and their use in diagnosis, therapy and pharmaceutical development. For example, ORC-specific agents, especially agents which modulate ORC function, are useful in a variety of diagnostic and therapeutic applications, especially where disease is associated with excessive cell growth. Novel ORC-specific binding agents include ORC-specific antibodies and other natural intracellular binding agents identified with assays such as one- and two-hybrid screens, non-natural intracellular binding agents identified in screens of chemical libraries, etc.

Generally, ORC-specificity of the binding agent is shown by binding equilibrium constants. Such agents are capable of selectively binding an ORC, i.e. with an equilibrium constant at least about $10^7$ $M^{-1}$, preferably at least about $10^8$ $M^{-1}$, more preferably at least about $10^9$ $M^{-1}$. A wide variety of cell-based and cell-free assays may be used to demonstrate ORC-specific binding; preferred are rapid in vitro, cell-free assays such as mediating or inhibiting ORC-protein (e.g. ORCORC) binding, gel shift assays, immunoassays, etc.

The invention also provides nucleic acids encoding the subject proteins, which nucleic acids may be part of ORC-expression vectors and may be incorporated into recombinant cells for expression and screening, transgenic animals for functional studies (e.g. the efficacy of candidate drugs for disease associated with expression of a ORC), etc and ORC-specific hybridization probes comprising an ORC-specific sequence, including replication/amplification primers. The hybridization probes contain a sequence common or complementary to the corresponding ORC gene sufficient to make the probe capable of specifically hybridizing to the corresponding ORC. Hybridization probes having in excess of 50 continuous bases of ORC sequence are generally capable of hybridizing to the corresponding ORC cDNA under stringency conditions characterized by a hybridization buffer comprising 0.9M saline/0.09M sodium citrate (SSC) buffer at a temperature of 37° C. and remaining bound when subject to washing with the SSC buffer at 37° C.; and preferably in a hybridization buffer comprising 20% formamide in 0.9M saline/0.09M sodium citrate (SSC) buffer at a temperature of 42° C. and remaining bound when subject to washing at 42° C. with 0.2× SSC buffer at 42° C.

The subject nucleic acids are isolated, meaning they comprise a sequence joined to a nucleotide other than that which it is joined to on a natural chromosome and usually constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction. The subject nucleic acids find a wide variety of applications including use as translatable transcripts, hybridization probes, PCR primers, therapeutic nucleic acids, etc.; use in detecting the presence of ORC genes and gene transcripts, in detecting or amplifying nucleic acids encoding additional ORC homologs and structural analogs, and in gene therapy applications, e.g. antisense oligonucleotides capable of inhibiting the intracellular expression of a targeted ORC transcript.

The invention provides efficient methods of identifying pharmacological agents or lead compounds for agents active at the level of a ORC modulatable cellular function, particularly DNA replication. Generally, these screening methods involve assaying for compounds which interfere with an ORC binding activity. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target therapeutic indications are limited only in that the target cellular function be subject to modulation, usually inhibition, by disruption of the formation of a complex comprising ORC and one or more natural ORC intracellular binding targets. Target indications may include infection, cell growth and regulatory disfunction, such as neoplasia, inflammation, hypersensitivity, etc.

A wide variety of assays for binding agents are provided including labeled in vitro kinase assays, protein-protein binding assays, immunoassays, cell based assays, etc. The ORC compositions used the methods are usually added in an isolated, partially pure or pure form and are typically recombinantly produced. The ORC may be part of a fusion product with another peptide or polypeptide, e.g. a polypeptide that is capable of providing or enhancing protein-protein binding, stability under assay conditions (e.g. a tag for detection or anchoring), etc. The assay mixtures comprise a natural intracellular ORC binding target. While native binding targets may be used, it is frequently preferred to use portions (e.g. peptides, nucleic acid fragments) thereof so long as the portion provides binding affinity and avidity to the subject ORC conveniently measurable in the assay. The assay mixture also comprises a candidate pharmacological agent. Generally a plurality of assay mixtures are run in parallel with different agent concentrations to obtain a differential response to the various concentrations. Typically, one of these concentrations serves as a negative control, i.e. at zero concentration or below the limits of assay detection. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, etc. which may be used to facilitate optimal binding and/or reduce nonspecific or background interactions, etc. Also, reagents that otherwise improve the efficiency of the assay, such as protease inhibitors, nuclease inhibitors, antimicrobial agents, etc. may be used.

Frequently, the assay mixtures comprise at least a portion a nucleic acid comprising a sequence which shares sufficient sequence similarity with a gene or gene regulatory region to which the targeted ORC protein naturally binds (e.g. an ori sequence) to provide sequence-specific binding. Such a nucleic acid may further comprise one or more sequences which facilitate the binding of one or more additional ORC proteins which cooperatively bind the nucleic acid. Where used, the nucleic acid portion bound by the ORC may be continuous or segmented and is usually linear and double-stranded DNA, though circular plasmids or other nucleic acids or structural analogs may be substituted so long as ORC sequence-specific binding is retained. In some applications, supercoiled DNA provides optimal sequence-specific binding and is preferred. The nucleic acid may be of any length amenable to the assay conditions and requirements.

The resultant mixture is incubated under conditions whereby, but for the presence of the candidate pharmacological agent, the ORC specifically binds the cellular binding target, portion or analog. The mixture components can be added in any order that provides for the requisite bindings. Incubations may be performed at any temperature which facilitates optimal binding, typically between 4 and 40° C., more commonly between 15° and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the presence or absence of specific binding between the ORC fragment and one or more binding targets is detected by any convenient way. For cell-free binding type assays, a separation step is often used to separate bound from unbound components. Separation may be effected by precipitation (e.g. immunoprecipitation), immobilization (e.g. on a solid substrate such as a microtiter plate), etc., followed by washing.

Detection may be effected in any convenient way. For cell-free binding assays, one of the components usually comprises or is coupled to a label. A wide variety of labels may be employed—essentially any label that provides for detection of bound protein. The label may provide for direct detection as radioactivity, luminescence, optical or electron density, etc. or indirect detection such as an epitope tag, an enzyme, etc. The label may be appended to the protein e.g. a phosphate group comprising a radioactive isotope of phosphorous, or incorporated into the protein structure, e.g. a methionine residue comprising a radioactive isotope of sulfur. A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters.

The following experiments and examples are offered by way of illustration and not by way of limitation.

EXPERIMENTAL

1. *S. Cerevisiae* Orc protein purification and gene cloning

To obtain sufficient protein for peptide sequencing, a revised purification procedure for ORC was devised, based on the procedure reported previously (Bell and Stillman, 1992). Whole cell extract was prepared from 400 g of frozen BJ926 cells (frozen immediately after harvesting a 300 liter logarithmically growing culture, total of 1.6 kg per 300 liters). All buffers contained 0.5 mM PMSF, 1 mM benzamidine, 2 mM pepstatin A, 0.1 mg/ml bacitracin and 2mM DTT. 400 mls of 2× buffer H/0.1$^{-NP-40}$ (100 mM Hepes-KOH, pH 7.5, 0.2M KCl, 2 mM EDTA, 2 mM EGTA, 10 mM Mg Acetate, and 20% glycerol) was added to the cells and after thawing the cells were broken using a bead beater (Biospec Products) until greater than 90% cell breakage was achieved (twenty 30 second pulses separated by 90 second pauses). After breakage is complete, the volume of the broken cells was measured and one twelfth volume of a saturated (at 4° C.) solution of ammonium sulfate was added and stirred for 30 minutes. This solution was then spun at 13,000×g for 20 minutes. The resulting supernatant was transferred to 45 Ti bottle assemblies (Beckman) and spun in a 45Ti rotor at 44,000 RPM for 1.5 hrs. The volume of the resulting supernatant was measured and 0.27 g/ml of ammonium sulfate was added. After stirring for 30 minutes, the precipitate was collected by spinning in the 45 Ti rotor at 40,000 RPM or 30 minutes. The resulting pellet was resuspended using a B-pestle dounce in buffer H/0.0 (50 mM Hepes-KOH, pH 7.5, 1 mM EDTA, 1 mM EGTA, 5 mM Mg Acetate, 0.02% NP-40, 10% glycerol) and dialyzed versus H/0.15M KCl (Buffer H with 0.15M KCl added). This preparation typically yielded 12–16 g soluble protein (determined by Bradford assay with a bovine serum albumin standard). Preparation of ORC from this extract was essentially as described (Bell and Stillman, 1992) with the following changes (column sizes used for preparation of ORC from 400 g of cells are indicated in parenthesis). The S-Sepharose column was loaded at 20 mg protein per ml of resin (~300 ml). The Q-Sepharose (50 ml) and sequence specific affinity column (5 ml) was run as described but the dsDNA cellulose column was omitted from the preparation. Only a single glycerol gradient was performed in an SW-41 rotor spun at 41,000 RPM for 20 hrs. We estimate a yield of 130 µg of ORC complex (all subunits combined) per 400 g of yeast cells.

Digestion of ORC subunits was performed using an "in gel" protocol described by Kawasaki and Suzuki with some modification. Briefly, purified ORC (~10 µg per subunit) was first separated by 10% SDS-PAGE and stained with 0.1% Coomassie Brilliant Blue G (Aldrich) for 15 min. After destaining (10% methanol, 10% acetic acid), the gel was soaked in water for one hour, then the protein bands were excised, transferred to a microcentrifuge tube and cut into 3–5 pieces to fit snugly into the bottom of the tube. A minimum volume of 0.1M Tris-HCl (pH=9.0) containing 0.1% SDS was added to completely cover the gel pieces. Then 200 ng of Achromobacter protease I (Lysylendopeptidase: Wako) was added and incubated at 30° C. for 24 hrs. After digestion the samples were centrifuged and the supernatant was passed through an Ultrafree-MC filter (Millipore, 0.22 µm). The gel slices were then washed twice in 0.1% TFA for one hour and the washes were recovered and filtered as above. All filtrates were combined and reduced to a volume suitable for injection on the HPLC using a speed-vac. The digests were separated by reverse-phase HPLC (Hewlett-Packard 1090 system) using a Vydac C18 column (2.1×250 mm, 5 µm, 300 angstroms) with an ion exchange pre-column (Brownlee GAX-013, 3.2×15 mm). The peptides were eluted from the C-18 column by increasing acetonitrile concentration and monitored by their absorbance at 214, 280, 295, and 550 nm. Amino acid sequencing of the purified peptides was performed on an automated sequencer (Applied Biosystems model 470) with on-line HPLC (Applied Biosystems model 1020A) analysis of PTH-amino acids.

ORC1: To clone the gene for the largest (120 kd) subunit of ORC, degenerate oligonucleoide primers were synthesized based on the sequence of a sequenced ORC1 peptide. These oligos were used to perform PCR reactions using total yeast genomic DNA from the strain W303 a as target. A 48 base pair fragment was specifically amplified. This fragment was subcloned and sequenced. The resulting sequence encoded the predicted peptide indicating that it was the correct amplification product. A radioactively labeled form of the PCR product was then used to probe a genomic library of yeast DNA sequences resulting in the identification of two overlapping clones. Sequencing of these clones resulted in the identification of a large open reading frame that encoded a protein with a predicted molecular weight of 120 kd and that encoded the sequenced ORC1 peptide sequences.

ORC3: To clone the gene for the 62 kd subunit of ORC, the degenerate oligonucleoide primers were synthesized based on the sequence of a sequenced ORC3 peptide. These oligos were used to perform PCR reactions using total yeast genomic DNA from the strain W303 a as target. A 53 base pair fragment was specifically amplified. This fragment was subcloned and sequenced. The resulting sequence encoded the predicted peptide indicating that it was the correct amplification product. A radioactively labeled form of the PCR product was then used to probe a genomic library of yeast DNA sequences resulting in the identification of two overlapping clones. Sequencing of these clones resulted in the identification of a large open reading frame that encoded a protein with a predicted molecular weight of 71 kd and encoded the sequenced ORC3 peptide sequences.

ORC4: By comparing the sequence of the ORC4 peptides to that of the known potentially protein encoding sequences in the genbank database we found that a portion of the ORC4 coding sequence had been previously cloned in the process of cloning the adjacent gene. We designed a perfect match oligo and use this to screen a yeast library. Using this oligo as a probe of the same yeast genomic DNA library a lambda clone was isolated that contained the entire ORC4 gene. This gene encoded a protein of predicted molecular weight 56 kd and also all of the peptides derived from the peptide sequencing of the 56 kd subunit.

ORC5: To clone the gene for the 53 kd subunit of ORC, the following degenerate oligonucleoide primers were synthesized based on the sequence of an ORC5 peptide. These oligos were used to perform PCR reactions using total yeast genomic DNA from the strain W303a as target. A 47 base pair fragment was specifically amplified. This fragment was subcloned and sequenced. The resulting sequence encoded the predicted peptide indicating that it was the correct amplification product. A radioactively labeled form of the PCR product was then used to probe a genomic library of yeast DNA sequences resulting in the identification of a single lambda clone. Sequencing of this clones resulted in the identification of a large open reading frame that encoded a several of the peptide sequences derived from the 53 kd subunit of ORC indicating that this was the correct gene. However the sequence of the 5' end of the gene was not present in this lambda clone. Fortuitoulsy, the mutations in the same gene had also been picked up in the same screen that resulted in the identification of the ORC2 gene. A complementing clone to this mutation was found to overlap with the lambda clone and contain the entire 5' end of the gene. Sequencing of this complementing DNA fragment resulted in the identification of the entire sequence of the ORC5 gene.

2. Isolation and cloning of ORCs from other species.

The *S. cerevisiae* ORC 1 gene encodes a protein that is the largest subunit of ORC. The ORC1 protein has two regions of homology with other known proteins; at the amino terminus there is homology with SIR3, a *S. cerevisiae* gene involved in transcriptional repression, and in the carboxyl region there is homology with a class of nucleotide binding proteins. To identify genes related to ORC1 in closely related yeast species, we took a PCR approach with primers based on amino acids conserved between ORC1 and SIR3 and identified a gene highly related to ORC1 in the yeast Kluyveromyces lactis, a budding yeast closely related to *S. cerevisiae* and the pathogenic yeast Candida albicans. SEQUENCE ID NOS: 13 and 14 show the cDNA and conceptual translate of ORC1 from *K. lactis*, coding is from nucleotides 395-3056. Another ORC1 gene was identified in the fission yeast Schizosaccharomyces pombe by low stringency DNA hybridizations. SEQUENCE ID NOS: 15 and 16 show the cDNA and conceptual translate of ORC1 from *S. pombe*, coding is from nucleotides 86-2209.

An alignment of the three yeast species of ORC 1 revealed areas of the protein that were highly conserved. To identify an ORC1-related gene in human cells, we designed degenerate PCR primers to domains conserved between three related yeast ORC1 genes. These primers were used in pairwise combinations on human cDNA to identify a human ORC 1 gene. PCR products that were found to be related to ORC1 were then used to isolate a full-length cDNA.

cDNA Synthesis: Reverse transcription of total RNA isolated from human 293 cells was carried out in 30 µl reactions containing 10 µg total RNA, 10 pmole of primer, 6 µl of 5× Superscript II reaction buffer, 1 mM DTT, 1 mM dNTPs, 25 units of RNasin (Promega), and 200 units of Superscript II reverse transcriptase (GIBCO-BRL). The RNA and primers were heated at 70° C. for 5 minutes and then cooled on ice. The remaining reaction components were added and the reactions were carried out at 37° C. for 1 hour. The reverse transcriptase was inactivated at 70° C. for 15 minutes and the reactions were phenol-extracted and ethanol precipitated. The products were resuspended in 250 µl of DEPC-treated water and used in PCR reactions.

PCR: PCR reactions were carried out in 50 µl reactions containing 5 µl of template cDNA synthesized with primer PO1PCR5, 100 pmole of each primer, 10% DMSO, 1.5 mM dNTPs, 5 µl 10× reaction buffer [166 mM ammonium sulfate, 670 mM Tris-HCl (pH 8.8), 20 mM $MgCl_2$, 100 mM B-mercaptoethanol, 67 µM EDTA] 4–6 mM MgC12, and 1.5 units of Taq DNA polymerase (Boeringer-Mannheim). The reactions were overlaid with mineral oil and cycled in a Perkin-Elmer Thermal cycler 480 with the first cycle consisting of denaturation for 2 minutes at 94° C., annealing for 1 minute at 42° C., and extension for 1 minute at 72° C., followed by 27 cycles of 40 sec at 94° C., 1 minute at 42° C., 1 minute art 72° C., with a final extension of 5 minutes at 72° C. The reactions were phenol-extracted, precipitated, and analyzed on an 8% TBE polyacrylamide gel. Products of the correct predicted size were extracted from the gel, cloned and analyzed by sequencing. Sequence analysis of several clones revealed homology between the primer binding sites to *S. cerevisiae* ORC1. An internal, exact primer was designed and used in conjunction with 3' RACE (described below) to identify a larger fragment.

3' RACE: cDNA Synthesis: Reverse transcription of 10 µg of total 293 RNA was carried out in 30 µl reaction containing 10 µM 3' anchor primer, as described above, except that the reaction was carried out for 30 minutes at 37° C., 30 minutes at 42° C., with a final incubation for 15 minutes at 50° C. The reverse transcriptase was inactivated by heat treatment at 70° C. for 15 minutes. The reaction was phenol-extracted, ethanol precipitated, and the products were resuspended in 300 µl of DEPC-treated water and used as template for RACE reactions.

RACE: First-round 3' RACE PCR reactions were performed in a 50 µl reaction containing 100 pmole of each primer, 5 µl of cDNA, 1.5 mM dNTPs, 10% DMSO, 6 mM MgC12, and 2.5 units of Taq DNA polymerase. Thermal cycling was performed with the first cycle consisting of denaturation at 94° C. for 3 minutes, annealing at 55° C. for 1 minute, and extension at 72° C. for 20 minutes for one cycle, followed by 28 cycles of 94° C. for 1 minute, 55° C. for 1 minute, and 72° C. for 4 minutes with a final extension at 72° C. for 10 minutes.

Second-round PCR was performed as described for the first round except that the template was 1 µl from the first round PCR reaction, and the 3' anchor primer was replaced with the 3' adapter primer. The reaction was cycled for 29 cycles of 94° C. for 1 minute, 55° C. for 1 minute, and 72° C. for 4 minutes, with a final extension at 72° C. for 10 minutes. The reactions were phenol-extracted, ethanol-precipitated and analyzed by electrophoresis on 1% agarose gel and visualized with ethidium bromide. Amplified products were gel purified, cloned and sequenced. Sequence analysis revealed clones with high homology to *S. cerevisiae* ORC1.

To isolate a full-length cDNA, we screened a phage lambda gt10 cDNA library constructed from NTERD21, an embryonic carcinoma human cell line, with a RACE product as a probe. A total of 950,000 plaques were screened by hybridization at 65° C. in 7% SDS/0.25M NaPO4, pH 7.0. The filters were washed with successively stringent washes, with the final wash of 0.2× SSC, 0.1% SDS at 65° C. Positives plaques were purified and phage DNA was isolated, cloned into pKS+ and sequenced on both strands using an automated sequencer (Applied Biosystems).

SEQUENCE ID NOS: 17 and 18 show the cDNA and conceptual translate of human ORC1: the coding region is from 220 to 2805. An alignment of the 4 ORC1-related genes is shown in Table 1.

TABLE 1

Comparison of the ORC1 genes in yeast and human. The amino acid sequences of ORC1 from the yeast *K. lactis* (klorc1), *S. cerevisiae* (scorc1), *S. pombe* (sporc1) snd human (hsorc1) were aligned using the GCG program PILEUP.

```
                1                                                                           50
klorc1          ..........  ..........  ..........  ..........  ..........
(SEQ ID NO:14)
scorc1          ..........  ..........  ..........  ..........  ..........

(SEQ ID NO:2)
hsorc1          MAHYPTRLKT  RKTYSWVGRP  LLDRKLHYQT  YREMCVKTEG  CSTEIHIQIG (SEQ ID NO:18)
sporc1          ..........  ..........  ..........  ..........  ..........

(SEQ ID NO:16)

51                                                                          100
klorc1          ..........  ....MASTLA  EFEVQWEIQK  TDLKGNLIAE  TPRR.RRRGD
scorc1          ..........  ....MAKTLK  DLQ.GWEIIT  TDEQGNIIDG  GQKRLRRRGA hsorc1          QFVLIEGDDD  ENPYVAKLLE  LFEDDSDPPP  ...KKRARVQ  WFVRFCEVPA sporc1          ..........  ..........  .......MPR  ...RKSLRSQ  LLIN......

101                                                                         150
klorc1          ATEHEVINLV  RYDGVRLYPG  VTIVCKVEGA  DELSAYMIHE  VRLNT.SNYV
scorc1          KTEHYLKR..  SSDGIKLGRG  DSVVMHNEAA  GTYSVYMIQE  LRLNTLNNVV hsorc1          CKRHLLGRKP  GAQEIFWDY   PACDSNINAE  TIIGLVRVIP  LAPKDVVPTN sporc1          ..........  GIDKSLLSDD  SADSSDIDEE  EVYGVWTEEP  FQKEA.....

151                                                                         200
klorc1          ELWCLNYLSW  YEINAAERYK  QLDGEFYETN  KEKGDKFFEE  TFASQSIKNE
scorc1          ELWALTYLRW  FEVNPLAHYR  QFNPDANILN  ..RPLNYYNK  LFSETANKNE hsorc1          LKNEKTLFVK  LSWNEK.KFR  PLSSELFAEL  NKPQ......  ...ESAAKCQ sporc1          ...GRSYYRS  LKKNDV.IYR  ......VGDD  ITVH......  ...DGDSSFY 201                                                                         250
klorc1          LYLTAELSEI  YLRDLQFVAN  IKNEKEYLDS  VNEGKMDSNM  .FLCRSACLP
scorc1          LYLTAELAEL  QLFNFIRVAN  VMDGSKW..E  VLKGNVDPER  DFTVRYICEP hsorc1          KPVRAKSKSA  ESPSWTPAEH  VAKRIESRHS  ASKSRQTPTH  PLTPRARKRL sprocl          LGVICKLYEK  AIDKHSGKKY  VEAIWYSRAY  AKRMEIKPEY  LLPDR...HI 251                                                                         300
klorc1          SGTNLADLDI  HFFEEKIRSS  NPKVSLEY..  LRDITLPKLP  KPLNK.....
scorc1          TGEKFVDINI  EDVKAYIKKV  EPREAQEY..  LKDLTLPSKK  KEIDR.....

hsorc1          ELGNLGNPQM  SQQTSCASLD  SPRGRIKRKV  AFSEITSPSKR  SQPDKLQTLS sporc1          NEVYVSCGRD  ENLTSCI...  ....IEHCNV  YSEAEFFSK.  ..........

301                                                                         350
klorc1          SKVHAREKVV  ATKLQSDNTP  SKKSFQQTVS  KTNAEVQRIA  STIVNEKEAI
scorc1          G.PQKKDKAT  QTAQISDAET  RATDITDNED  GNEDE.....  .....SSDYE hsorc1          PALKAPEKTR  ETGLSYTEDD  KKASPEHRII  LRTRIAASKT  IDIREERTLT sporc1          ..FPAGIPTK  RKDL......  ...FPCNFFI  RRGVHLKVNK  YTEPLDWSYY 351                                                                         400
klorc1          SDNESDLSEY  HESKEEFANA  SSSDSDEEFE  DYQSAEELAI  VEPAKKKVRS
scorc1          SPSDIDVSED  MDSGEISADE  LEEEEDEEED  EDEEEKEARH  TNSPRKRGRK hsorc1          PISGGQRSSV  VPSVILKPEN  IKKRDAKEAK  AQNEATSTPH  RIRRKSSVLT sporc1          AHNLERIEDL  LVEMEENLRP  TKKKSGSRGR  GRPRKYPLPN  .VESKESSSK
```

TABLE 1-continued

Comparison of the ORC1 genes in yeast and human. The amino acid sequences of ORC1 from the yeast
*K. lactis* (klorc1), *S. cerevisiae* (scorc1), *S. pombe* (sporc1) snd human (hsorc1) were aligned using the GCG program PILEUP.

```
        401                                                                    450
klorc1  I . . . KPDI PI  S . . . . . . . .  . . . . . PVKSQ  TPLQPSAVHS  SP . . . . RKFF
scorc1  I KLGKDDI DA     SVQPPPKKRG         RKPKDPSKPR        QMLLI SSCRA  NNTPVI RKFT hsorc1  MNRI RQQLRF     LGNS . . . . . .   . . . . KSDQEE    KEI LPAAEI S  DSSSDEEEAS sporc1  VNSKDENFDL      QDDS . . . . . .   . . . . ESSSEDNLTI QPQT . . .   . . . . . . . . . .

451                                                                    500
klorc1  KNNI VRAKKA     YTPFSKRYKN          . PKI PDLNDI     FQRHNNDLDI   AA . . LEERFR
scorc1  KKNVARAKKK      YTPFSKRFKS          I AAI PDLTSL     PEFYGNSSEL    MASRFENKLK hsorc1  TPPLPRRAPR      TVSRNLRSSL          KSSLHTLTKV       PKKSLKPRTP    RCAAPQI RSR sporc1  . . . . PRR . . .  . . . RHKRSRH   NSS . . NLAST    PKRNGYGKPL    QI TPLPI RML 501                                                                    550
klorc1  TVSAKGKMET      I FSKVKKQLN         SRNSKEEI VK     AADFDNYLPA    RENEFASI YL
scorc1  TTQKHQI VET     I FSKVKKQLN         SSYVKEEI LK     SANFQDYLPA    RENEFASI YL hsorc1  SLAA . QEPAS    VLEEARLRLH          VSAVPES . . .   . . . . . . . LPC   REQEFQDI YN sporc1  SL . E . EFQGS  PHRKARAMLH          VASVPST . . .   . . . . . . . LQC   RDNEFSTI FS 551                                                                    600
klorc1  SLYSAI EAGT     STSI YI AGTP        GVGKTLTVRE       VVKDLMTSAD    QKELPRFQYI
scorc1  SAYSAI ESDS     ATTI YVAGTP         GVGKTLTVRE       VVKELLSSSA    QREI PDFLYV hsorc1  FVESKLLDHT      GGCMYI SGVP         GTGKTATVHE       VI RCLQQAAQ   ANDVPPFQYI sporc1  NLESAI EEET     GACLYI SGTP         GTGKTATVEH       VI WNLQELSR   EGQLPEFSFC 601                                                                    650
klorc1  EI NGLKI VKA    SDSYESFWQK          I SGEKLTSGA     AMESLEFYFN    KVPATKKRPI
scorc1  EI NGLKMVKP     TDCYETLWNK          VSGERLTWAA       SMESLEFYFK    RVPKNKKKTI hsorc1  EVNGMKLTEP      HQVYVHI LQK         LTGQKATANH       AAELLAKQFC    TRGSPQE . TT sporc1  EI NGMRVTSA     NQAYSI LWES         LTGERVTPI H      AMDLLDNRFT    HASPNRS . SC 651                                                                    700
klorc1  VVLLDELDAL      VSKSQDVMYN          FFNWATYSNA       KLI VVAVANT   LDLPERHLGN
scorc1  VVLLDELDAM      VTKSQDI MYN         FFNWTTYENA       KLI VI AVANT  MDLPERQLGN hsorc1  VLLVDELDLL      WTHKQDI MYN         LFDWPTHKEA       RLVVLAI ANT   MDLPERI MMN sporc1  VVLMDELDQL      VTHNQKVLYN          FFNWPSLPHS       RLI VVAVANT   MDLPERI LSN 751                                                                    800
klorc1  PDSSTI ETDE     EEXRXDFSNY          KRLKLRI NPD      AI EI ASRKI A  SVSGDVRRAL
scorc1  AAGNDTTVKQ      TLP . . . . EDV     RKVRLRMSAD       AI EI ASRKVA   SVSGDARRAL hsorc1  . . . . . . . . . .  . . . . . . . . . .  . . . . . . . EDD      AI QLVARKVA    ALSGDARRCL sporc1  . . . . . . . . . .  . . . . . . . . . .  . . . . . . . S SD      AI RFAARKVA    AVSGDARRAL 801                                                                    850
klorc1  KVVKRAVEYA      ENDYLKRLRY          E . . . . . . . .  . . . . . . . . .   . . RLVNSK . .
scorc1  KVCKRAAEI A     EKHYMAKHGY          GYDGKTVI ED       ENEEQI YDDE   DKDLI ESNKA hsorc1  DI CRRATEI C    EF . . . . . . .    . . . . . . . . .  . . . . . . . . .   . . . . . . . . . .

sporc1  DI CRRASELA     E . . . . . . . .   . . . . . . . . .  . . . . . . . . .   . . . . . . . . . .

851                                                                    900
klorc1  KDTSGNGTGN      EELQSVEI KH         I TKALNESST      SPEQQFI SGL   SFSGXLFLYA
scorc1  KDDNDDDDDN      DGVQTVHI TH         VMKALNETLN       SHVI TFMTRL   SFTAKLFI YA hsorc1  . . . . . SQQKP  DSPGLVTI AH        SMEAVDEMFS       SSYI TAI KNS  SVLEQS FLRA sporc1  . . . . . . . . . .  NKNGKVTPGL     I HQAI SEMTA     SPLQKVLRNL    SFMQKVFLCA
```

TABLE 1-continued

Comparison of the ORC1 genes in yeast and human. The amino acid sequences of ORC1 from the yeast
K. lactis (klorc1), S. cerevisiae (scorc1), S. pombe (sporc1) snd human (hsorc1) were aligned using the GCG program PILEUP.

```
        901                                                                  950
klorc1  L I N L I  K K K Q T   D V Q . L G D I V E   E M R L L I D V N G   N N K Y I L E L K R   I L F Q N D S V D T
scorc1  L L N L M K K N G S   Q E Q E L G D I V D   E I K L L I E V N G   S N K F V M E I A K   T L F Q Q G S D N I hsorc1  I L A E F R R S G L   E E A T F Q Q I Y S   Q H V A L C R M E G   L P Y P T . . . . .   . . . . . . . . . . .

sporc1  I V N R M R R S G F   A E S Y V Y E V L E   E A E R L L R V M T   T P D A E A K F G E   L I . . . . . . . .

951                                                                 1000
klorc1  K E Q L R A V S W D   Y I L L Q L L D A G   V V V R Q Y F . . K   N E R L S T I K L N   I S M E D A D E C L
scorc1  S E Q L R I I S W D   F V L N Q L L D A G   I L F K Q T M . . K   N D R I C C V K L N   I S V E E A K R A M hsorc1  . . . . . M S E T M   A V C S H L G S C R   L L L V E . . P S R   N D L L L R V R L N   V S Q D D V L Y A L sporc1  . . . L R R P E F G   Y V L S S L S E N G   V L Y L E N K S S R   N A . . . R V R L A   I A D D E I K L A F 1001        1010
klorc1  H E D Q M L K T F .
scorc1  N E D E T L R N L .

hsorc1  K D E * . . . . . .

sporc1  R G D S E L A G I A
```

As can be seen, the sequence alignment shows a high degree of sequence identity and similarity. For example, the S. cerevisiae and K. lactis amino acid sequences are 50% identical whereas the more distantly related S. cerevisiae and human amino acid sequences are 27% identical with each other. This demonstrates that the ORC proteins are conserved from yeast to human.

Partial eDNA sequences from A. thaliana and C. elegans, translated amino acid sequences showing sequence similarity to the S. cerevisiae ORC2 protein sequences shown herein were identified in the NCBI dbest database by computer based sequence searching. Those DNA fragments were isolated by a PCR based method using DNA isolated from lambda eDNA libraries as a template. Entire cDNAs were then isolated using the partial cDNAs to design primers for PCR or as probes to screen the cDNA library. The amino acid sequences predicted from these eDNA libraries were aligned and conserved regions were used to design degenerate oligonucleotide primers to isolate a partial cDNA from human. This partial cDNA was amplified by RT-PCR using the degenerate primers and cloned into a plasmid vector. Full length cDNAs were then isolated from the cDNA library by using the PCR generated DNA fragment as a probe. Each DNA and protein sequence and the result of the alignment among four species are shown below.

Isolation of A. thaliana ORC2: Four DNA sub fragments were isolated to cover the full length of the eDNA. First, a partial eDNA sequence (344 bp), the translated amino acid sequence from which is similar to a region from the ORC2 protein from S. cerevisiae, was identified in the NCBI dbest database (#1443). A probe was obtained to screen the a eDNA library using standard PCR reactions with a lambda phage cDNA library as a template and oligonucleotide primers based on the DNA sequence in the dbest database. The resulting PCR fragment was cloned into a BlueScript plasmid vector and sequenced. Next, to extend this isolated DNA sequence in both directions, nested PCR using two primers (20 mer) complementary to each end of the isolated DNA were designed. PCR reactions were performed using one of these specific primers and a primer from the vector (ZAPII). The 5'-end and 3'-end (containing the polyA tail) DNA fragments were amplified by nested PCR using a second (internal) primer and the products cloned and sequenced. Finally, the 5'-end of the cDNA fragment was isolated by the 5'-RACE procedure using two oligonucleotides complementary to the most 5' end of the isolated cDNAs and the CLONTECH RACE procedure. The combined clones covered the entire A. thaliana cDNA. SEQUENCE ID NOS: 19 and 20 show the cDNA and conceptual translate of ORC2 from A. thaliana; the coding region is from 277 to 1368.

Isolation of C. elegans ORC2:First, a partial eDNA sequence (446 bp) homologous to the S. cerevisiae ORC2 gene and a genomic DNA sequence containing this sequence were identified in the NCBI dbest (#16625) and embl (#Z36949) databases, respectively. The partial cDNA fragment was amplified by nested PCR using DNA from a ZAP cDNA library and oligonucleotides complementary to the dbest DNA sequence. The PCR product was cloned and used as a probe to screen the C. elegans cDNA lambda library). $5\times10^5$ plaques were screened and the a length of the cDNA was isolated. SEQUENCE ID NO:21 and 22 show the cDNA and conceptual translate of ORC2 from C. elegans; the coding region is from 13 to 1305.

Isolation of a human ORC2: Based on the computer assisted alignment of the amino acid sequences of ORC2 from S. cerevisiae, A. thaliana and C. elegans, degenerate oligonucleotide probes were designed isolate a partial cDNA from human cells by reverse transcriptase assisted PCR. A 340-bp partial cDNA homologous to ORC2 gene in S. cerevisiae was isolated by RT-PCR reaction against human HeLa cell mRNA. First strand cDNA was synthesized using an oligo(dT) primer against 2 mg of HeLa mRNA at 42° C. for 1 hour. One hundredth volume of this cDNA pool was used as a template for the PCR reaction. This PCR also amplified DNA from K. lactis that was related to the S. cerevisiae ORC2 gene. The PCR reaction conditions were 94° C. for 45 seconds/46° C. for 45 seconds/72° C. for 2 minutes for 70 cycles. The PCR product was cloned and sequenced and found to be related to the three ORC2 sequences.

Next, using this DNA fragment as a probe, cDNA clones covering a complete ORF from the gene were isolated from a human lambda phage cDNA library derived from human embryonic carcinoma cells. 5×10⁵ plaques were screened and 6 positive clones were isolated. Both strands of these cDNAs were determined without any gaps. SEQEUENCE ID NOS:23 and 24 show the cDNA and conceptual translate of human ORC2: the coding region is from 187 to 1920.

A multiple alignment of the cDNA sequences from *S. cerevisiae, A. thaliana, C elegans* and human reveals that all four sequences are highly related to each other (Table 2). For example, the percent identities between the *S. cerevisiae* ORC2 amino acid sequence and the *A. thaliana, C elegans* and human sequences are 31%, 23% and 24% respectively.

Table 2. Multiple amino acid sequence alignment of four ORC2 protein sequences. atorc2, hsorc2, scorc2 and ceorc2 represent the ORC2 protein derived from *A. thaliana*, human, *S. cerevisiae* and *C. elegans*, respectively. FIG. 8. Multiple amino acid sequence alignment of four ORC2 protein sequences. atorc2, hsorc2, scorc2 and ceorc2 represent the ORC2 protein derived 15 from A. thaliana, human, S. cerevisiae and C. elegans, respectively.

```
             1                                                                              50
atorc2       . . . . . . . . . .   . . . . . . . . . .   . . . . . . . . . .   . . . . . . . . . .   . . . . . . . . . .
(SEQ ID NO:20)
hsorc2       MS K P E L KE D K     ML E V H F V G D D     D V L N H I L D R E   G G A K L K K E R A   H V L V N P K K I I
(SEQ ID NO:24)
scorc2       . . . . . . . . . .   . . . . . ML N G E     D F V E H N D I L S   S P A K S R N . . .   . . . V T P K R V D
(SEQ ID NO:4)
ceorc2       . . . . . . . . . .   . . . . . . . . . .   . . . . . . . . . .   . . . . . . . . . .   . . . . . . . . . .
(SEQ ID NO:22)

51                                                                             100
atorc2       . . . . . . . . . .   . . . . . . . . . .   . . . . . . . . . .   . . . . . . . . . .   . . . . . . . . . .
hsorc2       K K P E Y D L E E D   D Q E V L K D Q N Y   V E I M G R D V Q E   S L K N G S A T G G   G N K V Y S F Q N R
scorc2       P H G E R Q L R R I   H S S K K N L L E R   I S L V G N E R K N   T S P D P A L K P K   T P S K A P R K R G
ceorc2       . . . . . . . . . .   . . . . . . . . . .   . . . . . . . . . .   . . . . . . . . . .   . . . . . . . . . .

101                                                                            150
atorc2       . . . . . . . . . .   . . . . . . . . . .   . . . . . . . . . .   . . . . . . . . . .   . . . . . . . . . .
hsorc2       K H S E K M A K L A   S E L A K T P Q K S   V S F S L K N D P E   I T I N V P Q S S K   G H S A S D K V Q P
scorc2       R P R K I Q E E L T   D R I K K D E K D T   I S S K K K R K L D   K D T S G N V N E E   S K T S N N K Q V M
ceorc2       . . . . . . . . . .   . . . . . . . . . .   . . . . . . . . . .   . . . . . . . . . .   . . . . . . . . . .

151                                                                            200
atorc2       . . . . . . . . . .   . . . . . . . . . .   . . . . . . . . . .   . . . . . . . M E D   I E N I E E D E Y G
hsorc2       K N N D K S E F L S   T A P R S L R K R L   I V P R S H S D S E   S E Y S A S N S E D   D E G V A Q E H E E
scorc2       E K T G I K E K R E   R E K I Q V A T T T   Y E D N V T P Q T D   D N F V S N S P E P   P E P A T P S K K S
ceorc2       . . . . . . . . M P   R P K I L K R A T V   Q P S A A V P V K K   S T P E K E G S R Q   K K T N G K E N A S 201                                                                            250
atorc2       F S R N Y F L A . .   . . . . . . . . . K   E L . . . . . . . .   . . . . . G G A S K   R . . . . . . . . .
hsorc2       D T N A V I F S . .   . . . . . . . . . Q   K I Q A Q N R V V S   A P V G K E T P S K   R M K R D K T S D L
scorc2       L T T N H D F T S P   L K Q I I M N N L K   E Y K D S T S P G K   L T L S R N F T P T   P V P K N K K L Y Q
ceorc2       R N L Q S N L E E D   L E Q L G F E D E T   V S M A Q S A I E N   Y F M Q G K S A S E   R M N N A K S R R G 251                                                                            300
atorc2       . . . . . S A H K L   S D I H I . . . . .   . . . . . . . V D E   Q E L R E T A S T I   E M K H S K E I S E
hsorc2       V E E Y F E A H S S   S K V L T S D R T L   Q K L K R A L K L D   Q Q T L R N L L S K V   S P S F S A E L K Q
scorc2       T S E T K S A S S F   L D T F E G Y F D Q   R K I V R T N A K S   R H T M S M A P D V   T R E E F S L V S N
ceorc2       R R A G N G N T E E   I E . . . . . . . .   . . . . . . . . E D   D E I S N A I T D F   T K C D L P G L R N 301
atorc2       L M S D Y . . . . .   . . . . . . . . K T   M Y S K W V F E L R   C G F G L L M Y G F   G S K K A L V E D F
hsorc2       L N Q Q Y . . . . .   . . . . . . . . E K   L F H K W M L Q L H   L G F N I V L Y G L   G S K R D L L E R F
scorc2       F F N E N F Q K R P   R Q K L F E I Q K K   M F P Q Y W F E L T   Q G F S L L F Y G V   G S K R N F L E E F
ceorc2       Y I T K K D N T E F   E K R L E H L A D N   D F G K W K L Y L A   A G F N I L L H G V   G S K R D V L T E F 351                                                                            400
atorc2       A S A S L T D Y S .   . . . . . . . . . .   . . . . . . . . . .   V V V I N G Y L P S   V N L K Q V L L A L
hsorc2       R T T M L Q D S I .   . . . . . . . . . .   . . . . . . . . . .   H V V I N G F F P G   I S V K S V L N S I
scorc2       A I D Y L S P K I A   T S Q L A Y E N E L   Q Q N K P V N S I P   C L I L N G Y N P S   C N Y R D V F K E I
```

-continued

```
ceorc2  E N E L . . . . . .                                   . S D Y T   Y M R V D A R K D G   L N V K V L L G A I 401                                                                                              450
atorc2  A E L L S E L L K C   K R K S S G S L S K   G Q E T F . P S R S   M D D I L S F L H G   P Q S G D K . D C F
hsorc2  T E E V L D H M . .   . . . . . . . . . .   . . G T F . . R S     I L D Q L D W I V N   K F K E D S . S L E scorc2  T D L L V . . . . .   . . . . P A E L T R   S E T K Y . W G N H   V I L Q I Q K M I D   F Y K N Q P L D I K ceorc2  N E N M . . . . . .   . . K L N C N V K R   G Q S T I S W A R S   I R R K M N . . . .   . . . . . . . S Q Q 451                                                                                              500
atorc2  I C V V V H N I D G   P A L R D P E S Q Q   T L A R L S S C H S HI R L V A S I D H V   N A P L L W D K K M
hsorc2  L F L L I H N L D S   Q M L R G E K S Q Q   I I G Q L S S L H N   I Y L I A S I D H L   N A P L M W D H A K scorc2  L I L V V H N L D G   P S I R K N T F Q T   M L S F L S V I R Q   I A I V A S T D H I   Y A P L L W D N M K ceorc2  L I L I I D N I E A   P D W R S D Q . E A   F C E L L E N R D S   V K L I A T V D H I   Y S T F I W N S R Q 501                                                                                              550
atorc2  V H K Q F N W L W H   H V P T F A P Y N V   E G V F F P L V . L   A Q G S . . . . T A   Q T A K T A A I V L
hsorc2  . Q S L F N W L W Y   E T T T Y S P Y T E   E T S Y E N S L . L   V K Q S . . . . G S   L P L S S L T H V L scorc2  A Q N . Y N F V F H   D I S N F E P S T V   E S T F Q D V M K M   G K S D . . . . T S   S G A E G A K Y V L ceorc2  L S S . L S F V H I   T I N T F E I P L Q   E L M T G D S R L L   G L D A R S N Q S S   H T M S S L D V F W 551                                                                                              600
atorc2  Q S L T P N G Q N V   F K I L A E Y Q L S   H P D E D . . . . .   . . . . . . . G M     P T D D L Y S A S R
hsorc2  R S L T P N A R G I   F R L L I K Y Q L D   N Q D N P S Y . . .   . . . . . . . I G L   S F Q D F Y Q Q C R scorc2  Q S L T V N S K K M   Y K L L I E T Q M Q   N M G N L S A N T G   P K R G T Q R T G V   E L K L F N H L C A ceorc2  K S L A V N S Q K L   F R L F F Q M Y F D   T K K . . . . . . .   . . . . . . . P V     K F W D L F N A A K 601                                                                                              650
atorc2  E R F F V S S Q V T   L N S H L T E F K D   H E L V K T K R N S   D G Q E C L N I P L   T S D A I R Q L L L
hsorc2  E A F L V N S D L T   L R A Q L T E F R D   H K L I R T K K G T   D G V E Y L L I P V   D N G T L T D F L E scorc2  A D F I A S N E I A   L R S M L R E F I E   H K M A N I T K N N   S G M E I I W V P Y   T Y A E L E K L L K 651                 662
atorc2  D L N Q . . . . .   . .
hsorc2  K E E E A . . . .   . .

scorc2  T V L N T L . . . .   . .

ceorc2  S K N M P L D E K K   D E
```

The foregoing sequence data and methods for isolating origin recognition complex proteins enable one of ordinary skill in this art to isolate ORC-encoding cDNA sequences from any eukaryotic species. These data from fungi (yeasts), plant and animal (invertebrate and human) show evolutionary sequence and function conservation. Using these data, we have also characterized an ORC5 sequence from *Drosophila melanogaster* (Genbank accession number L39626).

EXAMPLES

1. Protocol for high-throughput in vitro ORC complex binding assay

A. Reagents:

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.

$^{33}$P recombinant ORC protein 10× stock: $10^{-6}$–$10^{-8}$M equimolar "cold" mixture of recombinant ORC 1–6 proteins (baculovirus expression system) supplemented with 200,000–250,000 cpm of labeled ORC2 protein (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

Oligonucleotide stock: (specific biotinylated). Biotinylated oligo at 17 pmole/μl, ARS1 ori sequence ORC complex binding site.

B. Preparation of assay plates:

Coat with 120 μl of stock N-Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 10 μl compound or extract.

Add 10 μl $^{33}$P-ORC protein mixture (20,000–25,000 cpm/0.1–10 pmoles/well=$10^{-9}$–$10^{-7}$M final concentration).

Shake at 25° C. for 15 minutes.

Incubate additional 45 minutes at 25° C.

Add 40 μl oligonucleotide stock (1.0 pmoles/40 ul in assay buffer with 1 ng of ss-DNA)

Incubate 1 hour at room temperature.

Stop the reaction by washing 4 times with 200 μl PBS.

Add 150 μl scintillation cocktail.

Count in Topcount.

D. Controls for all assays (located on each plate):
   a. Non-specific binding (no oligo added)
   b. Specific soluble oligo at 80% inhibition.

2. Protocol for high-throughput in vitro ORC protein—protein binding assay.

A. Reagents:

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.

$^{33}$P recombinant ORC protein 10× stock: $10^{-6}$–$10^{-8}$M equimolar "cold" mixture of recombinant ORC 1–6 proteins (baculovirus expression system) supplemented with 200,000–250,000 cpm of labeled ORC2 protein (Beckman counter). Place in the 4° C. microfridge during screening.

Protease inhibitor cocktail (1000×): 10 mg Trypsin Inhibitor (BMB ##894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

recombinant ORC5 protein 10× stock: $10^{-8}$–$10^{-5}$M biotinylated ORC5 protein in PBS.

B. Preparation of assay plates:

Coat with 120 μl of stock N-Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 10 μl compound or extract.

Add 10 μl $^{33}$P-ORC protein mixture (20,000–25,000 cpm/0.1–10 pmoles/well =$10^{-9}$–$10^{-7}$M final concentration).

Shake at 25° C. for 15 minutes.

Incubate additional 45 minutes at 25° C.

Add 40 μl biotinylated ORC5 protein (0.1–10 pmoles/40 ul in assay buffer)

Incubate 1 hour at room temperature.

Stop the reaction by washing 4 times with 200 μl PBS.

Add 150 μl scintillation cocktail.

Count in Topcount.

D. Controls for all assays (located on each plate):
   a. Non-specific binding (no ORC5 protein)
   b. Soluble (non-biotinylated ORC5 protein) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of identifying lead compounds for a pharmacological agent useful in the diagnosis or treatment of disease associated with cell growth, said method comprising the steps of:

forming a mixture comprising;
a recombinant origin or replication (ORC) protein expressed from an isolated nucleic acid encoding said ORC protein, said ORC protein selected from the group consisting of ORC1, ORC2, ORC3, ORC4, ORC5 and ORC6,
a natural intracellular ORC protein binding target, wherein said binding target is capable of specifically binding said ORC protein, and
a candidate pharmacological agent;

incubating said mixture under conditions whereby, but for the presence of said candidate pharmacological agent, said ORC protein selectively binds said binding target;

detecting the presence or absence of specific binding of said ORC protein to said binding target, wherein the absence of said selective binding indicates that said candidate pharmacological agent is a lead compound that disrupts the cellular function of said ORC protein and thereby inhibits cell growth.

2. A method according to claim 1, wherein said ORC protein is a human ORC protein.

3. A method according to claim 1, wherein said ORC protein is a fungal ORC protein.

4. A method according to claim 1, wherein said ORC protein is ORC1.

5. A method according to claim 1, wherein said ORC protein comprises SEQ ID NO:2.

6. A method according to claim 1, wherein said ORC protein comprises SEQ ID NO: 14.

7. A method according to claim 1, wherein said ORC protein comprises SEQ ID NO: 16.

8. A method according to claim 1, wherein said ORC protein comprises SEQ ID No: 18.

9. A method according to claim 1, wherein said ORC protein is ORC2.

10. A method according to claim 1, wherein said ORC protein comprises SEQ ID NO:4.

11. A method according to claim 1, wherein said ORC protein comprises SEQ ID NO:20.

12. A method according to claim 1, wherein said ORC protein comprises SEQ ID NO:22.

13. A method according to claim 1, wherein said ORC protein comprises SEQ ID NO:24.

14. A method according to claim 1, wherein said ORC protein is ORC3.

15. A method according to claim 1, wherein said ORC protein comprises SEQ ID NO:6.

16. A method according to claim 1, wherein said ORC protein is ORC4.

17. A method according to claim 1, wherein said ORC protein comprises SEQ ID NO:8.

18. A method according to claim 1, wherein said ORC protein is ORC5.

19. A method according to claim 1, wherein said ORC protein comprises SEQ ID NO:10.

20. A method according to claim 1, wherein said ORC protein is ORC6.

21. A method according to claim 1, wherein said ORC protein comprises SEQ ID NO: 12.

* * * * *